United States Patent
Rabinowitz et al.

(10) Patent No.: US 12,329,816 B2
(45) Date of Patent: Jun. 17, 2025

(54) IMMUNOTHERAPY WITH METABOLIC ENZYME EXPRESSION

(71) Applicants: The Trustees of Princeton University, Princeton, NJ (US); The Trustees of the University of Pennsylvania, Philadelphia, PA (US)

(72) Inventors: Joshua D. Rabinowitz, Princeton, NJ (US); Roderick O'Connor, Philadelphia, PA (US)

(73) Assignees: The Trustees of Princeton University, Princeton, NJ (US); The Trustees of the University of Pennsylvania, Philadelphia, PA (US)

( * ) Notice: Subject to any disclaimer, the term of this patent is extended or adjusted under 35 U.S.C. 154(b) by 1060 days.

(21) Appl. No.: 17/270,323

(22) PCT Filed: Aug. 23, 2019

(86) PCT No.: PCT/US2019/047830
§ 371 (c)(1),
(2) Date: Feb. 22, 2021

(87) PCT Pub. No.: WO2020/041662
PCT Pub. Date: Feb. 27, 2020

(65) Prior Publication Data
US 2021/0379109 A1     Dec. 9, 2021

Related U.S. Application Data

(60) Provisional application No. 62/722,518, filed on Aug. 24, 2018.

(51) Int. Cl.
| | |
|---|---|
| *A61K 45/06* | (2006.01) |
| *A61K 38/50* | (2006.01) |
| *A61K 40/11* | (2025.01) |
| *A61K 40/31* | (2025.01) |
| *A61K 40/42* | (2025.01) |
| *A61P 35/00* | (2006.01) |
| *C12N 5/0783* | (2010.01) |

(52) U.S. Cl.
CPC .............. *A61K 45/06* (2013.01); *A61K 38/50* (2013.01); *A61K 40/11* (2025.01); *A61K 40/31* (2025.01); *A61K 40/4255* (2025.01); *A61P 35/00* (2018.01); *C12N 5/0636* (2013.01)

(58) Field of Classification Search
None
See application file for complete search history.

(56) References Cited

U.S. PATENT DOCUMENTS

2016/0361360 A1* 12/2016 Chang ................. A61P 17/00

FOREIGN PATENT DOCUMENTS

WO     2020/041662 A1     2/2020

OTHER PUBLICATIONS

Ron-Harel et al., Mitochondrial biogenesis and proteome remodeling promote one-carbon metabolism for T cell activation; 2016, Cell Metabolism, 24: 104-117. (Year: 2016).*
Ron-Harel et al., T cell activation depends on extracellular alanine; 2019, Cell Reports, 28: 3011-3021. (Year: 2019).*
Mackenzie et al., Functional properties and cellular distribution of the system A glutamine transporter SNAT1 support specialized roles in central neurons; 2003, 278(26): 23720-23730. (Year: 2003).*
Notification of International Preliminary Report on Patentability of International Application No. PCT/US2019/047830, entitled: "Immunotherapy With Metabolic Enzyme Expression," mailed Mar. 2, 2021.
Belviso, S. et al., "The human asparaginase enzyme (ASPG) inhibits growth in leukemic cells," PLOS, vol. 12; No. 5; 14 pages (2017).
Caruana, I. et al., "Heparanase promotes tumor infiltration and antitumor activity of CAR-redirected T lymphocytes," Nature Medicine, vol. 21; No. 5; 524-529 (2015).
Pavlova, N.N. et al., "As Extracellular Glutamine Levels Decline, Asparagine Becomes an Essential Amino Acid," Cell Metabolism, vol. 27; 428-438 (2018).
Rigouin, C. et al., "Discovery of human-like L-asparaginases with potential clinical use by directed evolution," Scientific Reports, vol. 7; No. 1; 10224; 13 pages (2017).
Sullivan, L.B. et al., "Aspartate is an endogenous metabolic limitation for tumor growth," Nature Cell Biology, vol. 20; No. 7; 782-788 (2018).
Zhang, J. et al., "Asparagine Plays a Critical Role in Regulating Cellular Adaptation to Glutamine Depletion," Molecular Cell, vol. 56; 205-218 (2014).
Notification of Transmittal of the International Search Report and the Written Opinion of International Application No. PCT/US2019/047830, entitled: "Immunotherapy With Metabolic Enzyme Expression," mailed Dec. 10, 2019.

* cited by examiner

*Primary Examiner* — Daniel E Kolker
*Assistant Examiner* — James Ryland Melchior
(74) *Attorney, Agent, or Firm* — Hamilton, Brook, Smith & Reynolds, P.C.

(57) ABSTRACT

The present invention provides, in some embodiments, methods of promoting an immune response in a subject in need thereof, comprising administering to the subject a population of immune cells that express an enzyme that facilitates immune cell function in a nutrient-poor environment. The invention also provides, in other embodiments, compositions comprising an ex vivo population of immune cells expressing an enzyme that enhances immune cell function in a nutrient-poor environment.

20 Claims, 12 Drawing Sheets
Specification includes a Sequence Listing.

IMMUNOTHERAPY WITH METABOLIC ENZYME EXPRESSION

RELATED APPLICATION

This application is the U.S. National Stage of International Application No. PCT/US2019/047830, filed Aug. 23, 2019, published in English, which claims the benefit of U.S. Provisional Application No. 62/722,518, filed on Aug. 24, 2018. The entire teachings of the above applications are incorporated herein by reference.

GOVERNMENT SUPPORT

This invention was made with government support under Grant Nos: DK113643 and CA226983, awarded by the National Institutes of Health. The government has certain rights in the invention.

INCORPORATION BY REFERENCE OF MATERIAL IN ASCII TEXT FILE

This application incorporates by reference the Sequence Listing contained in the following ASCII text file being submitted concurrently herewith:
 a) File name: 53911017002_CORRECTED_SEQUENCE_LISTING.txt; created Aug. 12, 2021, 190,000 bytes in size.

BACKGROUND

Metabolic factors can inhibit immune responses. For example, immune cells need a myriad of small molecules, such as glucose, glutamine, arginine, tryptophan, and other nutrients and metabolites to proliferate and to fight infection. When one or more of these nutrients is in short supply, immune response can be limited. A particular need of immune cells, which is shared also with cancer cells, is oxidized nicotinamide adenine dinucleotide (NAD) and oxidized carbon for use in synthesis of amino acids and nucleotides. Such oxidized cofactors and carbon may be in short supply in the tumor microenvironment, due to poor perfusion and low $O_2$.

Thus, there is a need for technologies that enable more effective immune responses in nutrient-limited environments, including environments limited in oxidized NAD and oxidized carbon.

SUMMARY OF THE INVENTION

The present invention provides, in an embodiment, a method of promoting an immune response (e.g., a T cell response, an anti-tumor immune response) in a subject in need thereof, comprising administering to the subject a population of immune cells that express an enzyme or transporter that produces an increase in the level of aspartate or alanine in the immune cells (e.g., an effective amount of a population of immune cells that express an enzyme or transporter that produces an increase in the level of aspartate or alanine in the immune cells).

The present invention also provides, in an embodiment, a method of promoting an immune response (e.g., a T cell response, an anti-tumor immune response) in a subject in need thereof, comprising administering to the subject a population of immune cells that express an enzyme (e.g., asparaginase) that catalyzes the formation of aspartate from asparagine, e.g., by hydrolysis of asparagine into aspartate and ammonia (e.g., an effective amount of a population of immune cells that express an enzyme (e.g., asparaginase) that catalyzes the formation of aspartate from asparagine, e.g., by hydrolysis of asparagine into aspartate and ammonia).

Also provided herein is a method of enhancing an immunotherapy in a subject receiving the immunotherapy, comprising administering to the subject a population of immune cells that express an enzyme or transporter that produces an increase in the level of aspartate or alanine in the immune cells (e.g., an effective amount of a population of immune cells that express an enzyme or transporter that produces an increase in the level of aspartate or alanine in the immune cells).

Also provided herein is a method of enhancing an immunotherapy in a subject receiving the immunotherapy, comprising administering to the subject a population of immune cells that express an enzyme (e.g., asparaginase) that catalyzes the formation of aspartate from asparagine, e.g., by hydrolysis of asparagine into aspartate and ammonia (e.g., an effective amount of a population of immune cells that express an enzyme (e.g., asparaginase) that catalyzes the formation of aspartate from asparagine, e.g., by hydrolysis of asparagine into aspartate and ammonia).

In another embodiment, the invention provides a method of treating a cancer in a subject in need thereof, comprising administering to the subject a population of immune cells that express an enzyme or transporter that produces an increase in the level of aspartate or alanine in the immune cells (e.g., an effective amount of a population of immune cells that express an enzyme or transporter that produces an increase in the level of aspartate or alanine in the immune cells).

The invention also provides, in an embodiment, a method of treating a cancer in a subject in need thereof, comprising administering to the subject a population of immune cells that express an enzyme (e.g., asparaginase) that catalyzes the formation of aspartate from asparagine, e.g., by hydrolysis of asparagine into aspartate and ammonia (e.g., an effective amount of a population of immune cells that express an enzyme (e.g., asparaginase) that catalyzes the formation of aspartate from asparagine, e.g., by hydrolysis of asparagine into aspartate and ammonia).

In yet another embodiment, the invention provides a composition comprising an ex vivo population of immune cells that express an enzyme or transporter that produces an increase in the level of aspartate or alanine in the immune cells.

In another embodiment, the invention provides a composition comprising an ex vivo population of immune cells that express an enzyme that catalyzes the formation of aspartate from asparagine.

Also provided herein are compositions (e.g., a composition disclosed herein) for promoting an immune response, enhancing an immunotherapy and/or treating cancer, as well as uses of the compositions disclosed herein in the manufacture of medicaments for promoting an immune response, enhancing an immunotherapy and/or treating cancer.

The compositions and methods described herein are useful, for example, in combination with other agents, such as PD-1, PD-L1, or CTLA-4 checkpoint inhibitors. The compositions and methods described herein, in certain embodiments, are also useful for improving the efficacy of immunotherapy methods, including CAR-T therapy.

BRIEF DESCRIPTION OF THE DRAWINGS

The foregoing will be apparent from the following more particular description of example embodiments, as illustrated in the accompanying drawings.

DETAILED DESCRIPTION OF THE INVENTION

Figure 1:
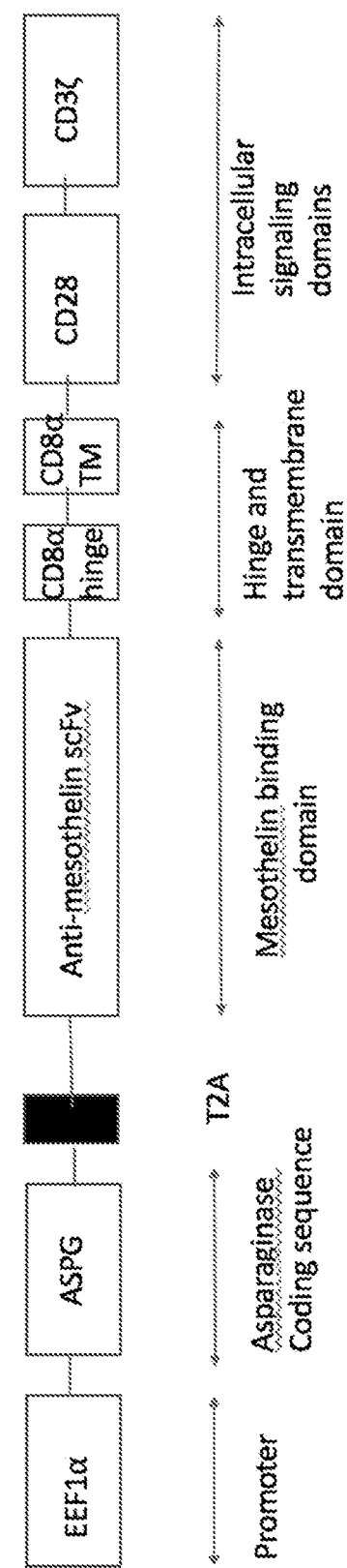
FIG. 1 is a vector map, and shows a lentiviral CAR construct designed to co-express guinea pig asparaginase.

A description of example embodiments of the invention follows.

Methods for Enhancing Immunotherapy

It is an object of the present invention to improve the effectiveness of immunotherapy, particularly cancer immunotherapy. The invention contemplates enhancing immune responses (e.g., T cell responses) against a target (e.g., a tumor) by creating immune cells (e.g., CAR-T cells) that are better able to cope with the metabolic environment of the target (e.g., the high lactate, low pH, low $O_2$, and sometimes amino-acid poor environment of the tumor), for example, by increasing levels of aspartate or alanine available to immune cells (e.g., for use in synthesis of protein and/or nucleotides in vivo). As a consequence, the levels, activation state, and/or cytotoxic capacity of immune cells, including activated T cells (e.g., CAR-T, Th1, and/or Th17 cells), in the tumor, the tumor microenvironment, or both are increased.

Immunotherapy refers to a diverse set of therapeutic strategies designed to induce a subject's own immune system to fight a condition or disease, such as cancer or infection (e.g., to induce a T cell response or an anti-tumor response to a condition or disease, such as cancer). Immunotherapy agents include antibodies, vaccines, cytokines and immune cell infusions. In some embodiments, immunotherapy (e.g., cancer immunotherapy) comprises a checkpoint inhibitor (e.g., a PD-1, PD-L1 or CTLA-4 checkpoint inhibitor). In some embodiments, immunotherapy (e.g., cancer immunotherapy) is a CAR-T therapy.

Cancer immunotherapy refers to a diverse set of therapeutic strategies designed to induce a subject's own immune system to fight a tumor. Cancer immunotherapy agents include antibodies that inhibit proteins expressed by cancer cells, vaccines and immune cell (e.g., T-cell) infusions. Antibody agents useful for promoting anti-tumor responses include anti-CTLA-4 antibodies (e.g., ipilimumab, tremelimumab), anti-PD-1 antibodies (e.g., nivolumab, pembrolizumab), anti-PD-L1 antibodies (e.g., avelumab), anti-PD-L2 antibodies, anti-TIM-3 antibodies, anti-LAG-3 antibodies, anti-OX40 antibodies and anti-GITR antibodies.

Immunological checkpoints regulate the immune system, and can inhibit an immune response to an immunologic stimulus upon stimulation (e.g., by cancer cells). "Checkpoint inhibitor," as used herein, refers to an inhibitor of an immunological checkpoint, typically, a protein. Examples of checkpoint inhibitors include agents (e.g., antibodies (for example, monoclonal antibodies), antibody fragments, peptides, fusion proteins) that bind to checkpoint proteins, such as, for example, CTLA4, PD1, PD2, PD-L1, PD-L2, B7-1, B7-1, LAG-3, TIM-3, KIRs, 4-IBB, 4-IBBL, TIGIT, galectin-9, GITR, GITRL, DR3, HVEM, TL1A, CD27, CD28, CD30, CD40, CD40L, CD80, CD86, CD96, nectin, OX-40, OX-40L, ICOS, CD155, CD226, CD258, CD272, and CD276.

The present invention also contemplates ex vivo engineering of immune cells to endow them with metabolic capacity to survive, activate, proliferate, and/or carry out immune effector functions in the presence of a nutrient-limited microenvironment (e.g., tumor microenvironment), such as by expressing one or more enzymes or transporters that produce an increase in the level of aspartate or alanine in the immune cells, for example, by expressing one or more enzymes that catalyze the reaction of asparagine and water into aspartate and ammonia or the reversible reaction between pyruvate and glutamate into alanine and ketoglutarate. In certain embodiments, the activity of such an enzyme may also limit tumor growth, for example, by consuming asparagine and thereby limiting its availability to tumor cells.

Accordingly, in certain embodiments, the invention relates to a method of promoting an immune response (e.g., a T cell response, an anti-tumor response) in a subject in need thereof, comprising administering to the subject a population of immune cells that express an enzyme or transporter that produces an increase in the level of aspartate or alanine in the immune cells (e.g., an effective amount of a population of immune cells that express an enzyme or transporter that produces an increase in the level of aspartate or alanine in the immune cells).

In certain embodiments, the invention relates to a method of enhancing an immunotherapy in a subject receiving the immunotherapy, comprising administering to the subject a population of immune cells that express an enzyme or transporter that produces an increase in the level of aspartate or alanine in the immune cells (e.g., an effective amount of a population of immune cells that express an enzyme or transporter that produces an increase in the level of aspartate or alanine in the immune cells).

In certain embodiments, the invention relates to a method of treating a cancer in a subject in need thereof, comprising administering to the subject a population of immune cells that express an enzyme or transporter that produces an increase in the level of aspartate or alanine in the immune cells (e.g., an effective amount of a population of immune cells that express an enzyme or transporter that produces an increase in the level of aspartate or alanine in the immune cells).

In some embodiments, the method comprises administering to the subject an effective amount of a population of immune cells that express an enzyme that produces an increase in the level of aspartate or alanine in the immune cells. For example, in some embodiments, the method comprises administering to the subject an effective amount of a population of immune cells that express an enzyme that produces an increase in the level of aspartate in the immune cells. In other embodiments, the method comprises administering to the subject an effective amount of a population of immune cells that express an enzyme that produces an increase in the level of alanine in the immune cells.

In some embodiments, the method comprises administering to the subject an effective amount of a population of immune cells that express a transporter that produces an increase in the level of aspartate or alanine in the immune cells. For example, in some embodiments, the method comprises administering to the subject an effective amount of a population of immune cells that express a transporter that produces an increase in the level of aspartate in the immune cells. In other embodiments, the method comprises administering to the subject an effective amount of a population of immune cells that express a transporter that produces an increase in the level of alanine in the immune cells.

As used herein, "enzyme" refers to a protein involved in the catalysis of one or more substrates into one or more products. Enzymes include asparaginase, which catalyzes the reaction of asparagine and water into aspartate and ammonia, and alanine aminotransferase, which catalyzes the reversible reaction between pyruvate and glutamate into alanine and ketoglutarate. In one embodiment, the enzyme is asparaginase. In another embodiment, the enzyme is alanine aminotransferase.

As used herein, "transporter" refers to an integral transmembrane protein involved in the movement of one or more substances across the membrane the protein spans. In some embodiments, a transporter is involved in the movement of one or more substances across the plasma membrane into the cell (e.g., the transporter enables cellular uptake of a substance). Transporters include alanine serine cysteine transporter 2 (ASCT2), which transports neutral amino acids, such as alanine and glutamine, into cells, and excitatory amino acid transporter 1 (EAAT1), which transports aspartic acid into cells.

In some embodiments, the invention relates to a method of promoting an immune response (e.g., a T cell response, an anti-tumor response) in a subject in need thereof, comprising administering to the subject a population of immune cells that express an enzyme (e.g., asparaginase) that catalyzes the formation of aspartate from asparagine (e.g., an effective amount of a population of immune cells that express an enzyme (e.g., asparaginase) that catalyzes the formation of aspartate from asparagine).

In some embodiments, the invention relates to a method of enhancing an immunotherapy in a subject receiving the immunotherapy, comprising administering to the subject a population of immune cells that express an enzyme (e.g., asparaginase) that catalyzes the formation of aspartate from asparagine (e.g., an effective amount of a population of immune cells that express an enzyme (e.g., asparaginase) that catalyzes the formation of aspartate from asparagine).

In some embodiments, the invention relates to a method of treating a cancer in a subject in need thereof, comprising administering to the subject a population of immune cells that express an enzyme (e.g., asparaginase) that catalyzes the formation of aspartate from asparagine (e.g., an effective amount of a population of immune cells that express an enzyme (e.g., asparaginase) that catalyzes the formation of aspartate from asparagine).

In certain embodiments, the invention relates to a method of promoting an immune response in a subject in need thereof that comprises administering to a subject an enzyme (e.g., asparaginase) that catalyzes the production of aspartate from asparagine (e.g., by hydrolysis of asparagine into aspartate and ammonium) in immune cells in the subject and/or an exogenous transporter that enables enhanced cellular uptake of alanine, aspartate, or asparagine. In some embodiments, a population of immune cells that express an enzyme that catalyzes the production of aspartate (or an exogenous transporter that enables uptake of a desired amino acid) is administered to the subject. In some embodiments, the immune cells comprise or consist essentially of CAR-T cells. In some embodiments, the immune cells consist of CAR-T cells.

Immune cells are cells involved in the immune system. Immune cells include B cells and T cells. B cells have the ability to recognize unique antigens through surface immunoglobin (Ig) molecules. Naïve B cells exit the bone marrow, transit the vasculature and encounter antigen in secondary lymphoid organs, such as the spleen or lymph node. Antigen binding promotes proliferation and differentiation. Like B cells, T cells have the ability to recognize unique antigens. However, instead of a surface Ig, they express a T cell receptor (TCR) complex on their cell surfaces. Antigens are processed by antigen-presented cells, and presented in association with the major histocompatibility complex (MHC). In some embodiments, the immune cells are T cells (e.g., CAR-T cells). In some embodiments, the immune cells are anti-cancer immune cells.

As used herein, "anti-cancer immune cells" refers to immune cells that recognize an antigen(s) on tumor cells. Tumor antigens include those described herein. An example of an anti-cancer immune cell is a CAR-T cell designed to recognize an antigen(s) (e.g., mesothelin) on tumor cells.

In a particular embodiment, the enzyme is asparaginase. The asparaginase can be exogenous or endogenous, naturally-occurring or non-naturally-occurring (e.g., engineered). The asparaginase can be isolated (e.g., from a natural source), recombinant or synthetic. Examples of asparaginases from a variety of organisms that are suitable for use in the methods and compositions described herein are known in the art. In a particular embodiment, the asparaginase is an asparaginase from guinea pig (gpASNase1) (see Sullivan, L. B., et al., Nat. Cell Biol. 2018 July;20(7):782-788, the contents of which are incorporated by reference herein in their entirety), for example, having the sequence of SEQ ID NO:1. In other embodiments, the asparaginase is from a yeast, such as S. cerevisiae (for example, an asparaginase corresponding to those described under UniProt Accession Nos. POCZ17, POCX79, POCX77, POCX78 and P38986), or bacteria, such as E. coli (for example, an asparaginase corresponding to those described under UniProt Accession Nos. P00805, P0A962 and P0A963). In yet other embodiments, the asparaginase is from a mammal, such as a human (for example, an asparaginase corresponding to that described under UniProt Accession No. Q7L266).

Examples of other asparaginases that are suitable for use in the methods and compositions of the invention include variants of naturally-occurring asparaginases (e.g., variants having at least about 80%, about 85%, about 90%, about 95%, about 98%, or about 99% amino acid sequence identity to a naturally-occurring asparaginase, such as a naturally-occurring (e.g., wild-type) asparaginase from *E. coli* or guinea pig. In some embodiments, variants of naturally-occurring asparaginases include enzymes that have been engineered to have reduced immunogenicity in a host organism (e.g., a human subject). In some embodiments, the enzyme catalyzing the production of aspartate from asparagine is an enzyme from a human or a variant thereof, e.g., ASPG or ASRGL1. In some embodiments, the human enzyme is engineered to alter subcellular localization, enhance its catalytic activity for the desired reaction, and/or decrease its catalytic activity for one or more desired reactions. Methods of engineering proteins (e.g., enzymes) for reduced immunogenicity in a host organism, altered subcellular localization, or altered catalytic activity are well-known in the art.

As used herein, the term "sequence identity" means that two nucleotide or amino acid sequences, when optimally aligned, such as by the programs GAP or BESTFIT using default gap weights, share at least, e.g., 70% sequence identity, or at least 80% sequence identity, or at least 85% sequence identity, or at least 90% sequence identity, or at least 95% sequence identity or more. For sequence comparison, typically one sequence acts as a reference sequence (e.g., parent sequence), to which test sequences are compared. The sequence identity comparison can be examined throughout the entire length of a given protein, or within a desired fragment of a given protein. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., Current Protocols in Molecular Biology). One example of an algorithm that is suitable for determining percent sequence identity and sequence similarity is the BLAST algorithm, which is described in Altschul et al., J. Mol. Biol. 215:403 (1990). Software for performing BLAST analyses is publicly available through the National Center for Biotechnology Information (publicly accessible through the National Institutes of Health NCBI internet server). Typically, default program parameters can be used to perform the sequence comparison, although customized parameters can also be used. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89:10915 (1989)).

In certain embodiments, the asparaginase is a naturally-occurring asparaginase or a variant of a naturally-occurring asparaginase having at least about 80% amino acid sequence identity to a naturally-occurring asparaginase.

In specific embodiments, the asparaginase comprises, consists essentially of or consists of the sequence of SEQ ID NO:1.

Asparaginases can be unmodified or modified (e.g., post-translationally modified), and/or unlabeled or labeled (e.g., with a detectable label, such as a fluorophore or hapten). In certain embodiments, an asparaginase is coupled (e.g., covalently linked) to one or more additional molecules (e.g., an enzyme that consumes aspartate for nucleotide or protein synthesis or a transporter for asparagine). In a particular embodiment, the asparaginase is coupled to an aspartate transcarbamoylase enzyme, such as CAD, or an aspartate tRNA synthetase enzyme.

An asparaginase and/or other desired protein(s) can be introduced into immune cells as a protein, or as a nucleic acid molecule that encodes the asparaginase or other protein, using well-known techniques, including any of the various techniques described herein. Thus, cells (e.g., immune cells) in a population of cells described herein (e.g., a population of cells in a method or composition described herein) may comprise (e.g., express) a desired protein (e.g., an enzyme or transporter that produces an increase in the level of aspartate or alanine in immune cells; an enzyme that catalyzes the formation of aspartate from asparagine or the formation of alanine from pyruvate and glutamate; asparaginase), a nucleic acid that encodes the desired protein, or the desired protein and a nucleic acid that encodes the desired protein. In a particular embodiment, an asparaginase is introduced (e.g., transfected) into immune cells as a nucleic acid molecule that encodes the asparaginase. Suitable nucleic acid constructs for introduction into cells are known in the art and include the various nucleic acid constructs described herein. In an embodiment, the nucleic acid molecule that encodes the asparaginase is a DNA expression vector (e.g., a viral vector, a non-viral vector).

In some embodiments, an asparaginase is selectively expressed in mitochondria of the immune cells. Mitochondrial expression of immune cells can be achieved, for example, by fusing a mitochondrial localization tag to the coding sequence of a gene of interest (e.g., gene for asparaginase) in a lentiviral plasmid.

In some embodiments, an asparaginase is selectively expressed in the cytosol of the immune cells. The cytosol is the canonical cellular localization for asparaginase.

In some embodiments, an asparaginase is selectively expressed in a degradative compartment such as a lysosome of the immune cells. Expression in a degradative compartment, such as a lysosome, of immune cells can be achieved, for example, by including a consensus motif in the coding region of a plasmid that redirects intracellular localization to the lysosome.

In certain embodiments, the asparaginase, or an encoding nucleic acid molecule, is introduced (e.g., transfected) into immune cells ex vivo (e.g., into an ex vivo population of immune cells), e.g., by transfection, transduction, transformation, infection. In a particular embodiment, the asparaginase, or an encoding nucleic acid molecule, is introduced into a population of T cells. In some embodiments, the T cells are chimeric antigen receptor T cells (CAR-T cells).

CARs are artificial receptors that are engineered to contain an immunoglobulin antigen binding domain, such as a single-chain variable fragment (scFv). Typically, antigen recognition occurs through an antibody-based single chain variable fragment that is fused to the CD3zeta chain of a TCR. CAR-T cells therefore combine the specificity of an antibody with the cytolytic activity of a T cell. A CAR may, for example, comprise an scFv fused to a TCR CD3 transmembrane region and endodomain. An scFv is a fusion protein of the variable regions of the heavy ($V_H$) and light ($V_L$) chains of immunoglobulins, which may be connected with a short linker peptide of approximately 10 to 25 amino acids (Huston J. S. et al., Proc. Natl. Acad. Sci. USA 1988; 85(16):5879-5883). The linker may be glycine-rich for flexibility, and serine- or threonine-rich for solubility, and may connect the N-terminus of the $V_H$ to the C-terminus of the $V_L$, or visa versa. The scFv may be preceded by a signal peptide to direct the protein to the endoplasmic reticulum and, subsequently, the T cell surface. In the CAR, the scFv may be fused to a TCR transmembrane and endodomain. A flexible spacer may be included between the scFv and the TCR transmembrane domain to allow for variable orientation and antigen binding. The endodomain is the functional signal-transmitting domain of the receptor. An endodomain of a CAR may comprise, for example, intracellular signalling domains from the CD3 ζ-chain, or from receptors such as CD28, 41BB, or ICOS. A CAR may comprise multiple signalling domains, for example, but not limited to, CD3z-CD28-41BB and CD3z-CD28-OX40.

The CAR-T cells can be designed to recognize an antigen(s) on tumor cells. Tumor antigens expressed by cancer cells include, for example, cancer-testis (CT) antigens encoded by cancer-germ line genes, such as MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, GAGE-I, GAGE-2, GAGE-3, GAGE-4, GAGE-5, GAGE-6, GAGE-7, GAGE-8, BAGE-I, RAGE-1, LB33/MUM-1, PRAME, NAG, MAGE-Xp2 (MAGE-B2), MAGE-Xp3 (MAGE-B3), MAGE-Xp4 (MAGE-B4), MAGE-C1/CT7, MAGE-C2, NY-ESO-I, LAGE-I, SSX-I, SSX-2(HOM-MEL-40), SSX-3, SSX-4, SSX-5, SCP-I and XAGE, and immunogenic fragments thereof (Simpson et al., Nature Rev. (2005) 5, 615-625; Gure et al., Clin Cancer Res (2005) 11, 8055-8062; Velazquez et al., Cancer Immun. (2007) 7, 11; Andrade et al., Cancer Immun. (2008) 8, 2; Tinguely et al., Cancer Science (2008); Napoletano et al., Am. J. of Obstet. Gyn. (2008) 198, 99 e91-97).

Other tumor antigens include, for example, overexpressed, upregulated or mutated proteins and differentiation antigens, particularly melanocyte differentiation antigens such as p53, ras, CEA, MUC1, PMSA, PSA, tyrosinase, Melan-A, MART-1, gp100, gp75, alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-A11, hsp70-2, KIAAO205, Mart2, Mum-2, and 3, neo-PAP, myosin class I, OS-9, pml-RAR.alpha. fusion protein, PTPRK, K-ras, N-ras, triosephosphate isomerase, GnTV, Herv-K-mel, NA-88, SP17, and TRP2-Int2, (MART-I), E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, alpha.-fetoprotein, 13HCG, BCA225, BTAA, CA 125, CA 15-3 (CA 27.29\BCAA), CA 195, CA 242, CA-50, CAM43, CD68\KP1, CO-029, FGF-5, G250, Ga733 (EpCAM), HTgp-175, M344, MA-50, MG7-Ag, MOV18, NB\170K, NY-CO-1, RCAS1, SDCCAG16, TA-90 (Mac-2 binding protein\cyclophilin C-associated protein), TAAL6, TAG72, TLP, TPS and tyrosinase-related proteins, such as TRP-1 and TRP-2.

Other tumor antigens include out-of-frame peptide-MHC complexes generated by the non-AUG translation initiation mechanisms employed by "stressed" cancer cells (Malarkannan et al., Immunity 1999 June; 10(6):681-90).

Yet other tumor antigens, as well as their associated indication(s) are listed in the table below:

| Antigen | Indication | Reference |
|---|---|---|
| CD19 | B-cell malignancies | Porter et al., 2011 |
| CD20 | " | Rufener et al., 2016 |
| CD22 | " | Fry et al., 2018 |
| CD123 | AML | Ruella et al., 2016 |
| CD33 | " | Kenderian et al., 2016 |
| BCMA | Multiple Myeloma | Ali et al., 2016 |
| CS1 | " | Chu et al., 2014 |
| Kappa Light Chain | " | Ramos et al., 2016 |
| CD138 (Syndecan 1) | " | Tian et al., 2017 |
| MUC1 glycan | "Universal solid tumor antigen" | Posey et al., 2016 |
| ERBB2 | Ovarian, breast, GBM, osteosarcoma | Liu et al., 2016 |
| Mesothelin | Pancreatic, Mesothelioma | Beatty et al., 2018 |
| Fibroblast activating protein (FAP) | Mesothelioma, lung, colon, pancreatic | Wang et al., 2014 |
| Folate Receptor-alpha | Ovarian cancer | Kandalaft et al., 2012 |
| GD-2 | Neuroblastoma | Richman et al., 2018 |
| PSMA | Prostate cancer | Kloss et al., 2018 |
| EGFR | NSCLC, epithelial carcinoma, glioma | Golubovskaya et al., 2018 |
| EGFRv111 | GBM | O'Rourke et al., 2017 |
| CAIX | Renal Cell carcinoma (RCC) | Lamers et al., 2013 |
| CEACAM | Lung, colon, pancreatic | Burga et al., 2015 |
| CD70 | Head and neck squamous cell carcinoma | Park et al., 2018 |

Other tumor antigens are well-known in the art (see, for example WO00/20581; Cancer Vaccines and Immunotherapy (2000) Eds. Stern, Beverley and Carroll, Cambridge University Press, Cambridge). The sequences of these tumor antigens are readily available from public databases, but are also found in WO 1992/020356 A1, WO 1994/005304 A1, WO 1994/023031 A1, WO 1995/020974 A1, WO 1995/023874 A1 and WO 1996/026214 A1.

In some embodiments, the CAR-T cells are designed to recognize and/or recognize a solid tumor antigen, for example, mesothelin, EGFR, EGFRvIII, folate receptor alpha, Muc1, or Her-2. The Her-2 antigen can be associated with breast, ovarian, bladder, pancreatic or stomach cancer (e.g., breast cancer, especially Her-2-positive breast cancer).

Methods of obtaining and/or preparing populations of T cells, including CAR-T cells, are known in the art. For example, primary human T cells can be isolated from peripheral blood using RosetteSep (Stem Cell Technologies) column purification technology (see, for example, O'Connor, R. S., et al., J. Immunol. 2012 Aug. 1; 189(3): 1330-1339).

Cells (e.g., immune cells) that express an enzyme or transporter (e.g., enzyme), can be administered to a subject in need thereof by a variety of routes of administration including, for example, oral, dietary, topical, transdermal, rectal, parenteral (e.g., intra-arterial, intravenous, intramuscular, subcutaneous injection, intradermal injection), intravenous infusion and inhalation (e.g., intrabronchial, intranasal or oral inhalation, intranasal drops) routes of administration, depending, for example, on the cells and the particular disease (e.g., cancer) to be treated. Typically, cells are administered to a subject in need thereof by injection, including intravenous, intrathecal, intraperitoneal, intraspinal, intracerebral, spinal and intrasternal injection, or infusion. Methods for administering a population of immune cells (e.g., an ex vivo population), such as CAR-T cells, to a subject are well-known in the art.

Administration can be local or systemic as indicated. The actual dose of a cellular or other therapeutic agent and treatment regimen can be determined by a skilled physician, taking into account, for example, the nature of the condition being treated, and patient characteristics.

As used herein, "subject" refers to a mammal (e.g., human, such as an aged human (e.g., a human aged 60 or greater, 65 or greater, or greater than 65), non-human primate, cow, sheep, goat, horse, dog, cat, rabbit, guinea pig, rat, mouse). In a particular embodiment, the subject is a human.

A "subject in need thereof" refers to a subject (e.g., patient) who has a disease or condition that can be treated by an immunotherapy.

"A subject receiving an immunotherapy" refers to a subject being treated for a disease or condition (e.g., cancer) with an immunotherapy (e.g., a cancer immunotherapy). In methods involving subjects receiving an immunotherapy, the immunotherapy can be administered before, after or concurrently with the cells and/or compositions described herein. When co-administered simultaneously (e.g., concurrently), the cells and/or compositions described herein and immunotherapy can be in separate formulations or the same formulation. Alternatively, the cells and/or compositions described herein and immunotherapy can be administered sequentially, as separate compositions. In methods of enhancing immunotherapy in a subject receiving an immunotherapy described herein, the cells and/or compositions described herein and the immunotherapy should be administered within an appropriate time frame to allow enhancement of the immunotherapy.

"An effective amount" is an amount effective, at dosages and for periods of time necessary, to achieve a desired therapeutic result (e.g., treatment, healing, inhibition or amelioration of physiological response or condition, etc.). The full therapeutic effect does not necessarily occur by administration of one dose, and may occur only after administration of a series of doses. Thus, a therapeutically effective amount may be administered in one or more administrations. A therapeutically effective amount may vary according to factors such as disease state, age, sex, and weight of a subject, mode of administration and the ability of a therapeutic agent, or combination of therapeutic agents, to elicit a desired response in an subject.

An effective amount of an agent to be administered can be determined by a clinician of ordinary skill using the guidance provided herein and other methods known in the art. For example, suitable dosages can be from about $10^4$ cells/kg to about $10^9$ cells/kg, for example, from about $10^5$ cells/kg to about $10^8$ cells/kg, from about $10^5$ cells/kg to about $10^6$ cells/kg, from about $10^6$ cells/kg to about $10^8$ cells/kg or from about $10^7$ cells/kg to about $10^8$ cells/kg, body weight per treatment. Determining the dosage for a particular agent, subject and disease is well within the abilities of one of skill in the art. Preferably, the dosage does not cause or produces minimal adverse side effects.

As used herein, the term "promoting an immune response" means to support (e.g., enhance) a subject's immune response, e.g., to an infection, tumor. Evidence that an agent(s) is promoting an immune response includes increased levels, activation and/or cytotoxic capacity of immune cells, e.g., in a tumor, tumor microenvironment or both.

As used herein, the term "enhancing an immunotherapy" means to improve (e.g., improve the therapeutic efficacy of) an immunotherapy. Evidence that an agent(s) is enhancing an immunotherapy includes increased levels, activation and/or cytotoxic capacity of immune cells, e.g., in a tumor, tumor microenvironment or both, as compared to the levels, activation and/or cytotoxic capacity of immune cells in the absence of the disclosed method.

As used herein, the terms "treat," "treating," or "treatment," mean to take steps to deliver a therapy to a subject in need thereof, and includes counteracting a medical condition (e.g., a condition related to cancer) to the extent that the medical condition is improved according to a clinically-acceptable standard (e.g., reduction in tumor formation, size, growth or metastasis), and relieving the symptoms resulting from the medical condition.

In an embodiment, the subject in need thereof has cancer. The cancer can be a solid tumor, a leukemia, a lymphoma or a myeloma. In particular embodiments, the subject in need thereof has a solid tumor, such as a breast tumor, a colon tumor, a lung tumor, a pancreatic tumor, a prostate tumor, a bone tumor, a skin tumor (e.g., melanoma, squamous cell carcinoma), a brain tumor, a head and neck tumor, a lymphoid tumor, or a liver tumor. In particular embodiments, the subject in need thereof has a solid tumor, such as a breast tumor, an ovarian tumor, a colon tumor, a lung tumor, a pancreatic tumor, a prostate tumor, a bone tumor, a skin tumor (e.g., melanoma, squamous cell carcinoma), a brain tumor, a head and neck tumor, a lymphoid tumor, or a liver tumor. In certain embodiments, the subject has a solid tumor having one or more features selected from poor perfusion, a low $NAD^+/NADH$ ratio, a low oxygen ($O_2$) level, a high lactate level, a low aspartate level, a low alanine level, a low asparagine level, or a high asparagine level. In some embodiments, the subject has a metastatic cancer, such as a metastatic lung cancer Exemplary cancers include: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood; Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer;

Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's, Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Mantle Cell Lymphoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood; Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macroglobulinemia; and Wilms' Tumor.

Metastases of the aforementioned cancers can also be treated in accordance with the methods described herein.

In some embodiments, the cancer is a solid tumor. In more specific embodiments, the cancer is pancreatic cancer, mesothelioma, non-small cell lung cancer (NSCLC), epithelial carcinoma, glioma, glioblastoma, ovarian cancer, breast cancer, bladder cancer, pancreatic cancer or stomach cancer.

The cells (e.g., immune cells) and/or compositions described herein can also be administered in combination with one or more other therapies (e.g., a chemotherapy, such as a chemotherapeutic agent; an immunotherapy, such as an immunotherapy agent or immunomodulatory compound). When administered in a combination therapy, the cells and/or compositions described herein can be administered before, after or concurrently with the other therapy (e.g., an additional therapeutic agent(s)). When co-administered simultaneously (e.g., concurrently), the cells and/or compositions described herein and other therapy can be in separate formulations or the same formulation. Alternatively, the cells and/or compositions described herein and other therapy can be administered sequentially, as separate compositions, within an appropriate time frame as determined by a skilled clinician (e.g., a time sufficient to allow an overlap of the pharmaceutical effects of the therapies).

In some embodiments, the methods further comprise administering one or more additional therapies (e.g., therapeutic agents) to the subject (e.g., a chemotherapeutic agent, for example, paclitaxel, doxorubicin, 5-fluorouracil, tamoxifen, octreotide and/or an immunomodulatory compound, for example, an antibody against targets such as PD-1, PD-L1, or CTLA-4). In some embodiments, the one or more additional therapeutic agents comprises a cancer immunotherapy agent, for example, a checkpoint inhibitor (e.g., a PD-1, PD-L1 or CTLA-4 checkpoint inhibitor).

Compositions Comprising Populations of Immune Cells

In some embodiments, the present invention provides compositions (e.g., pharmaceutical compositions) comprising a population (e.g., ex vivo population) of immune cells that express an enzyme or transporter that produces an increase in the level of aspartate or alanine in the immune cells.

In some embodiments, the composition comprises a population of immune cells that express an enzyme that produces an increase in the level of aspartate or alanine in the immune cells. For example, in some embodiments, the composition comprises a population of immune cells that express an enzyme that produces an increase in the level of aspartate in the immune cells. In other embodiments, the composition comprises a population of immune cells that express an enzyme that produces an increase in the level of alanine in the immune cells.

In some embodiments, the composition comprises a population of immune cells that express a transporter that produces an increase in the level of aspartate or alanine in the immune cells. For example, in some embodiments, the composition comprises a population of immune cells that express a transporter that produces an increase in the level of aspartate in the immune cells. In other embodiments, the composition comprises a population of immune cells that express a transporter that produces an increase in the level of alanine in the immune cells.

In some embodiments, the present invention provides a composition (e.g., pharmaceutical composition) comprising a population (e.g, ex vivo population) of immune cells that express an enzyme that catalyzes the formation of aspartate from asparagine or the formation of alanine from pyruvate and glutamate.

In additional embodiments, the present invention provides compositions (e.g., pharmaceutical compositions) comprising a population (e.g., ex vivo population) of immune cells expressing an enzyme that catalyzes the production of aspartate from asparagine.

The compositions can be used in the methods described herein, e.g., to supply a population of immune cells to a subject in need thereof.

"Population," as used herein, refers to a group of cells (e.g., immune cells) that share a common type, but are not necessarily identical to one another (e.g., genetically, phenotypically). For example, it will be understood by a person of ordinary skill in the art that in a population of CAR-T cells prepared using traditional methods of preparing populations of CAR-T cells, some of the cells will express the CAR, and some will not. Lentiviral infection efficiencies, for example, can vary from about 50% to 100%. "Population," as used herein, includes such populations. Thus, in some embodiments, a population of cells is a non-clonal population. In some embodiments, a population of cells is a clonal population. In some embodiments, at least 50%, at least 60%, at least 70%, at least 75%, at least 80%, at least 85%, at least 90%, at least 95%, at least 98%, or at least 99% of the cells in the population are identical.

In a particular embodiment, the enzyme is an asparaginase described herein (e.g., an asparaginase from bacteria, yeast, a non-human mammal, such as a guinea pig or a human, a variant of a naturally-occurring asparaginase that has been engineered for reduced immunogenicity in a human subject). In an embodiment, the asparaginase is coupled to an asparagine transporter.

In an embodiment, the immune cells in the population include T cells (e.g., human T cells). The T cells can be cultured or uncultured. Methods of obtaining and/or preparing populations of T cells are known in the art.

In a particular embodiment, the immune cells are chimeric antigen receptor T cells (CAR-T cells). In a further embodiment, the CAR-T cells are designed to recognize and/or recognize an antigen on tumor cells, such as an antigen described herein (e.g., mesothelin, EGFR, EGFRvIII, folate receptor alpha, Muc1 and/or Her-2). Suitable methods of obtaining and/or preparing populations of CAR-T cells are known in the art.

In some embodiments, the population (e.g., ex vivo population) of immune cells is in a culture medium or other carrier. Thus, in some embodiments, the composition further comprises a carrier, such as a pharmaceutically acceptable carrier.

"Pharmaceutically acceptable carrier," as used herein, refers to a non-toxic carrier or excipient that does not destroy the pharmacological activity of the agent with which it is formulated and is nontoxic when administered in doses sufficient to deliver a therapeutic amount of the agent. Pharmaceutically acceptable carriers that may be used in the compositions described herein include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions described herein may be administered orally, parenterally (including subcutaneously, intramuscularly, intravenously and intradermally), by inhalation spray, topically, rectally, nasally, buccally, vaginally or via an implanted reservoir. Typically, compositions described herein may be administered by injection, including intravenous, intrathecal, intraperitoneal, intraspinal, intracerebral, spinal and intrasternal injection, or infusion. For example, compositions described herein can be administered by injection, e.g., directly into a tumor, lymph node or site of infection.

The term "parenteral," as used herein, includes subcutaneous, intracutaneous, intravenous, intramuscular, intraocular, intravitreal, intra-articular, intra-arterial, intra-synovial, intrasternal, intrathecal, intralesional, intrahepatic, intraperitoneal intralesional and intracranial injection or infusion techniques. Preferably, the compositions are administered subcutaneously, intraperitoneally or intravenously.

Compositions described herein for intravenous, subcutaneous, or intraperitoneal injection may contain an isotonic vehicle such as sodium chloride injection, Ringer's injection, dextrose injection, dextrose and sodium chloride injection, lactated Ringer's injection, or other vehicles known in the art. Other carriers suitable for compositions for subcutaneous, intraperitoneal or intravenous delivery include culture media and/or serum (e.g., human serum).

The compositions can also be in the form of a sterile injectable preparation, for example, as a sterile injectable aqueous or oleaginous suspension. This suspension can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium. For this purpose, any bland fixed oil can be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms can also be used for the purposes of formulation.

Compositions provided herein can be orally administered in any orally acceptable dosage form including, but not limited to, capsules, aqueous suspensions, dispersions and solutions. When aqueous suspensions and/or emulsions are required for oral use, the active ingredient can be suspended or dissolved in an oily phase and combined with emulsifying and/or suspending agents. If desired, certain sweetening, flavoring or coloring agents may also be added.

In some embodiments, an oral formulation is formulated for immediate release or sustained/delayed release.

Liquid dosage forms for oral administration include pharmaceutically acceptable emulsions, microemulsions, solutions, suspensions, syrups, and elixirs. In addition to the cells (e.g., immune cells) of the present disclosure, the liquid dosage forms may contain inert diluents commonly used in the art, such as water or other solvents, solubilizing agents and emulsifiers, such as ethyl alcohol (ethanol), isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, or mixtures thereof. Besides inert diluents, the oral compositions can also include adjuvants such as wetting agents, emulsifying and suspending agents, sweetening, flavoring, coloring, perfuming, and preservative agents.

Compositions for oral administration may be designed to protect the active ingredient against degradation as it passes through the alimentary tract, for example, by an outer coating of the formulation on a capsule.

In another embodiment, compositions can be provided in an extended (or "delayed" or "sustained") release composition. This delayed-release composition comprises the cells in combination with a delayed-release component. Such a composition allows targeted release of a provided agent(s) into the lower gastrointestinal tract, for example, into the small intestine, the large intestine, the colon and/or the rectum. In certain embodiments, a delayed-release composition further comprises an enteric or pH-dependent coating, such as cellulose acetate phthalates and other phthalates (e.g., polyvinyl acetate phthalate, methacrylates (Eudragits)). Alternatively, the delayed-release composition provides controlled release to the small intestine and/or colon by the provision of pH sensitive methacrylate coatings, pH sensitive polymeric microspheres, or polymers which undergo degradation by hydrolysis. The delayed-release composition can be formulated with hydrophobic or gelling excipients or coatings. Colonic delivery can further be provided by coatings which are digested by bacterial enzymes such as amylose or pectin, by pH dependent polymers, by hydrogel plugs swelling with time (Pulsincap), by time-dependent hydrogel coatings and/or by acrylic acid linked to azoaromatic bonds coatings.

Compositions can also be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, fluorocarbons, and/or other conventional solubilizing or dispersing agents.

The amount of cells described herein that can be combined with the carrier materials to produce a composition in a single dosage form will vary depending upon the host treated, the particular mode of administration and the activity of the agent(s) employed. Preferably, compositions should be formulated so that a dosage of from about $10^4$ cells/kg to about $10^9$ cells/kg, for example, from about $10^5$ cells/kg to about $10^8$ cells/kg, from about $10^5$ cells/kg to about $10^6$ cells/kg, from about $10^6$ cells/kg to about $10^8$ cells/kg or from about $10^7$ cells/kg to about $10^8$ cells/kg, body weight, of the agent can be administered to a subject receiving the composition.

The desired dose may conveniently be administered in a single dose or as multiple doses administered at appropriate intervals such that, for example, the agent(s) is administered 2, 3, 4, 5, 6 or more times per day. Alternatively, the daily dose can be administered as an infusion (e.g., a continuous infusion).

The amount of active ingredient that can be combined with a carrier material to produce a single dosage form will vary depending upon the host treated and the particular mode of administration. A typical preparation will contain from about 5% to about 95% cells (w/w). Alternatively, a preparation can contain from about 20% to about 80% cells (w/w).

Doses lower or higher than those recited above may be required. Specific dosage and treatment regimens for any particular subject will depend upon a variety of factors, including the activity of the specific agent employed, the age, body weight, general health status, sex, diet, time of administration, rate of excretion, drug combination, the severity and course of the disease, condition or symptoms, the subject's disposition to the disease, condition or symptoms, and the judgment of the treating physician. The amount of cells in the composition will also depend upon the particular cells in the composition.

Other pharmaceutically acceptable carriers, adjuvants and vehicles that can be used in the compositions of this invention include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives can also be advantageously used to enhance delivery of agents described herein.

In certain embodiments, the immune cells in the population comprise a nucleic acid molecule (e.g., plasmid), or nucleic acid sequence insertion in the immune cell genome, that encodes an enzyme (e.g., an asparaginase) that catalyzes the formation of aspartate from asparagine. Methods of introducing nucleic acid molecules into cells (e.g., immune cells) are well-known in the art and include the methods and techniques described herein (e.g., transfection). Methods for modulating the immune cell genome are also well-known in the art, including via use of CRISPR-Cas9. In an embodiment, the nucleic acid molecule that encodes an enzyme that catalyzes the formation of aspartate from asparagine (e.g., an asparaginase) is a DNA expression vector (e.g., a plasmid). The DNA expression vector can be a viral vector, such as a lentiviral vector, or a non-viral vector.

In some embodiments, the compositions of the invention include one or more additional therapeutic agents (e.g., a chemotherapeutic agent, for example, paclitaxel, doxorubicin, 5-fluorouracil, tamoxifen, octreotide, and/or an immunomodulatory compound, for example, an antibody against targets such as PD-1, PD-L1, or CTLA-4). In some embodiments, the one or more additional therapeutic agents comprises a checkpoint inhibitor (e.g., a PD-1, PD-L1 or CTLA-4 checkpoint inhibitor). Other examples of additional therapeutic agents include immunotherapy agents, or immunomodulatory compounds, including cancer immunotherapy agents, described herein.

Also provided herein is a kit comprising cells (e.g., immune cells) described herein and an additional agent(s) (e.g., therapeutic agent(s)). In some embodiments, the kit further comprises written instructions for administering the cells and the additional agent(s) to a subject to treat a medical condition described herein (e.g., cancer).

Standard pharmaceutical formulation techniques can be employed, such as those described in Remington's Pharmaceutical Sciences, Mack Publishing Company, Easton, PA.

Unless defined otherwise, all technical and scientific terms used herein have the same meaning as commonly understood by one of ordinary skill in the art (e.g., in cell culture, molecular genetics, nucleic acid chemistry, hybridization techniques and biochemistry). Standard techniques are used for molecular, genetic and biochemical methods (see generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) $4_{th}$ Ed, John Wiley & Sons, Inc., which are incorporated herein by reference) and chemical methods.

As used herein, the singular forms "a," "an" and "the" include plural referents unless the context clearly dictates otherwise. Thus, for example, reference to "an agent" can include a plurality of agents. Further, the plurality can comprise more than one of the same agent or a plurality of different agents.

Exemplication

Cloning Strategy

A nucleic acid molecule encoding guinea pig asparaginase (SEQ ID NO:1) was digested with Xba1 and BSPE1. The asparaginase open-reading frame (ORF) thus obtained was inserted into a lentiviral expression plasmid designed to co-express guinea pig asparaginase and an anti-mesothelin CAR comprising SS1 scFV, CD8 hinge/transmembrane, CD28 intracellular signaling domain and CD3ζ chain. FIG. 1 is a partial vector map of the resulting plasmid, and shows the lentiviral CAR construct designed to co-express guinea pig asparaginase and the anti-mesothelin CAR. The sequence of the resulting plasmid is shown in SEQ ID NO:2.

$^{13}$C Asparagine Tracer

A $^{13}$C asparagine tracer was used to determine whether the asparaginase construct was working effectively. Primary human T cells were activated with DYNABEADS®. After overnight stimulation, the cells were lentivirally infected with the lentiviral CAR construct of SEQ ID NO:2 or a lentiviral CAR construct lacking an asparaginase coding sequence. The infected cells were expanded for nine days, then switched to an RPMI 1640 medium lacking aspartate and asparagine, and supplemented with 1 mM $^{13}$C asparagine, 10% dialyzed FBS and 1% HEPES for 2 hours before being harvested for analysis by LC/MS. Nontransduced (NTD) T cells were used as negative controls and compared to SS1.28Z (28z) or SS1.28Z engineered to co-express asparaginase (28z-Asparaginase).

Figure 2A:
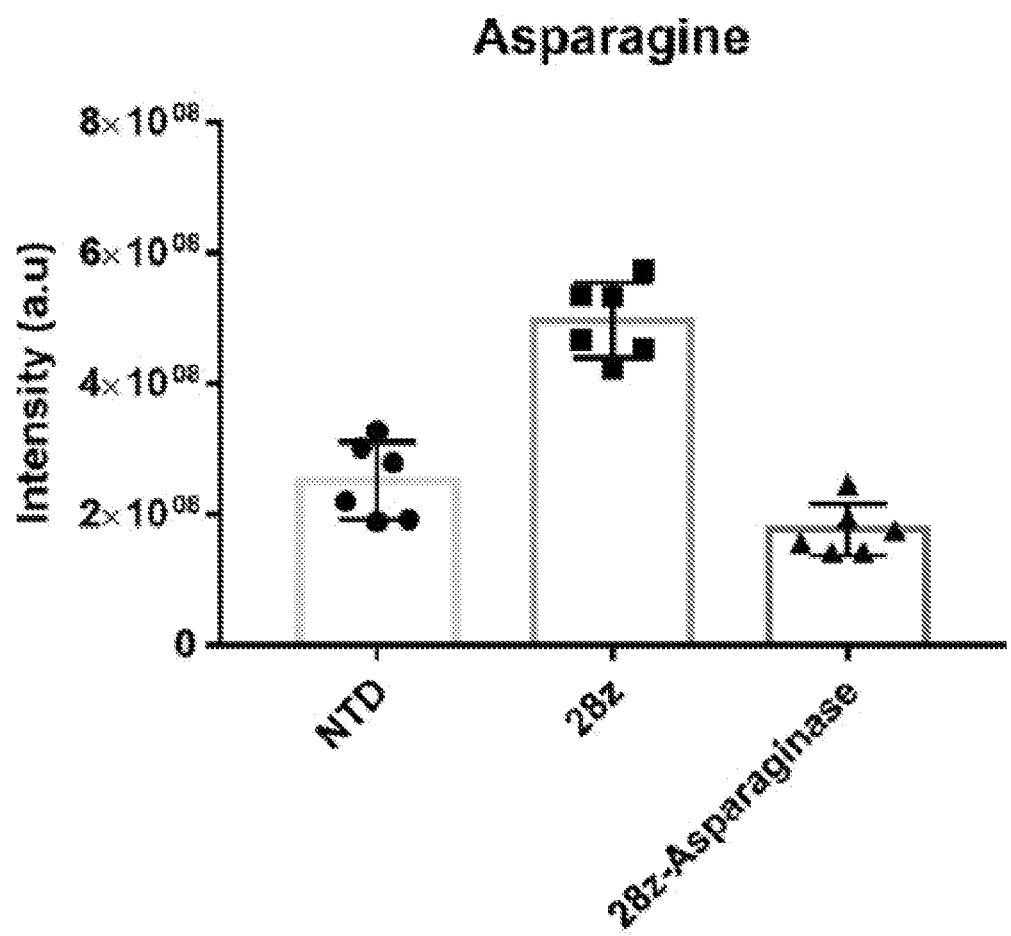
FIG. 2A is a graph of intracellular asparagine levels, and shows the impact of an asparaginase construct (28z-Asparaginase) on asparagine levels.
Figure 2B:
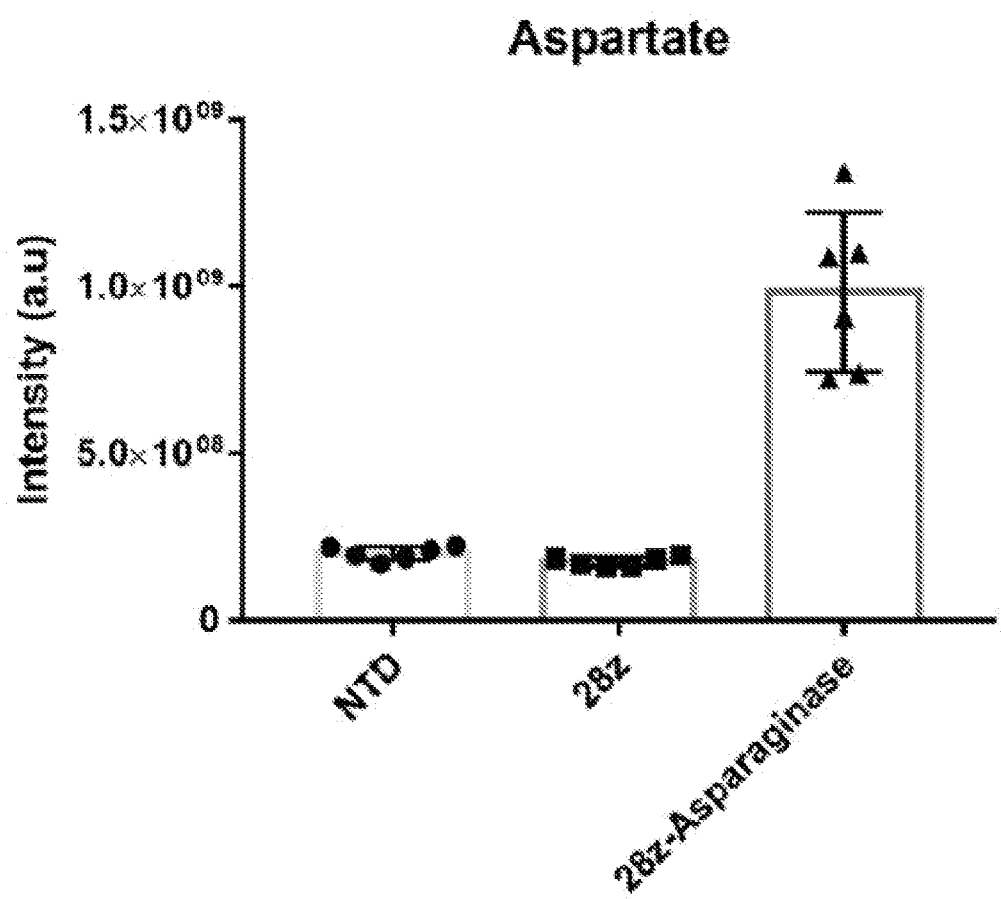
FIG. 2B is a graph of intracellular aspartate levels, and shows the impact of an asparaginase construct (28z-Asparaginase) on aspartate levels.

FIG. 2A is a graph of intracellular asparagine levels, and shows the impact of the asparaginase construct (28z-Asparaginase) on intracellular asparagine levels, as measured by LC/MS. FIG. 2B is a graph of intracellular aspartate levels, and shows the impact of the asparaginase construct (28z-Asparaginase) on intracellular aspartate levels, as measured by LC/MS.

Figure 2C:
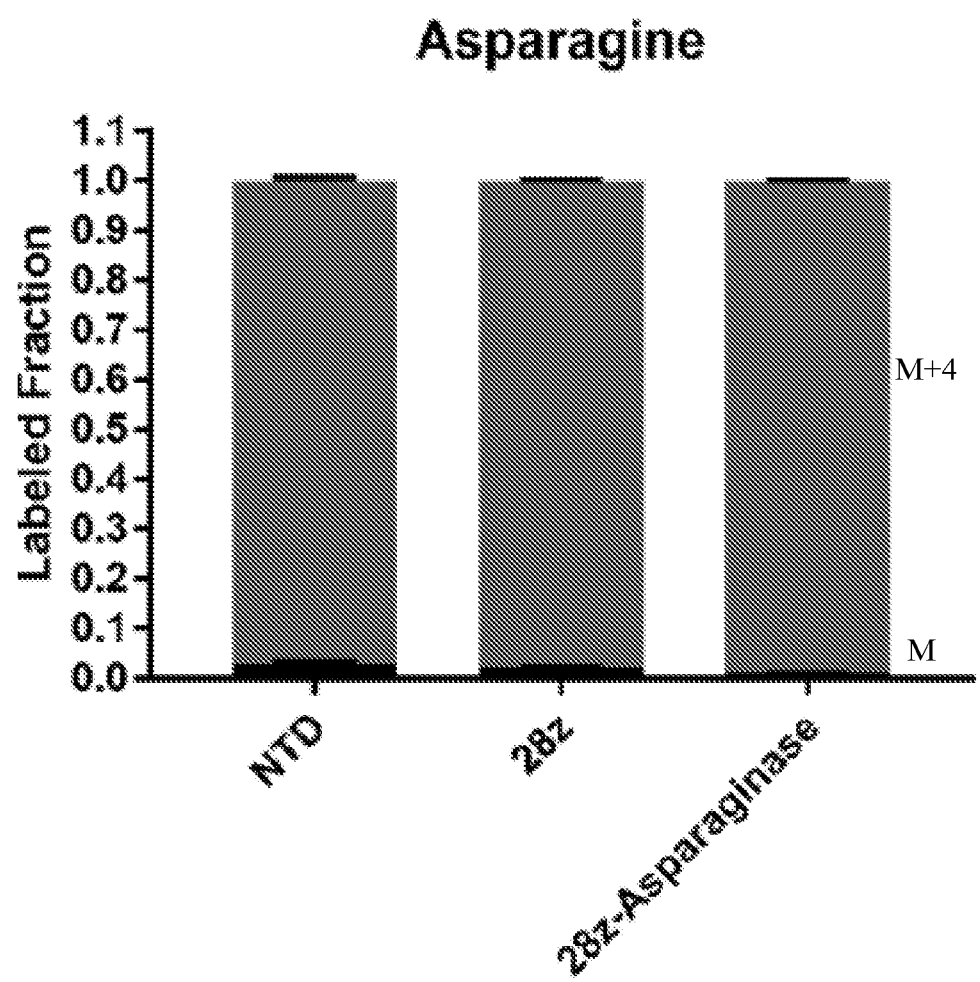
FIG. 2C is a graph of mass isotopomer distribution of intracellular asparagine, and shows the impact of the asparaginase construct (28z-Asparaginase) on the mass isotopomer distribution of asparagine.
Figure 2D:
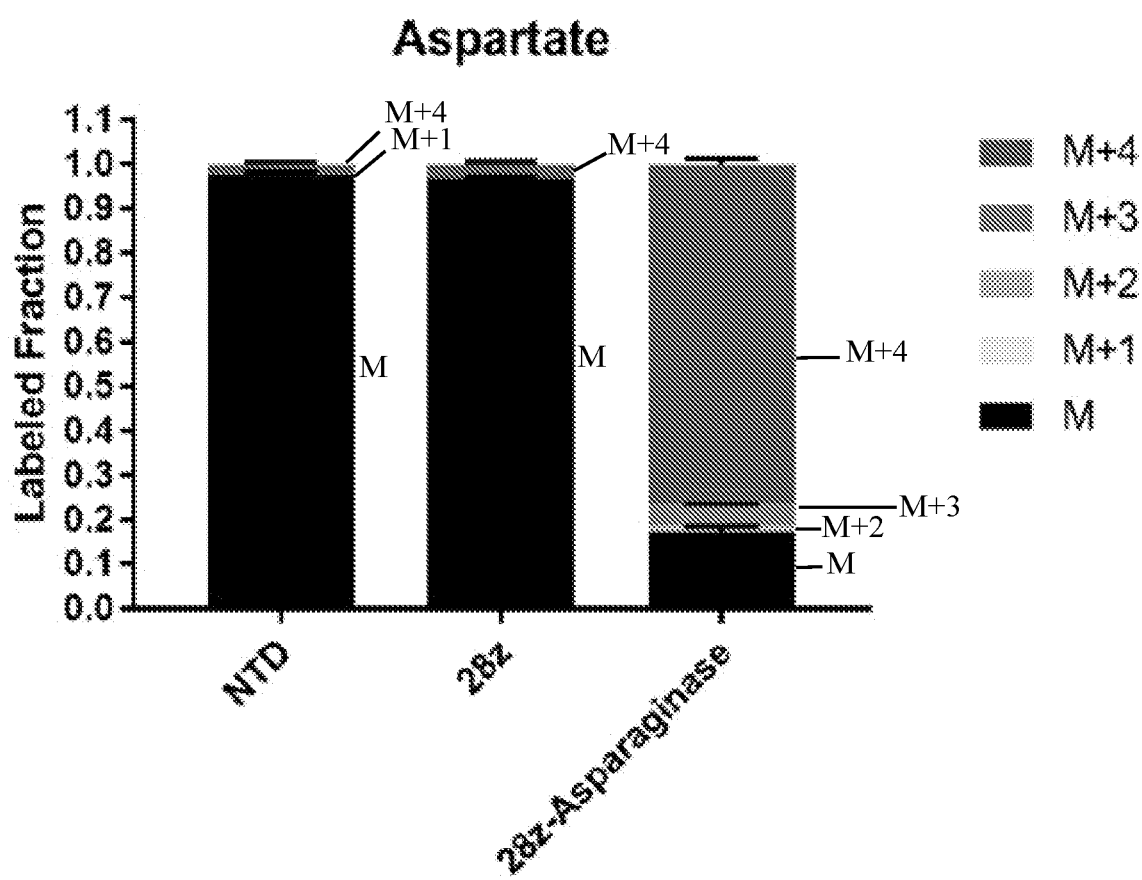
FIG. 2D is a graph of mass isotopomer distribution of intracellular aspartate, and shows the impact of the asparaginase construct (28z-Asparaginase) on the mass isotopomer distribution of aspartate.

FIG. 2C is a graph of mass isotopomer distribution of intracellular asparagine, and shows the impact of the asparaginase construct (28z-Asparaginase) on the mass isotopomer distribution of asparagine. FIG. 2D is a graph of mass isotopomer distribution of intracellular aspartate, and shows the impact of the asparaginase construct (28z-Asparaginase) on the mass isotopomer distribution of aspartate. The mass (M)+4 fraction corresponds to the amount of asparagine coming from the exogenous U-$^{13}$C-asparagine added to the media.

Figure 2E:
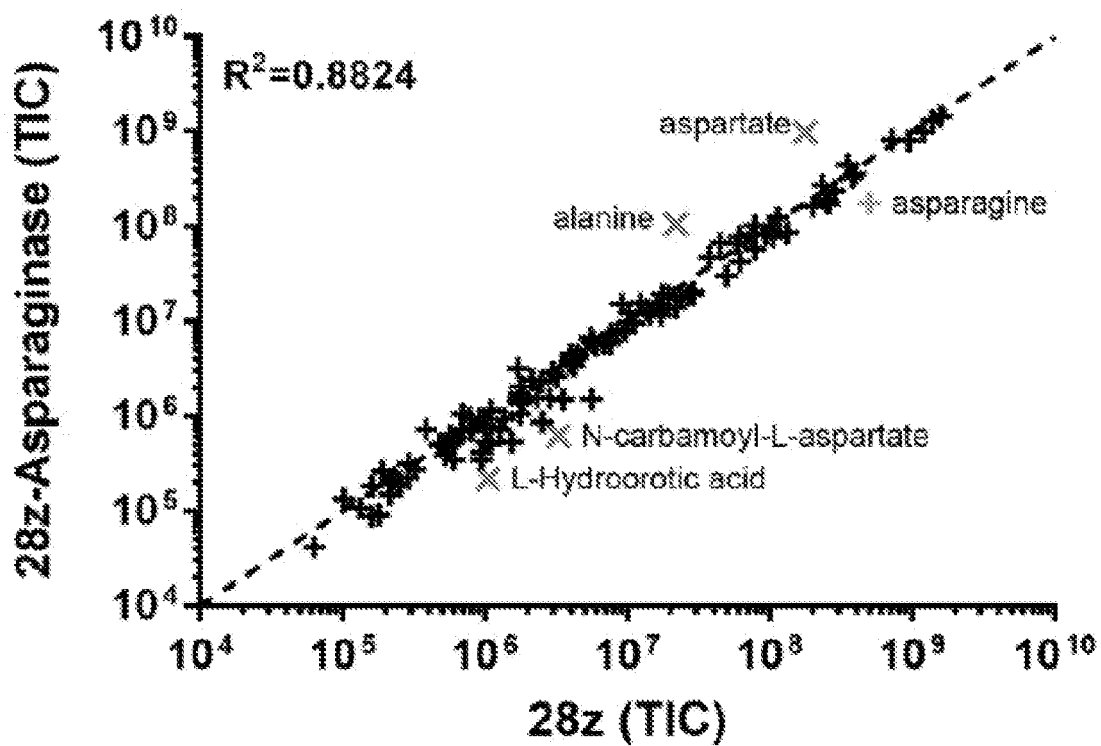
FIG. 2E is a graph of control cell (28z) numbers versus asparaginase-expressing CAR-T cell (28z-Asparaginase) numbers, and shows the levels of water-soluble metabolites in each cell type.

FIG. 2E is a graph of control cell (28z) numbers versus asparaginase-expressing CAR-T cell (28z-Asparaginase) numbers, and shows the levels of water-soluble metabolites in each cell type. Metabolites L-hydroorotic acid, N-carbamoyl-L-aspartate, asparagine, alanine and aspartate displayed a greater than 4-fold change.

Taken together, these data show that the designed asparaginase construct was functionally active in CAR-T cells following ectopic expression.

Impact of Asparaginase on T Cell Activation and Proliferation

Figure 3A:
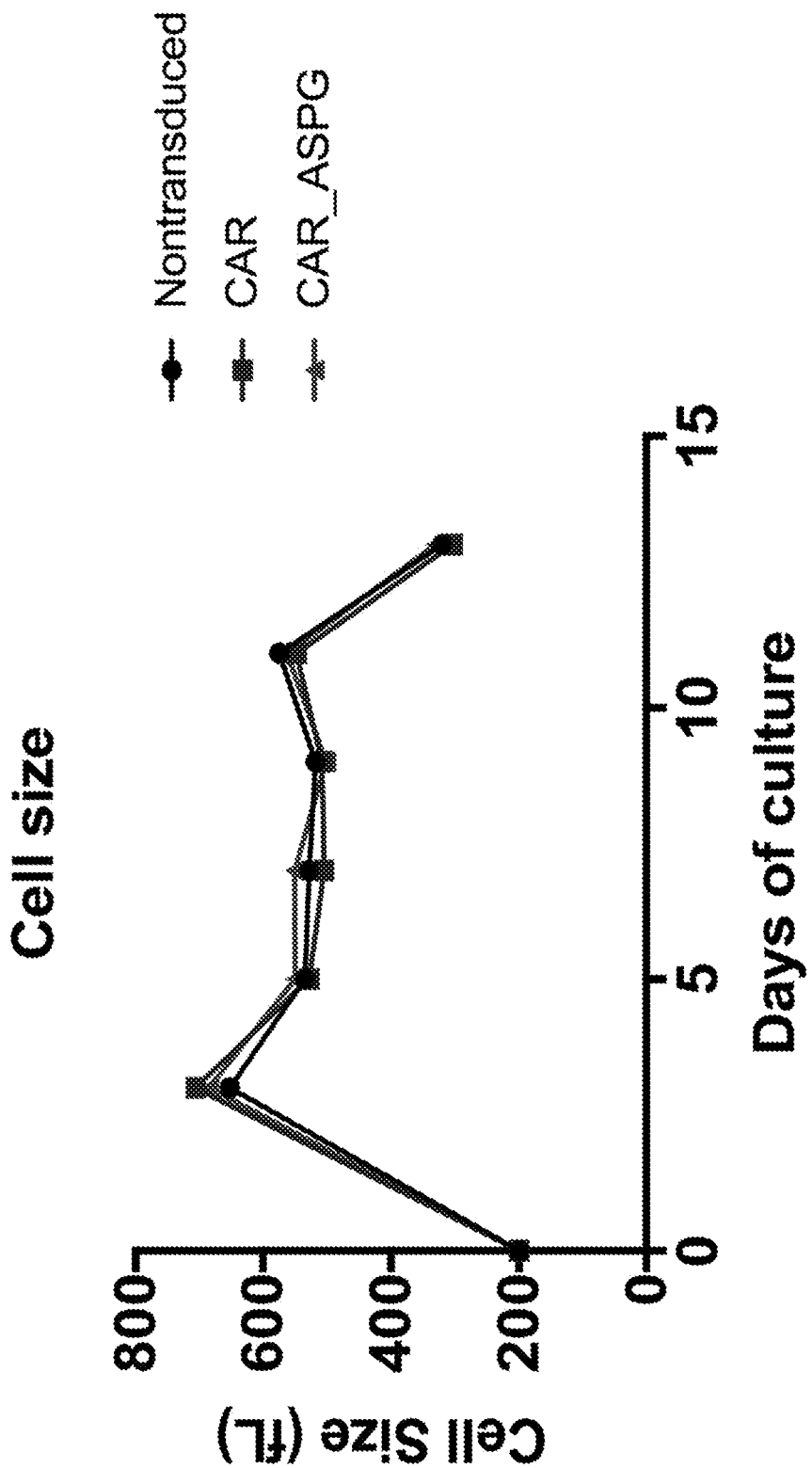
FIG. 3A is a graph of cell size (fL) versus time (days) of culture, and shows the size of nontransduced, CAR- and CAR-ASPG-transduced T cells following stimulation with anti-CD3/CD28 DYNABEADS®.

The impact of asparaginase expressed in conjunction with CAR on T cell activation and proliferation was examined. A mixed population of T cells was stimulated with anti-CD3/CD28 DYNABEADS®, and expanded in medium conditioned with 10% FBS. The mean cell volume was measured every other day beginning on day 3 until the number of cells in the culture ceased increasing and the mean cell volume was below 350 fL. FIG. 3A is a graph of cell size (fL) versus time (days) of culture, and shows the size of nontransduced, CAR- and CAR-ASPG-transduced T cells following stimulation with anti-CD3/CD28 DYNABEADS®. Representative data from two independent experiments are shown. The data in FIG. 3A show that CAR-T cells engineered to express asparaginase undergo effective activation.

T cells were stimulated as described above with respect to FIG. 3A, and total T (FIG. 3B), CD4-positive (FIG. 3C) and CD8-positive (FIG. 3D) cells were enumerated every other day by flow cytometry using live/dead, CD8-APC and COUNTBRIGHT™ beads, beginning on day 3 until the number of cells in the culture ceased increasing and the mean cell volume was below 350 fL.

Figure 3B:
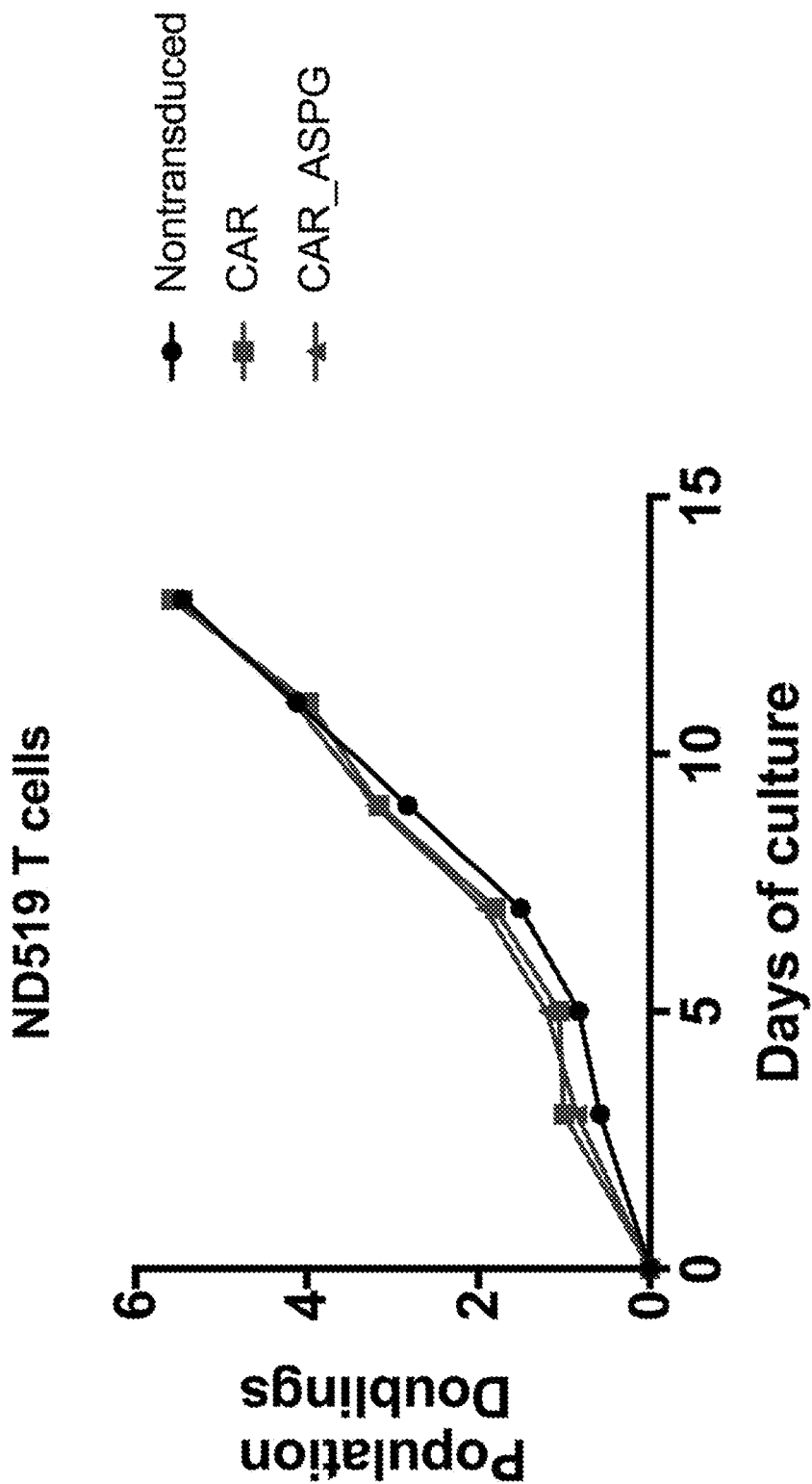
FIG. 3B is a graph of population doubling versus time (days) of culture, and shows the expansion of nontransduced, CAR- and CAR-ASPG-transduced T cells following stimulation with anti-CD3/CD28 DYNABEADS®.

FIG. 3B is a graph of population doubling versus time (days) of culture, and shows the expansion of nontransduced, CAR- and CAR-ASPG-transduced T cells following stimulation with anti-CD3/CD28 DYNABEADS®. The data in FIG. 3B show that CAR-T cells engineered to express asparaginase undergo log-phase expansion in response to surrogate antigens (DYNABEADS®).

Figure 3C:
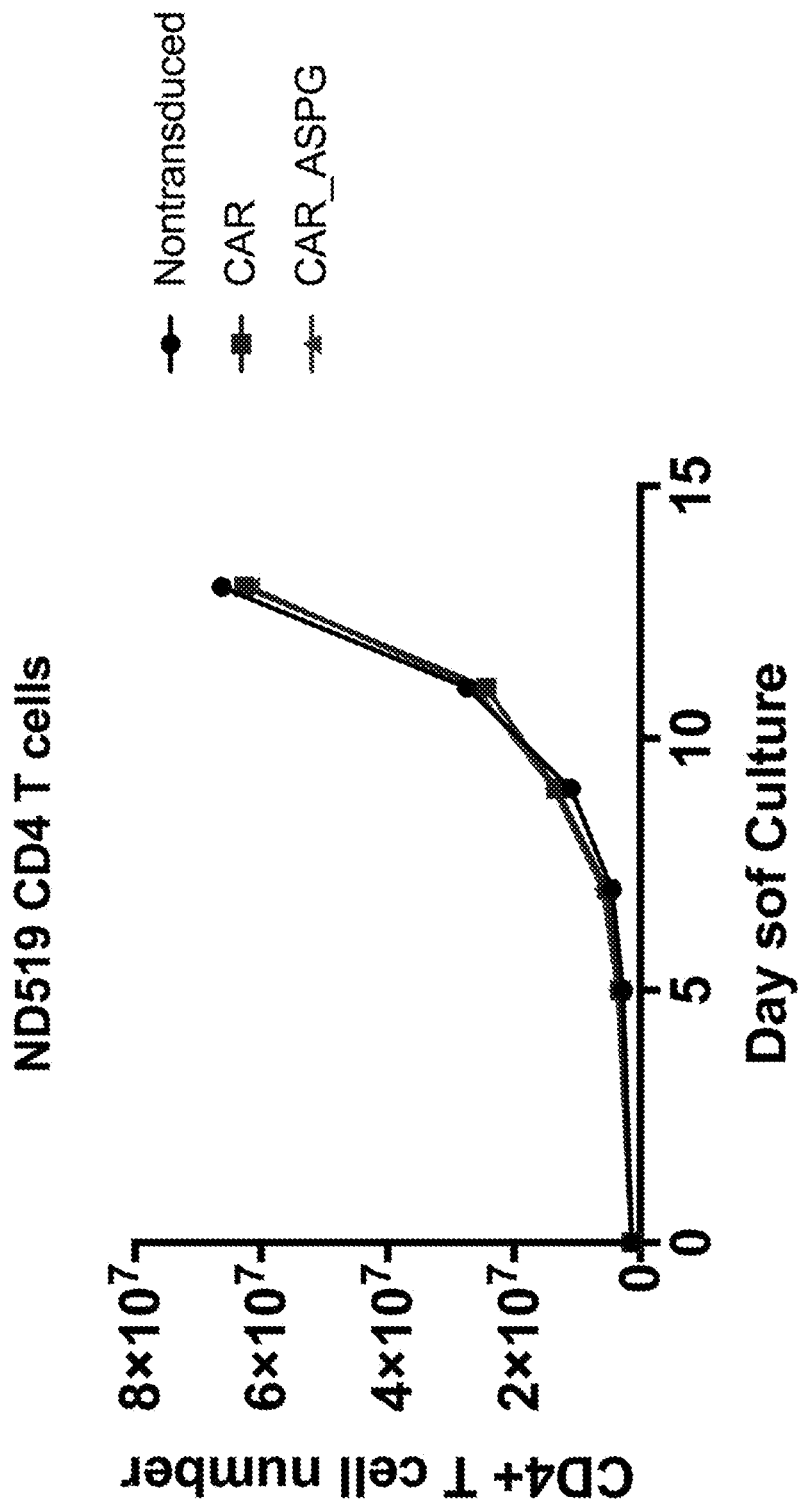
FIG. 3C is a graph of CD4-positive cells versus time (days) of culture, and shows the number of CD4-positive nontransduced, CAR- and CAR-ASPG-transduced T cells following stimulation with anti-CD3/CD28 DYNABEADS®.
Figure 3D:
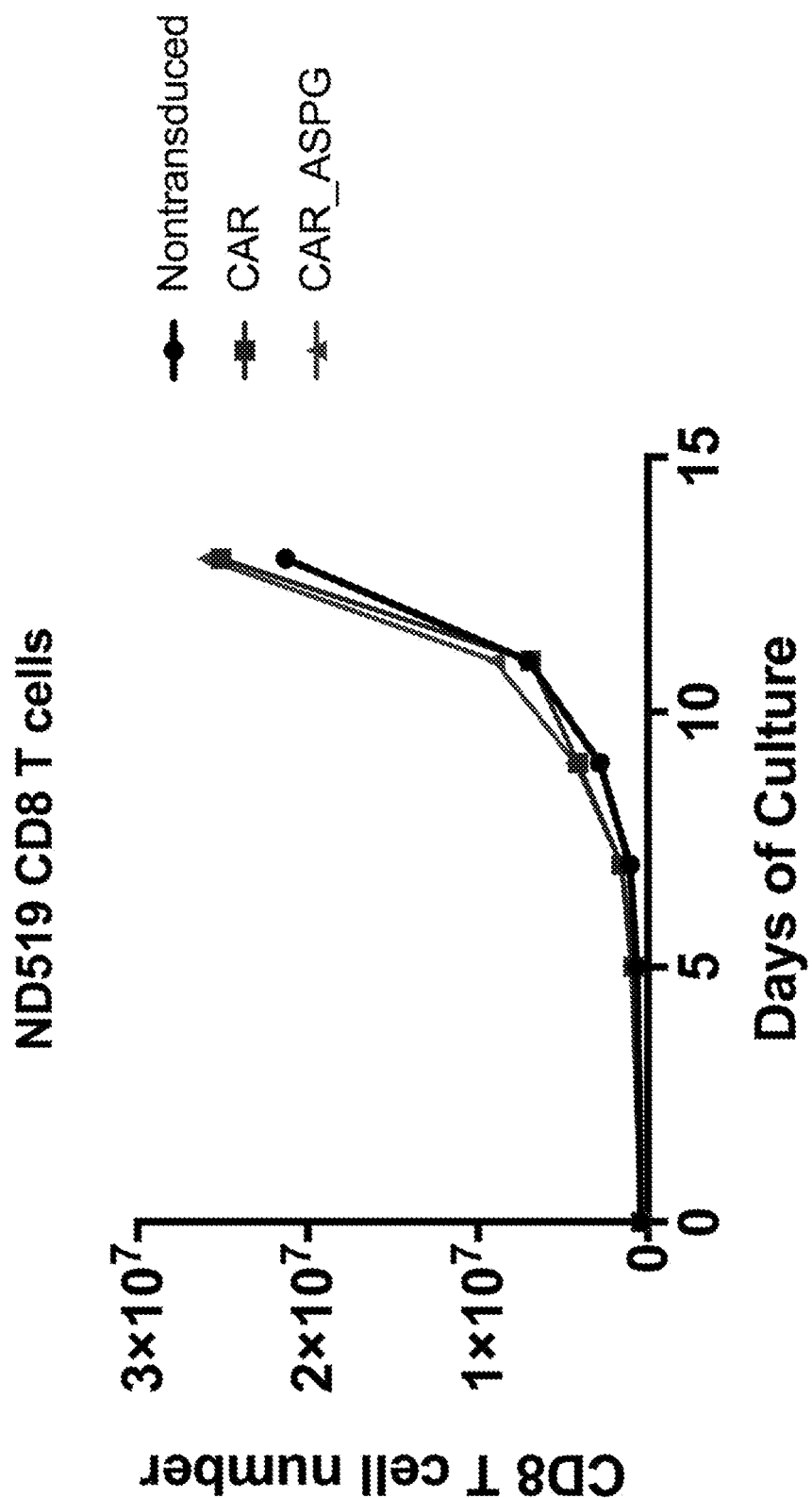
FIG. 3D is a graph of CD8-positive cells versus time (days) of culture, and shows the number of CD8-positive nontransduced, CAR- and CAR-ASPG-transduced T cells following stimulation with anti-CD3/CD28 DYNABEADS®.

FIG. 3C is a graph of CD4-positive cells versus time (days) of culture, and shows the number of CD4-positive nontransduced, CAR- and CAR-ASPG-transduced T cells following stimulation with anti-CD3/CD28 DYNABEADS®. FIG. 3D is a graph of CD8-positive cells versus time (days) of culture, and shows the number of CD8-positive nontransduced, CAR- and CAR-ASPG-transduced T cells following stimulation with anti-CD3/CD28 DYNABEADS®.

These data show that asparaginase-expressing CAR-T cells have replicative capacity in vitro.

Impact of Asparaginase on CAR-T Cytolytic Activity

The impact of asparaginase on CAR-T cytolytic activity was determined using a luciferase-based killing assay. Luciferase-based cytotoxicity of anti-mesothelin CAR-T cells was assessed against a commonly-used mesothelin-positive epithelial cell line (em-meso). The epithelial cell line was stably transduced with click beetle green luciferase. Primary human T cells were stimulated overnight with DYNABEADS®, and then lentivirally infected with CARs specific for mesothelin tumor antigen. These cells were expanded over nine to eleven days. After exiting their proliferative phase, CAR-T cells were co-cultured with em-meso target cells for 20 hours at either 20% $O_2$ or 3% $O_2$. Nontransduced (NTD) T cells were used as negative controls and compared to SS1.28Z (CAR) or SS1.28Z engineered to co-express asparaginase (CAR+ASPG). Em-meso cell lysis was measured at different effector:target ratios.

Figure 4A:
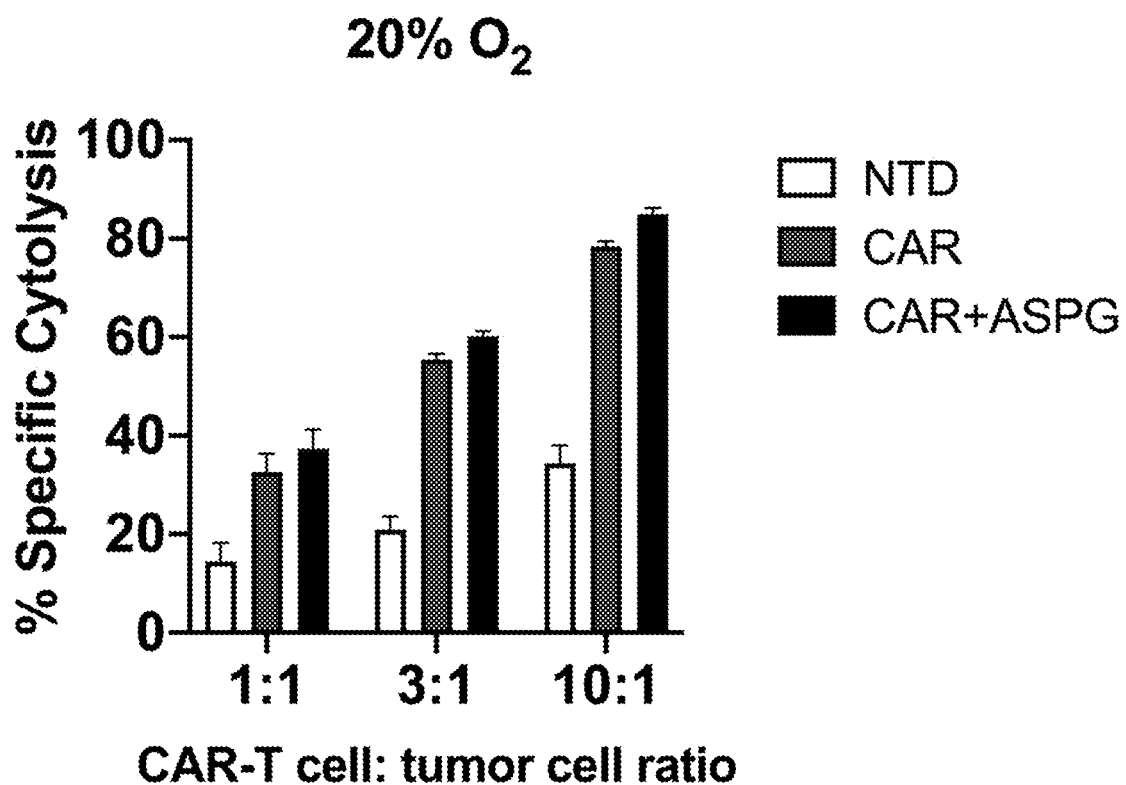
FIG. 4A is a graph of specific cytolysis versus CAR-T cell:tumor cell ratio, and shows the impact of asparaginase on cytolytic activity of CAR-T cells cultured at 20% $O_2$.
Figure 4B:
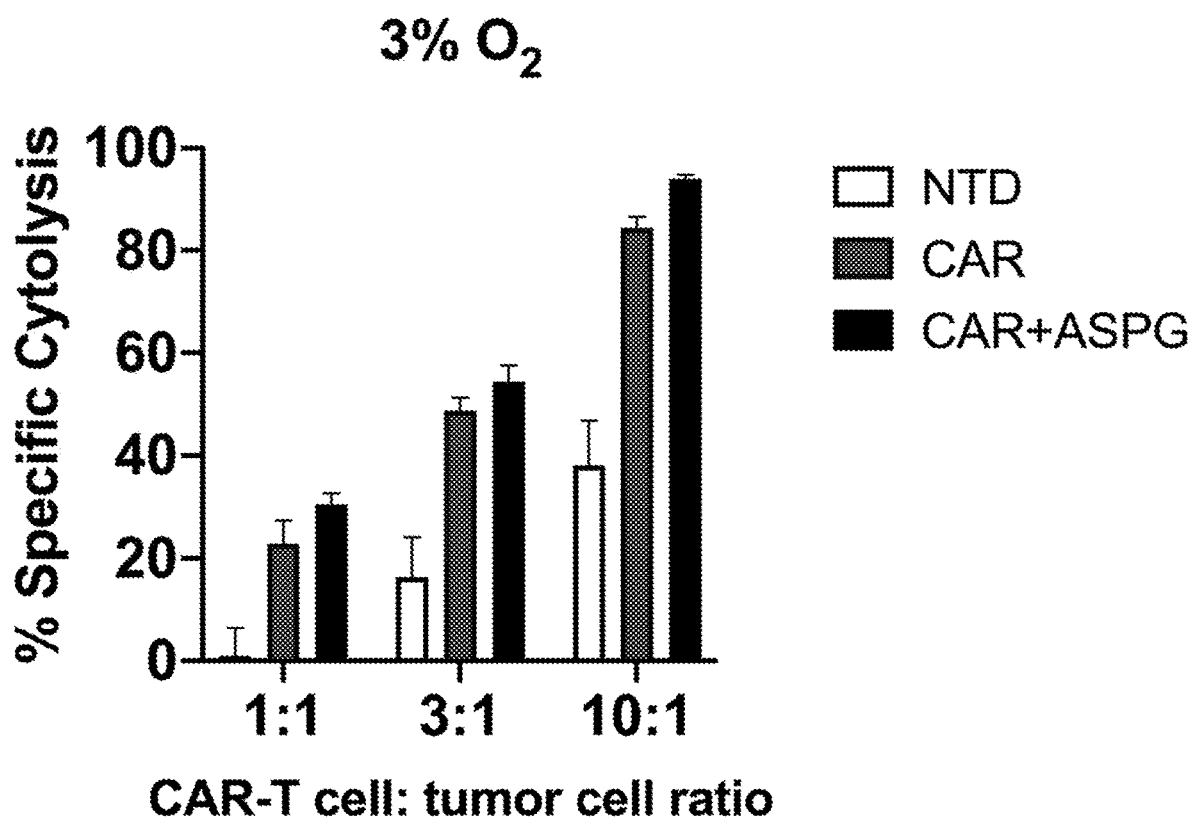
FIG. 4B is a graph of specific cytolysis versus CAR-T cell:tumor cell ratio, and shows the impact of asparaginase on cytolytic activity of CAR-T cells cultured at 3% $O_2$.

FIG. 4A is a graph of specific cytolysis versus CAR-T cell:tumor cell ratio, and shows the impact of asparaginase on cytolytic activity of CAR-T cells cultured at 20% $O_2$. FIG. 4B is a graph of specific cytolysis versus CAR-T cell:tumor cell ratio, and shows the impact of asparaginase on cytolytic activity of CAR-T cells cultured at 3% $O_2$. Six replicates were measured for each sample at each condition. One representative experiment is shown.

These data show that asparaginase-expressing CAR-T cells are functional in vitro at varying oxygen levels.

The relevant teachings of all patents, published applications and references cited herein are incorporated by reference in their entireties.

While this invention has been particularly shown and described with references to example embodiments thereof, it will be understood by those skilled in the art that various changes in form and details may be made therein without departing from the scope of the invention encompassed by the appended claims.

SEQUENCE LISTING

```
<160> NUMBER OF SEQ ID NOS: 2

<210> SEQ ID NO 1
<211> LENGTH: 9897
<212> TYPE: PRT
<213> ORGANISM: Cavia porcellus

<400> SEQUENCE: 1

Gly Thr Gly Cys Ala Cys Gly Ala Gly Thr Gly Gly Thr Thr Ala
1               5                   10                  15

Cys Ala Thr Cys Gly Ala Ala Cys Thr Gly Gly Ala Thr Cys Thr Cys
            20                  25                  30

Ala Ala Cys Ala Gly Cys Gly Gly Thr Ala Ala Gly Ala Thr Cys Cys
        35                  40                  45

Thr Thr Gly Ala Gly Ala Gly Thr Thr Thr Thr Cys Gly Cys Cys Cys
    50                  55                  60

Cys Gly Ala Ala Gly Ala Ala Cys Gly Thr Thr Thr Cys Cys Ala
65                  70                  75                  80

Ala Thr Gly Ala Thr Gly Ala Gly Cys Ala Cys Thr Thr Thr Ala
                85                  90                  95

Ala Ala Gly Thr Thr Cys Thr Gly Cys Thr Ala Thr Gly Thr Gly Gly
            100                 105                 110

Cys Gly Cys Gly Gly Thr Ala Thr Thr Ala Thr Cys Cys Cys Gly Thr
        115                 120                 125

Ala Thr Thr Gly Ala Cys Gly Cys Cys Gly Gly Gly Cys Ala Ala Gly
    130                 135                 140

Ala Gly Cys Ala Ala Cys Thr Cys Gly Gly Thr Cys Gly Cys Cys Gly
145                 150                 155                 160

Cys Ala Thr Ala Cys Ala Cys Thr Ala Thr Thr Cys Thr Cys Ala Gly
                165                 170                 175

Ala Ala Thr Gly Ala Cys Thr Thr Gly Gly Thr Thr Gly Ala Gly Thr
```

```
                    180                 185                 190
Ala Cys Thr Cys Ala Cys Cys Ala Gly Thr Cys Ala Cys Ala Gly Ala
                195                 200                 205
Ala Ala Ala Gly Cys Ala Thr Cys Thr Thr Ala Cys Gly Gly Ala Thr
            210                 215                 220
Gly Gly Cys Ala Thr Gly Ala Cys Ala Gly Thr Ala Ala Gly Ala Gly
225                 230                 235                 240
Ala Ala Thr Thr Ala Thr Gly Cys Ala Gly Thr Gly Cys Thr Gly Cys
                245                 250                 255
Cys Ala Thr Ala Ala Cys Cys Ala Thr Gly Ala Gly Thr Gly Ala Thr
            260                 265                 270
Ala Ala Cys Ala Cys Thr Gly Cys Gly Gly Cys Cys Ala Ala Cys Thr
            275                 280                 285
Thr Ala Cys Thr Thr Cys Thr Gly Ala Cys Ala Ala Cys Gly Ala Thr
            290                 295                 300
Cys Gly Gly Ala Gly Gly Ala Cys Cys Gly Ala Ala Gly Gly Ala Gly
305                 310                 315                 320
Cys Thr Ala Ala Cys Cys Gly Cys Thr Thr Thr Thr Thr Gly Cys
                325                 330                 335
Ala Cys Ala Ala Cys Ala Thr Gly Gly Gly Gly Ala Thr Cys Ala
            340                 345                 350
Thr Gly Thr Ala Ala Cys Thr Cys Gly Cys Thr Thr Gly Ala Thr
            355                 360                 365
Cys Gly Thr Thr Gly Gly Gly Ala Ala Cys Cys Gly Ala Gly Cys
            370                 375                 380
Thr Gly Ala Ala Thr Gly Ala Ala Gly Cys Cys Ala Thr Ala Cys Cys
385                 390                 395                 400
Ala Ala Ala Cys Gly Ala Cys Gly Ala Gly Cys Gly Thr Gly Ala Cys
                405                 410                 415
Ala Cys Cys Ala Cys Gly Ala Thr Gly Cys Cys Thr Gly Thr Ala Gly
            420                 425                 430
Cys Ala Ala Thr Gly Gly Cys Ala Ala Cys Ala Ala Cys Gly Thr Thr
            435                 440                 445
Gly Cys Gly Cys Ala Ala Cys Thr Ala Thr Thr Ala Ala Cys Thr
            450                 455                 460
Gly Gly Cys Gly Ala Ala Cys Thr Ala Cys Thr Thr Ala Cys Thr Cys
465                 470                 475                 480
Thr Ala Gly Cys Thr Thr Cys Cys Cys Gly Gly Cys Ala Ala Cys Ala
                485                 490                 495
Ala Thr Thr Ala Ala Thr Ala Gly Ala Cys Thr Gly Gly Ala Thr Gly
            500                 505                 510
Gly Ala Gly Gly Cys Gly Gly Ala Thr Ala Ala Ala Gly Thr Thr Gly
            515                 520                 525
Cys Ala Gly Gly Ala Cys Cys Ala Cys Thr Thr Cys Thr Gly Cys Gly
            530                 535                 540
Cys Thr Cys Gly Gly Cys Cys Cys Thr Thr Cys Cys Gly Gly Cys Thr
545                 550                 555                 560
Gly Gly Cys Thr Gly Gly Thr Thr Thr Ala Thr Thr Gly Cys Thr Gly
                565                 570                 575
Ala Thr Ala Ala Ala Thr Cys Thr Gly Gly Ala Gly Cys Cys Gly Gly
            580                 585                 590
Thr Gly Ala Gly Cys Gly Thr Gly Gly Gly Thr Cys Thr Cys Gly Cys
            595                 600

```
Gly Gly Thr Ala Thr Cys Ala Thr Thr Gly Cys Ala Gly Cys Ala Cys
        610             615                 620

Thr Gly Gly Gly Gly Cys Cys Ala Gly Ala Thr Gly Gly Thr Ala Ala
625                 630                 635                 640

Gly Cys Cys Cys Thr Cys Cys Cys Gly Thr Ala Thr Cys Gly Thr Ala
                    645                 650                 655

Gly Thr Thr Ala Thr Cys Thr Ala Cys Ala Cys Gly Ala Cys Gly Gly
                660                 665                 670

Gly Gly Ala Gly Thr Cys Ala Gly Gly Cys Ala Ala Cys Thr Ala Thr
            675                 680                 685

Gly Gly Ala Thr Gly Ala Cys Gly Ala Ala Thr Ala Gly Ala
        690                 695                 700

Cys Ala Gly Ala Thr Cys Gly Cys Thr Gly Ala Gly Ala Thr Ala Gly
705                 710                 715                 720

Gly Thr Gly Cys Cys Thr Cys Ala Cys Thr Gly Ala Thr Thr Ala Ala
                    725                 730                 735

Gly Cys Ala Thr Thr Gly Gly Thr Ala Ala Cys Thr Gly Thr Cys Ala
                740                 745                 750

Gly Ala Cys Cys Ala Ala Gly Thr Thr Thr Ala Cys Thr Cys Ala Thr
            755                 760                 765

Ala Thr Ala Thr Ala Cys Thr Thr Thr Ala Gly Ala Thr Thr Gly Ala
770                 775                 780

Thr Thr Thr Ala Ala Ala Ala Cys Thr Thr Cys Ala Thr Thr Thr Thr
785                 790                 795                 800

Thr Ala Ala Thr Thr Thr Ala Ala Ala Ala Gly Gly Ala Thr Cys Thr
            805                 810                 815

Ala Gly Gly Thr Gly Ala Ala Gly Ala Thr Cys Cys Thr Thr Thr Thr
                820                 825                 830

Thr Gly Ala Thr Ala Ala Thr Cys Thr Cys Ala Thr Gly Ala Cys Cys
        835                 840                 845

Ala Ala Ala Ala Thr Cys Cys Cys Thr Thr Ala Ala Cys Gly Thr Gly
850                 855                 860

Ala Gly Thr Thr Thr Thr Cys Gly Thr Thr Cys Cys Ala Cys Thr Gly
865                 870                 875                 880

Ala Gly Cys Gly Thr Cys Ala Gly Ala Cys Cys Cys Cys Gly Thr Ala
                885                 890                 895

Gly Ala Ala Ala Ala Gly Ala Thr Cys Ala Ala Ala Gly Gly Ala Thr
            900                 905                 910

Cys Thr Thr Cys Thr Thr Gly Ala Gly Ala Thr Cys Cys Thr Thr Thr
        915                 920                 925

Thr Thr Thr Thr Cys Thr Gly Cys Gly Cys Gly Thr Ala Ala Thr Cys
        930                 935                 940

Thr Gly Cys Thr Gly Cys Thr Thr Gly Cys Ala Ala Ala Cys Ala Ala
945                 950                 955                 960

Ala Ala Ala Ala Ala Cys Cys Ala Cys Cys Gly Cys Thr Ala Cys Cys
                965                 970                 975

Ala Gly Cys Gly Gly Thr Gly Gly Thr Thr Thr Gly Thr Thr Thr Gly
            980                 985                 990

Cys Cys Gly Gly Ala Thr Cys Ala Ala Gly Ala Gly Cys Thr Ala Cys
        995             1000                1005

Cys Ala Ala Cys Thr Cys Thr Thr Thr Thr Thr Cys Cys Gly Ala
        1010            1015                1020
```

Ala Gly Gly Thr Ala Ala Cys Thr Gly Gly Cys Thr Cys Ala
1025                    1030                1035

Gly Cys Ala Gly Ala Gly Cys Gly Cys Ala Gly Ala Thr Ala Cys
1040                    1045                1050

Cys Ala Ala Ala Thr Ala Cys Thr Gly Thr Thr Cys Thr Thr Cys
1055                    1060                1065

Thr Ala Gly Thr Gly Thr Ala Gly Cys Cys Gly Thr Ala Gly Thr
1070                    1075                1080

Thr Ala Gly Gly Cys Cys Ala Cys Cys Ala Cys Thr Thr Cys Ala
1085                    1090                1095

Ala Gly Ala Ala Cys Thr Cys Thr Gly Thr Ala Gly Cys Ala Cys
1100                    1105                1110

Cys Gly Cys Cys Thr Ala Cys Ala Thr Ala Cys Cys Thr Cys Gly
1115                    1120                1125

Cys Thr Cys Thr Gly Cys Thr Ala Ala Thr Cys Cys Thr Gly Thr
1130                    1135                1140

Thr Ala Cys Cys Ala Gly Thr Gly Gly Cys Thr Gly Cys Thr Gly
1145                    1150                1155

Cys Cys Ala Gly Thr Gly Gly Cys Gly Ala Thr Ala Ala Gly Thr
1160                    1165                1170

Cys Gly Thr Gly Thr Cys Thr Thr Ala Cys Cys Gly Gly Gly Thr
1175                    1180                1185

Thr Gly Gly Ala Cys Thr Cys Ala Ala Gly Ala Cys Gly Ala Thr
1190                    1195                1200

Ala Gly Thr Thr Ala Cys Cys Gly Gly Ala Thr Ala Ala Gly Gly
1205                    1210                1215

Cys Gly Cys Ala Gly Cys Gly Gly Thr Cys Gly Gly Gly Cys Thr
1220                    1225                1230

Gly Ala Ala Cys Gly Gly Gly Gly Gly Thr Thr Cys Gly Thr
1235                    1240                1245

Gly Cys Ala Cys Ala Cys Ala Gly Cys Cys Ala Gly Cys Thr
1250                    1255                1260

Thr Gly Gly Ala Gly Cys Gly Ala Ala Cys Gly Ala Cys Cys Thr
1265                    1270                1275

Ala Cys Ala Cys Cys Gly Ala Ala Cys Thr Gly Ala Gly Ala Thr
1280                    1285                1290

Ala Cys Cys Thr Ala Cys Ala Gly Cys Gly Thr Gly Ala Gly Cys
1295                    1300                1305

Thr Ala Thr Gly Ala Gly Ala Ala Ala Gly Cys Gly Cys Cys Ala
1310                    1315                1320

Cys Gly Cys Thr Thr Cys Cys Gly Ala Ala Gly Gly Ala
1325                    1330                1335

Gly Ala Ala Ala Gly Gly Cys Gly Gly Ala Cys Ala Gly Gly Thr
1340                    1345                1350

Ala Thr Cys Cys Gly Gly Thr Ala Ala Gly Cys Gly Gly Cys Ala
1355                    1360                1365

Gly Gly Gly Thr Cys Gly Gly Ala Ala Cys Ala Gly Gly Ala Gly
1370                    1375                1380

Ala Gly Cys Gly Cys Ala Cys Gly Ala Gly Gly Ala Gly Cys
1385                    1390                1395

Thr Thr Cys Cys Ala Gly Gly Gly Gly Ala Ala Ala Cys Gly
1400                    1405                1410

Cys Cys Thr Gly Gly Thr Ala Thr Cys Thr Thr Thr Ala Thr Ala

-continued

```
            1415                1420                1425
Gly Thr Cys Cys Thr Gly Thr Cys Gly Gly Thr Thr Thr Cys
        1430                1435                1440
Gly Cys Cys Ala Cys Cys Thr Cys Thr Gly Ala Cys Thr Thr Gly
        1445                1450                1455
Ala Gly Cys Gly Thr Cys Gly Ala Thr Thr Thr Thr Gly Thr
        1460                1465                1470
Gly Ala Thr Gly Cys Thr Cys Gly Thr Cys Ala Gly Gly Gly
        1475                1480                1485
Gly Gly Cys Gly Gly Ala Gly Cys Cys Thr Ala Thr Gly Gly Ala
        1490                1495                1500
Ala Ala Ala Ala Cys Gly Cys Cys Ala Gly Cys Ala Ala Cys Gly
        1505                1510                1515
Cys Gly Gly Cys Cys Thr Thr Thr Thr Thr Ala Cys Gly Gly Thr
        1520                1525                1530
Thr Cys Cys Thr Gly Gly Cys Cys Thr Thr Thr Thr Gly Cys Thr
        1535                1540                1545
Gly Gly Cys Cys Thr Thr Thr Thr Gly Cys Thr Cys Ala Cys Ala
        1550                1555                1560
Thr Gly Thr Thr Cys Thr Thr Thr Cys Cys Thr Gly Cys Gly Thr
        1565                1570                1575
Thr Ala Thr Cys Cys Cys Cys Thr Gly Ala Thr Thr Cys Thr Gly
        1580                1585                1590
Thr Gly Gly Ala Thr Ala Ala Cys Cys Gly Thr Ala Thr Thr Ala
        1595                1600                1605
Cys Cys Gly Cys Cys Thr Thr Thr Gly Ala Gly Thr Gly Ala Gly
        1610                1615                1620
Cys Thr Gly Ala Thr Ala Cys Cys Gly Cys Thr Cys Gly Cys Cys
        1625                1630                1635
Gly Cys Ala Gly Cys Cys Gly Ala Ala Cys Gly Ala Cys Cys Gly
        1640                1645                1650
Ala Gly Cys Gly Cys Ala Gly Cys Gly Ala Gly Thr Cys Ala Gly
        1655                1660                1665
Thr Gly Ala Gly Cys Gly Ala Gly Gly Ala Ala Gly Cys Gly Gly
        1670                1675                1680
Ala Ala Gly Ala Gly Cys Gly Cys Cys Cys Ala Ala Thr Ala Cys
        1685                1690                1695
Gly Cys Ala Ala Ala Cys Cys Gly Cys Cys Thr Cys Thr Cys Cys
        1700                1705                1710
Cys Cys Gly Cys Gly Cys Gly Thr Thr Gly Gly Cys Cys Gly Ala
        1715                1720                1725
Thr Thr Cys Ala Thr Thr Ala Ala Thr Gly Cys Ala Gly Cys Thr
        1730                1735                1740
Gly Gly Cys Ala Cys Gly Ala Cys Ala Gly Gly Thr Thr Thr Cys
        1745                1750                1755
Cys Cys Gly Ala Cys Thr Gly Gly Ala Ala Ala Gly Cys Gly Gly
        1760                1765                1770
Gly Cys Ala Gly Thr Gly Ala Gly Cys Gly Cys Ala Ala Cys Gly
        1775                1780                1785
Cys Ala Ala Thr Thr Ala Ala Thr Gly Thr Gly Ala Gly Thr Thr
        1790                1795                1800
Ala Gly Cys Thr Cys Ala Cys Thr Cys Ala Thr Thr Ala Gly Gly
        1805                1810                1815
```

```
Cys Ala Cys Cys Cys Cys Ala Gly Gly Cys Thr Thr  Thr Ala Cys
    1820            1825                1830

Ala Cys Thr Thr Thr Ala Thr Gly Cys Thr Thr Cys  Cys Gly Gly
    1835            1840                1845

Cys Thr Cys Gly Thr Ala Thr Gly Thr Thr Gly Thr  Gly Thr Gly
    1850            1855                1860

Gly Ala Ala Thr Thr Gly Thr Gly Ala Gly Cys Gly  Gly Ala Thr
    1865            1870                1875

Ala Ala Cys Ala Ala Thr Thr Thr Cys Ala Cys Ala  Cys Ala Gly
    1880            1885                1890

Gly Ala Ala Ala Cys Ala Gly Cys Thr Ala Thr Gly  Ala Cys Cys
    1895            1900                1905

Ala Thr Gly Ala Thr Thr Ala Cys Gly Cys Cys Ala  Ala Gly Cys
    1910            1915                1920

Gly Cys Gly Cys Ala Ala Thr Thr Ala Ala Cys Cys  Cys Thr Cys
    1925            1930                1935

Ala Cys Thr Ala Ala Ala Gly Gly Gly Ala Ala Cys  Ala Ala Ala
    1940            1945                1950

Ala Gly Cys Thr Gly Gly Ala Gly Cys Thr Gly Cys  Ala Ala Gly
    1955            1960                1965

Cys Thr Thr Ala Ala Thr Thr Ala Gly Thr Cys  Thr Thr Ala
    1970            1975                1980

Thr Gly Cys Ala Ala Thr Ala Cys Thr Cys Thr  Gly Thr Ala
    1985            1990                1995

Gly Thr Cys Thr Thr Gly Cys Ala Ala Cys Ala Thr  Gly Gly Thr
    2000            2005                2010

Ala Ala Cys Gly Ala Thr Gly Ala Gly Thr Thr Ala  Gly Cys Ala
    2015            2020                2025

Ala Cys Ala Thr Gly Cys Cys Thr Thr Ala Cys Ala  Ala Gly Gly
    2030            2035                2040

Ala Gly Ala Gly Ala Ala Ala Ala Gly Cys Ala  Cys Cys Gly
    2045            2050                2055

Thr Gly Cys Ala Thr Gly Cys Cys Gly Ala Thr  Gly Gly Thr
    2060            2065                2070

Gly Gly Ala Ala Gly Thr Ala Ala Gly Gly Thr Gly  Gly Thr Ala
    2075            2080                2085

Cys Gly Ala Thr Cys Gly Thr Gly Cys Cys Thr Thr  Ala Thr Thr
    2090            2095                2100

Ala Gly Gly Ala Ala Gly Gly Cys Ala Ala Cys Ala  Gly Ala Cys
    2105            2110                2115

Gly Gly Gly Thr Cys Thr Gly Ala Cys Ala Thr Gly  Gly Ala Thr
    2120            2125                2130

Thr Gly Gly Ala Cys Gly Ala Ala Cys Cys Ala Cys  Thr Gly Ala
    2135            2140                2145

Ala Thr Thr Gly Cys Cys Gly Cys Ala Thr Thr Gly  Cys Ala Gly
    2150            2155                2160

Ala Gly Ala Thr Ala Thr Thr Gly Thr Ala Thr Thr  Thr Ala Ala
    2165            2170                2175

Gly Thr Gly Cys Cys Thr Ala Gly Cys Thr Cys Gly  Ala Thr Ala
    2180            2185                2190

Cys Ala Thr Ala Ala Ala Cys Gly Gly Gly Thr Cys  Thr Cys Thr
    2195            2200                2205
```

-continued

| | | | | | | | | | | | |
|---|---|---|---|---|---|---|---|---|---|---|---|
|Cys|Thr|Gly|Gly|Thr|Thr|Ala|Gly|Ala|Cys|Cys|Ala|Gly|Ala|Thr|
| |2210| | | |2215| | | |2220| | | | | |

Cys Thr Gly Gly Thr Thr Ala Gly Ala Cys Cys Ala Gly Ala Thr
    2210                2215                2220

Cys Thr Gly Ala Gly Cys Cys Thr Gly Gly Ala Gly Cys Thr
    2225                2230                2235

Cys Thr Cys Thr Gly Gly Cys Thr Ala Ala Cys Thr Ala Gly Gly
    2240                2245                2250

Gly Ala Ala Cys Cys Cys Ala Cys Thr Gly Cys Thr Thr Ala Ala
    2255                2260                2265

Gly Cys Cys Thr Cys Ala Ala Thr Ala Ala Ala Gly Cys Thr Thr
    2270                2275                2280

Gly Cys Cys Thr Thr Gly Ala Gly Thr Gly Cys Thr Thr Cys Ala
    2285                2290                2295

Ala Gly Thr Ala Gly Thr Gly Thr Gly Thr Gly Cys Cys Cys Gly
    2300                2305                2310

Thr Cys Thr Gly Thr Thr Gly Thr Gly Thr Gly Ala Cys Thr Cys
    2315                2320                2325

Thr Gly Gly Thr Ala Ala Cys Thr Ala Gly Ala Gly Ala Thr Cys
    2330                2335                2340

Cys Cys Thr Cys Ala Gly Ala Cys Cys Cys Thr Thr Thr Thr Ala
    2345                2350                2355

Gly Thr Cys Ala Gly Thr Gly Thr Gly Gly Ala Ala Ala Ala Thr
    2360                2365                2370

Cys Thr Cys Thr Ala Gly Cys Ala Gly Thr Gly Gly Cys Gly Cys
    2375                2380                2385

Cys Cys Gly Ala Ala Cys Ala Gly Gly Gly Ala Cys Thr Thr Gly
    2390                2395                2400

Ala Ala Ala Gly Cys Gly Ala Ala Ala Gly Gly Gly Ala Ala Ala
    2405                2410                2415

Cys Cys Ala Gly Ala Gly Gly Ala Gly Cys Thr Cys Thr Cys Thr
    2420                2425                2430

Cys Gly Ala Cys Gly Cys Ala Gly Gly Ala Cys Thr Cys Gly Gly
    2435                2440                2445

Cys Thr Thr Gly Cys Thr Gly Ala Ala Gly Cys Gly Cys Gly Cys
    2450                2455                2460

Ala Cys Gly Gly Cys Ala Ala Gly Ala Gly Gly Cys Gly Ala Gly
    2465                2470                2475

Gly Gly Gly Cys Gly Gly Cys Gly Ala Cys Thr Gly Gly Thr Gly
    2480                2485                2490

Ala Gly Thr Ala Cys Gly Cys Cys Ala Ala Ala Ala Ala Thr Thr
    2495                2500                2505

Thr Thr Gly Ala Cys Thr Ala Gly Cys Gly Gly Ala Gly Gly Cys
    2510                2515                2520

Thr Ala Gly Ala Ala Gly Gly Ala Gly Ala Gly Ala Gly Ala Thr
    2525                2530                2535

Gly Gly Gly Thr Gly Cys Gly Ala Gly Ala Gly Cys Gly Thr Cys
    2540                2545                2550

Ala Gly Thr Ala Thr Thr Ala Ala Gly Cys Gly Gly Gly Gly Gly
    2555                2560                2565

Ala Gly Ala Ala Thr Thr Ala Gly Ala Thr Cys Gly Cys Gly Ala
    2570                2575                2580

Thr Gly Gly Gly Ala Ala Ala Ala Ala Thr Thr Cys Gly Gly
    2585                2590                2595

Thr Thr Ala Ala Gly Gly Cys Cys Ala Gly Gly Gly Gly Ala

```
                    2600                2605                2610

Ala Ala  Gly Ala Ala Ala Ala  Ala Ala Thr Ala Thr  Ala Ala Ala
    2615                2620                2625

Thr Thr  Ala Ala Ala Ala Cys  Ala Thr Ala Thr Ala  Gly Thr Ala
    2630                2635                2640

Thr Gly  Gly Gly Cys Ala Ala  Gly Cys Ala Gly Gly  Gly Ala Gly
    2645                2650                2655

Cys Thr  Ala Gly Ala Ala Cys  Gly Ala Thr Thr Cys  Gly Cys Ala
    2660                2665                2670

Gly Thr  Thr Ala Ala Thr Cys  Cys Thr Gly Gly Cys  Cys Thr Gly
    2675                2680                2685

Thr Thr  Ala Gly Ala Ala Ala  Cys Ala Thr Cys Ala  Gly Ala Ala
    2690                2695                2700

Gly Gly  Cys Thr Gly Thr Ala  Gly Ala Cys Ala Ala  Ala Thr Ala
    2705                2710                2715

Cys Thr  Gly Gly Gly Ala Cys  Ala Gly Cys Thr Ala  Cys Ala Ala
    2720                2725                2730

Cys Cys  Ala Thr Cys Cys Cys  Thr Thr Cys Ala Gly  Ala Cys Ala
    2735                2740                2745

Gly Gly  Ala Thr Cys Ala Gly  Ala Ala Gly Ala Ala  Cys Thr Thr
    2750                2755                2760

Ala Gly  Ala Thr Cys Ala Thr  Thr Ala Thr Ala Thr  Ala Ala Thr
    2765                2770                2775

Ala Cys  Ala Gly Thr Ala Gly  Cys Ala Ala Cys Cys  Cys Thr Cys
    2780                2785                2790

Thr Ala  Thr Thr Gly Thr Gly  Thr Gly Cys Ala Thr  Cys Ala Ala
    2795                2800                2805

Ala Gly  Gly Ala Thr Ala Gly  Ala Gly Ala Thr Ala  Ala Ala Ala
    2810                2815                2820

Gly Ala  Cys Ala Cys Cys Ala  Ala Gly Gly Ala Ala  Gly Cys Thr
    2825                2830                2835

Thr Thr  Ala Gly Ala Cys Ala  Ala Gly Ala Thr Ala  Gly Ala Gly
    2840                2845                2850

Gly Ala  Ala Gly Ala Gly Cys  Ala Ala Ala Cys Ala  Ala Ala Ala
    2855                2860                2865

Ala Gly  Thr Ala Ala Gly Ala  Cys Cys Ala Cys Cys  Gly Cys Ala
    2870                2875                2880

Cys Ala  Gly Cys Ala Ala Gly  Cys Gly Gly Cys Cys  Gly Cys Thr
    2885                2890                2895

Gly Ala  Thr Cys Thr Thr Cys  Ala Gly Ala Cys Cys  Thr Gly Gly
    2900                2905                2910

Ala Gly  Gly Ala Gly Gly Ala  Gly Ala Thr Ala Thr  Gly Ala Gly
    2915                2920                2925

Gly Gly  Ala Cys Ala Ala Thr  Thr Gly Gly Ala Gly  Ala Ala Gly
    2930                2935                2940

Thr Gly  Ala Ala Thr Thr Ala  Thr Ala Thr Ala Ala  Ala Thr Ala
    2945                2950                2955

Thr Ala  Ala Ala Gly Thr Ala  Gly Thr Ala Ala Ala  Ala Ala Thr
    2960                2965                2970

Thr Gly  Ala Ala Cys Cys Ala  Thr Thr Ala Gly Gly  Ala Gly Thr
    2975                2980                2985

Ala Gly  Cys Ala Cys Cys Cys  Ala Cys Cys Ala Ala  Gly Gly Cys
    2990                2995                3000
```

```
Ala Ala Ala Gly Ala Gly Ala Ala Gly Ala Gly Thr Gly Gly Thr
3005                3010                3015

Gly Cys Ala Gly Ala Gly Ala Gly Ala Ala Ala Ala Ala Gly
3020                3025                3030

Ala Gly Cys Ala Gly Thr Gly Gly Gly Ala Ala Thr Ala Gly Gly
3035                3040                3045

Ala Gly Cys Thr Thr Thr Gly Thr Thr Cys Cys Thr Thr Gly Gly
3050                3055                3060

Gly Thr Thr Cys Thr Thr Gly Gly Ala Gly Cys Ala Gly Cys
3065                3070                3075

Ala Gly Gly Ala Ala Gly Cys Ala Cys Thr Ala Thr Gly Gly Gly
3080                3085                3090

Cys Gly Cys Ala Gly Cys Gly Thr Cys Ala Ala Thr Gly Ala Cys
3095                3100                3105

Gly Cys Thr Gly Ala Cys Gly Gly Thr Ala Cys Ala Gly Gly Cys
3110                3115                3120

Cys Ala Gly Ala Cys Ala Ala Thr Thr Ala Thr Thr Gly Thr Cys
3125                3130                3135

Thr Gly Gly Thr Ala Thr Ala Gly Thr Gly Cys Ala Gly Cys Ala
3140                3145                3150

Gly Cys Ala Gly Ala Ala Cys Ala Ala Thr Thr Thr Gly Cys Thr
3155                3160                3165

Gly Ala Gly Gly Gly Cys Thr Ala Thr Thr Gly Ala Gly Gly Cys
3170                3175                3180

Gly Cys Ala Ala Cys Ala Gly Cys Ala Thr Cys Thr Gly Thr Thr
3185                3190                3195

Gly Cys Ala Ala Cys Thr Cys Ala Cys Ala Gly Thr Cys Thr Gly
3200                3205                3210

Gly Gly Gly Cys Ala Thr Cys Ala Ala Gly Cys Ala Gly Cys Thr
3215                3220                3225

Cys Cys Ala Gly Gly Cys Ala Ala Gly Ala Ala Thr Cys Cys Thr
3230                3235                3240

Gly Gly Cys Thr Gly Thr Gly Gly Ala Ala Ala Gly Ala Thr Ala
3245                3250                3255

Cys Cys Thr Ala Ala Ala Gly Gly Ala Thr Cys Ala Ala Cys Ala
3260                3265                3270

Gly Cys Thr Cys Cys Thr Gly Gly Gly Ala Thr Thr Thr Gly
3275                3280                3285

Gly Gly Gly Thr Thr Gly Cys Thr Cys Thr Gly Gly Ala Ala Ala
3290                3295                3300

Ala Cys Thr Cys Ala Thr Thr Thr Gly Cys Ala Cys Cys Ala Cys
3305                3310                3315

Thr Gly Cys Thr Gly Thr Cys Cys Thr Thr Gly Gly Ala Ala
3320                3325                3330

Thr Gly Cys Thr Ala Gly Thr Thr Gly Gly Ala Gly Thr Ala Ala
3335                3340                3345

Thr Ala Ala Ala Thr Cys Thr Cys Thr Gly Gly Ala Ala Cys Ala
3350                3355                3360

Gly Ala Thr Thr Thr Gly Gly Ala Ala Thr Cys Ala Cys Ala Cys
3365                3370                3375

Gly Ala Cys Cys Thr Gly Gly Ala Thr Gly Gly Ala Gly Thr Gly
3380                3385                3390
```

-continued

```
Gly Gly Ala Cys Ala Gly Ala Gly Ala Ala Thr  Thr Ala Ala
    3395            3400            3405

Cys Ala Ala Thr Thr Ala Cys  Ala Cys Ala Ala Gly  Cys Thr Thr
    3410            3415            3420

Ala Ala Thr Ala Cys Ala Cys  Thr Cys Cys Thr Thr  Ala Ala Thr
    3425            3430            3435

Thr Gly Ala Ala Gly Ala Ala  Thr Cys Gly Cys Ala  Ala Ala Ala
    3440            3445            3450

Cys Cys Ala Gly Cys Ala Ala  Gly Ala Ala Ala Gly  Ala Ala
    3455            3460            3465

Thr Gly Ala Ala Cys Ala Ala  Gly Ala Ala Thr Thr  Ala Thr Thr
    3470            3475            3480

Gly Gly Ala Ala Thr Thr Ala  Gly Ala Thr Ala Ala  Ala Thr Gly
    3485            3490            3495

Gly Gly Cys Ala Ala Gly Thr  Thr Thr Gly Thr Gly  Gly Ala Ala
    3500            3505            3510

Thr Thr Gly Gly Thr Thr Thr  Ala Ala Cys Ala Thr  Ala Ala Cys
    3515            3520            3525

Ala Ala Ala Thr Thr Gly Gly  Cys Thr Gly Thr Gly  Gly Thr Ala
    3530            3535            3540

Thr Ala Thr Ala Ala Ala Ala  Thr Thr Ala Thr Thr  Cys Ala Thr
    3545            3550            3555

Ala Ala Thr Gly Ala Thr Ala  Gly Thr Ala Gly Gly  Ala Gly Gly
    3560            3565            3570

Cys Thr Thr Gly Gly Thr Ala  Gly Gly Thr Thr Thr  Ala Ala Gly
    3575            3580            3585

Ala Ala Thr Ala Gly Thr Thr  Thr Thr Thr Gly Cys  Thr Gly Thr
    3590            3595            3600

Ala Cys Thr Thr Thr Cys Thr  Ala Thr Ala Gly Thr  Gly Ala Ala
    3605            3610            3615

Thr Ala Gly Ala Gly Thr Thr  Ala Gly Gly Cys Ala  Gly Gly Gly
    3620            3625            3630

Ala Thr Ala Thr Thr Cys Ala  Cys Cys Ala Thr Thr  Ala Thr Cys
    3635            3640            3645

Gly Thr Thr Thr Cys Ala Gly  Ala Cys Cys Cys Ala  Cys Cys Thr
    3650            3655            3660

Cys Cys Cys Ala Ala Cys Cys  Cys Cys Gly Ala Gly  Gly Gly Gly
    3665            3670            3675

Ala Cys Cys Cys Gly Ala Cys  Ala Gly Gly Cys Cys  Cys Gly Ala
    3680            3685            3690

Ala Gly Gly Ala Ala Thr Ala  Gly Ala Ala Gly Ala  Ala Gly Ala
    3695            3700            3705

Ala Gly Gly Thr Gly Gly Ala  Gly Ala Gly Ala Gly  Ala Gly Ala
    3710            3715            3720

Cys Ala Gly Ala Gly Ala Cys  Ala Gly Ala Thr Cys  Cys Ala Thr
    3725            3730            3735

Thr Cys Gly Ala Thr Thr Ala  Gly Thr Gly Ala Ala  Cys Gly Gly
    3740            3745            3750

Ala Thr Cys Thr Cys Gly Ala  Cys Gly Gly Thr Ala  Thr Cys Gly
    3755            3760            3765

Ala Thr Thr Ala Gly Ala Cys  Thr Gly Thr Ala Gly  Cys Cys Cys
    3770            3775            3780

Ala Gly Gly Ala Ala Thr Ala  Thr Gly Gly Cys Ala  Gly Cys Thr
```

```
                    3785              3790              3795

Ala Gly Ala Thr Thr Gly Thr Ala Cys Ala Cys Ala Thr Thr Thr
    3800              3805              3810

Ala Gly Ala Ala Gly Gly Ala Ala Ala Gly Thr Thr Ala Thr
    3815              3820              3825

Cys Thr Thr Gly Gly Thr Ala Gly Cys Ala Gly Thr Thr Cys Ala
    3830              3835              3840

Thr Gly Thr Ala Gly Cys Cys Ala Gly Thr Gly Ala Thr Ala
    3845              3850              3855

Thr Ala Thr Ala Gly Ala Ala Gly Cys Ala Gly Ala Ala Gly Thr
    3860              3865              3870

Ala Ala Thr Thr Cys Cys Ala Gly Cys Ala Gly Ala Gly Ala Cys
    3875              3880              3885

Ala Gly Gly Gly Cys Ala Ala Gly Ala Ala Ala Cys Ala Gly Cys
    3890              3895              3900

Ala Thr Ala Cys Thr Thr Cys Cys Thr Cys Thr Thr Ala Ala Ala
    3905              3910              3915

Ala Thr Thr Ala Gly Cys Ala Gly Gly Ala Ala Gly Ala Thr Gly
    3920              3925              3930

Gly Cys Cys Ala Gly Thr Ala Ala Ala Ala Cys Ala Gly Thr
    3935              3940              3945

Ala Cys Ala Thr Ala Cys Ala Gly Ala Cys Ala Ala Thr Gly Gly
    3950              3955              3960

Cys Ala Gly Cys Ala Ala Thr Thr Thr Cys Ala Cys Cys Ala Gly
    3965              3970              3975

Thr Ala Cys Thr Ala Cys Ala Gly Thr Thr Ala Ala Gly Gly Cys
    3980              3985              3990

Cys Gly Cys Cys Thr Gly Thr Thr Gly Gly Thr Gly Gly Gly Cys
    3995              4000              4005

Gly Gly Gly Gly Ala Thr Cys Ala Ala Gly Cys Ala Gly Gly Ala
    4010              4015              4020

Ala Thr Thr Thr Gly Gly Cys Ala Thr Thr Cys Cys Cys Thr Ala
    4025              4030              4035

Cys Ala Ala Thr Cys Cys Cys Cys Ala Ala Ala Gly Thr Cys Ala
    4040              4045              4050

Ala Gly Gly Ala Gly Thr Ala Ala Thr Ala Gly Ala Ala Thr Cys
    4055              4060              4065

Thr Ala Thr Gly Ala Ala Thr Ala Ala Ala Gly Ala Ala Thr Thr
    4070              4075              4080

Ala Ala Ala Gly Ala Ala Ala Ala Thr Thr Ala Thr Ala Gly Gly
    4085              4090              4095

Ala Cys Ala Gly Gly Thr Ala Ala Gly Ala Gly Ala Thr Cys Ala
    4100              4105              4110

Gly Gly Cys Thr Gly Ala Ala Cys Ala Thr Cys Thr Thr Ala Ala
    4115              4120              4125

Gly Ala Cys Ala Gly Cys Ala Gly Thr Ala Cys Ala Ala Ala Thr
    4130              4135              4140

Gly Gly Cys Ala Gly Thr Ala Thr Thr Cys Ala Thr Cys Cys Ala
    4145              4150              4155

Cys Ala Ala Thr Thr Thr Thr Ala Ala Ala Ala Gly Ala Ala Ala
    4160              4165              4170

Ala Gly Gly Gly Gly Gly Gly Ala Thr Thr Gly Gly Gly Gly Gly
    4175              4180              4185
```

```
Gly Thr Ala Cys Ala Gly Thr Gly Cys Ala Gly Gly Gly Ala
    4190            4195            4200

Ala Ala Gly Ala Ala Thr Ala Gly Thr Ala Gly Ala Cys Ala Thr
    4205            4210            4215

Ala Ala Thr Ala Gly Cys Ala Ala Cys Ala Gly Ala Cys Ala Thr
    4220            4225            4230

Ala Cys Ala Ala Ala Cys Thr Ala Ala Ala Gly Ala Ala Thr Thr
    4235            4240            4245

Ala Cys Ala Ala Ala Ala Ala Cys Ala Ala Thr Thr Ala Cys
    4250            4255            4260

Ala Ala Ala Ala Ala Thr Thr Cys Ala Ala Ala Ala Thr Thr Thr
    4265            4270            4275

Thr Cys Gly Gly Gly Thr Thr Thr Ala Thr Thr Ala Cys Ala Gly
    4280            4285            4290

Gly Gly Ala Cys Ala Gly Cys Ala Gly Ala Gly Ala Thr Cys Cys
    4295            4300            4305

Ala Gly Thr Thr Thr Gly Gly Cys Thr Gly Cys Ala Thr Ala Cys
    4310            4315            4320

Gly Cys Gly Thr Cys Gly Thr Gly Ala Gly Gly Cys Thr Cys Cys
    4325            4330            4335

Gly Gly Thr Gly Cys Cys Cys Gly Thr Cys Ala Gly Thr Gly Gly
    4340            4345            4350

Gly Cys Ala Gly Ala Gly Cys Gly Cys Ala Cys Ala Thr Cys Gly
    4355            4360            4365

Cys Cys Cys Ala Cys Ala Gly Thr Cys Cys Cys Cys Gly Ala Gly
    4370            4375            4380

Ala Ala Gly Thr Thr Gly Gly Gly Gly Gly Ala Gly Gly Gly
    4385            4390            4395

Gly Thr Cys Gly Gly Cys Ala Ala Thr Thr Gly Ala Ala Cys Cys
    4400            4405            4410

Gly Gly Thr Gly Cys Cys Thr Ala Gly Ala Gly Ala Ala Gly Gly
    4415            4420            4425

Thr Gly Gly Cys Gly Cys Gly Gly Gly Thr Ala Ala Ala Cys
    4430            4435            4440

Thr Gly Gly Gly Ala Ala Ala Gly Thr Gly Ala Thr Gly Thr Cys
    4445            4450            4455

Gly Thr Gly Thr Ala Cys Thr Gly Gly Cys Thr Cys Cys Gly Cys
    4460            4465            4470

Cys Thr Thr Thr Thr Thr Cys Cys Cys Gly Ala Gly Gly Gly Thr
    4475            4480            4485

Gly Gly Gly Gly Gly Ala Gly Ala Ala Cys Cys Gly Thr Ala Thr
    4490            4495            4500

Ala Thr Ala Ala Gly Thr Gly Cys Ala Gly Thr Ala Gly Thr Cys
    4505            4510            4515

Gly Cys Cys Gly Thr Gly Ala Ala Cys Gly Thr Thr Cys Thr Thr
    4520            4525            4530

Thr Thr Thr Cys Gly Cys Ala Ala Cys Gly Gly Gly Thr Thr Thr
    4535            4540            4545

Gly Cys Cys Gly Cys Cys Ala Gly Ala Ala Cys Ala Cys Ala Gly
    4550            4555            4560

Gly Thr Ala Ala Gly Thr Gly Cys Cys Gly Thr Gly Thr Gly Thr
    4565            4570            4575
```

```
Gly Gly Thr Thr Cys Cys Cys Gly Cys Gly Gly Cys Cys Thr
        4580            4585                4590

Gly Gly Cys Cys Thr Cys Thr Thr Thr Ala Cys Gly Gly Thr
        4595            4600                4605

Thr Ala Thr Gly Gly Cys Cys Cys Thr Thr Gly Cys Gly Thr Gly
        4610            4615                4620

Cys Cys Thr Thr Gly Ala Ala Thr Thr Ala Cys Thr Thr Cys Cys
        4625            4630                4635

Ala Cys Cys Thr Gly Gly Cys Thr Gly Cys Ala Gly Thr Ala Cys
        4640            4645                4650

Gly Thr Gly Ala Thr Thr Cys Thr Thr Gly Ala Thr Cys Cys Cys
        4655            4660                4665

Gly Ala Gly Cys Thr Thr Cys Gly Gly Gly Thr Thr Gly Gly Ala
        4670            4675                4680

Ala Gly Thr Gly Gly Gly Thr Gly Gly Gly Ala Gly Ala Gly Thr
        4685            4690                4695

Thr Cys Gly Ala Gly Gly Cys Cys Thr Gly Cys Gly Cys Gly Thr
        4700            4705                4710

Thr Ala Ala Gly Gly Ala Gly Cys Cys Cys Cys Thr Thr Cys Gly
        4715            4720                4725

Cys Cys Thr Cys Gly Thr Gly Cys Thr Thr Gly Ala Gly Thr Thr
        4730            4735                4740

Gly Ala Gly Gly Cys Cys Thr Gly Gly Cys Cys Thr Gly Gly Gly
        4745            4750                4755

Cys Gly Cys Thr Gly Gly Gly Gly Cys Cys Gly Cys Cys Gly Cys
        4760            4765                4770

Gly Thr Gly Cys Gly Ala Ala Thr Cys Thr Gly Gly Thr Gly Gly
        4775            4780                4785

Cys Ala Cys Cys Thr Thr Cys Gly Cys Gly Cys Cys Thr Gly Thr
        4790            4795                4800

Cys Thr Cys Gly Cys Thr Gly Cys Thr Thr Cys Gly Ala Thr
        4805            4810                4815

Ala Ala Gly Thr Cys Thr Cys Thr Ala Gly Cys Cys Ala Thr Thr
        4820            4825                4830

Thr Ala Ala Ala Ala Thr Thr Thr Thr Thr Gly Ala Thr Gly Ala
        4835            4840                4845

Cys Cys Thr Gly Cys Thr Gly Cys Gly Ala Cys Gly Cys Thr Thr
        4850            4855                4860

Thr Thr Thr Thr Thr Cys Thr Gly Gly Cys Ala Ala Gly Ala Thr
        4865            4870                4875

Ala Gly Thr Cys Thr Thr Gly Thr Ala Ala Ala Thr Gly Cys Gly
        4880            4885                4890

Gly Gly Cys Cys Ala Ala Gly Ala Thr Cys Thr Gly Cys Ala Cys
        4895            4900                4905

Ala Cys Thr Gly Gly Thr Ala Thr Thr Thr Cys Gly Gly Thr Thr
        4910            4915                4920

Thr Thr Thr Gly Gly Gly Gly Cys Cys Gly Cys Gly Gly Gly Cys
        4925            4930                4935

Gly Gly Cys Gly Ala Cys Gly Gly Gly Cys Cys Cys Gly Thr
        4940            4945                4950

Gly Cys Gly Thr Cys Cys Cys Ala Gly Cys Gly Cys Ala Cys Ala
        4955            4960                4965

Thr Gly Thr Thr Cys Gly Gly Cys Gly Ala Gly Gly Cys Gly Gly
```

-continued

```
            4970                4975                4980
Gly Gly Cys Cys Thr Gly Cys Gly Ala Gly Cys Gly Cys Gly Gly
        4985                4990                4995
Cys Cys Ala Cys Cys Gly Ala Gly Ala Ala Thr Cys Gly Gly Ala
        5000                5005                5010
Cys Gly Gly Gly Gly Gly Thr Ala Gly Thr Cys Thr Cys Ala Ala
        5015                5020                5025
Gly Cys Thr Gly Gly Cys Cys Gly Gly Cys Cys Thr Gly Cys Thr
        5030                5035                5040
Cys Thr Gly Gly Thr Gly Cys Cys Thr Gly Gly Cys Cys Thr Cys
        5045                5050                5055
Gly Cys Gly Cys Cys Gly Cys Cys Gly Thr Gly Thr Ala Thr Cys
        5060                5065                5070
Gly Cys Cys Cys Gly Cys Cys Cys Thr Gly Gly Gly Cys Gly Gly
        5075                5080                5085
Gly Cys Ala Ala Gly Gly Cys Thr Gly Gly Cys Cys Cys Gly Gly
        5090                5095                5100
Thr Cys Gly Gly Cys Ala Cys Cys Ala Gly Thr Thr Gly Cys Gly
        5105                5110                5115
Thr Gly Ala Gly Cys Gly Gly Ala Ala Ala Gly Ala Thr Gly Gly
        5120                5125                5130
Cys Cys Gly Cys Thr Thr Cys Cys Cys Gly Gly Cys Cys Cys Thr
        5135                5140                5145
Gly Cys Thr Gly Cys Ala Gly Gly Gly Ala Gly Cys Thr Cys Ala
        5150                5155                5160
Ala Ala Ala Thr Gly Gly Ala Gly Gly Ala Cys Gly Cys Gly Gly
        5165                5170                5175
Cys Gly Cys Thr Cys Gly Gly Gly Ala Gly Ala Gly Cys Gly Gly
        5180                5185                5190
Gly Cys Gly Gly Gly Thr Gly Ala Gly Thr Cys Ala Cys Cys Cys
        5195                5200                5205
Ala Cys Ala Cys Ala Ala Ala Gly Gly Ala Ala Ala Ala Gly Gly
        5210                5215                5220
Gly Cys Cys Thr Thr Thr Cys Cys Gly Thr Cys Cys Thr Cys Ala
        5225                5230                5235
Gly Cys Cys Gly Thr Cys Gly Cys Thr Thr Cys Ala Thr Gly Thr
        5240                5245                5250
Gly Ala Cys Thr Cys Cys Ala Cys Thr Gly Ala Gly Thr Ala Cys
        5255                5260                5265
Cys Gly Gly Gly Cys Gly Cys Cys Gly Thr Cys Cys Ala Gly Gly
        5270                5275                5280
Cys Ala Cys Cys Thr Cys Gly Ala Thr Thr Ala Gly Thr Thr Cys
        5285                5290                5295
Thr Cys Gly Thr Gly Cys Thr Thr Thr Gly Gly Ala Gly Gly Thr
        5300                5305                5310
Ala Cys Gly Thr Cys Gly Thr Cys Thr Thr Thr Ala Gly Gly Thr
        5315                5320                5325
Thr Gly Gly Gly Gly Gly Ala Gly Gly Gly Thr Thr Thr Thr Thr
        5330                5335                5340
Thr Ala Thr Gly Cys Gly Ala Thr Gly Gly Ala Gly Thr Thr Thr
        5345                5350                5355
Cys Cys Cys Cys Ala Cys Ala Cys Thr Gly Ala Gly Thr Gly Gly
        5360                5365                5370
```

```
Gly Thr Gly Gly Ala Gly Ala Cys Thr Gly Ala Ala Gly Thr Thr
    5375            5380                5385
Ala Gly Gly Cys Cys Ala Gly Cys Thr Gly Gly Cys Ala Cys
    5390            5395                5400
Thr Thr Gly Ala Thr Gly Thr Ala Ala Thr Thr Cys Thr Cys Cys
    5405            5410                5415
Thr Thr Gly Gly Ala Ala Thr Thr Gly Cys Cys Cys Thr Thr
    5420            5425                5430
Thr Thr Thr Gly Ala Gly Thr Thr Thr Gly Gly Ala Thr Cys Thr
    5435            5440                5445
Thr Gly Gly Thr Thr Cys Ala Thr Thr Cys Thr Cys Ala Ala Gly
    5450            5455                5460
Cys Cys Thr Cys Ala Gly Ala Cys Ala Gly Thr Gly Gly Thr Thr
    5465            5470                5475
Cys Ala Ala Ala Gly Thr Thr Thr Thr Thr Thr Cys Thr Thr
    5480            5485                5490
Cys Cys Ala Thr Thr Thr Cys Ala Gly Gly Thr Gly Thr Cys Gly
    5495            5500                5505
Thr Gly Ala Gly Cys Thr Ala Gly Cys Thr Cys Thr Ala Gly Ala
    5510            5515                5520
Gly Cys Cys Ala Cys Cys Ala Thr Gly Gly Thr Gly Ala Gly Cys
    5525            5530                5535
Ala Ala Gly Gly Gly Cys Gly Ala Gly Gly Ala Gly Cys Thr Gly
    5540            5545                5550
Thr Thr Cys Ala Cys Cys Gly Gly Gly Gly Thr Gly Gly Thr Gly
    5555            5560                5565
Cys Cys Cys Ala Thr Cys Cys Thr Gly Gly Thr Cys Gly Ala Gly
    5570            5575                5580
Cys Thr Gly Gly Ala Cys Gly Gly Cys Gly Ala Cys Gly Thr Ala
    5585            5590                5595
Ala Ala Cys Gly Gly Cys Cys Ala Cys Ala Ala Gly Thr Thr Cys
    5600            5605                5610
Ala Gly Cys Gly Thr Gly Thr Cys Cys Gly Gly Cys Gly Ala Gly
    5615            5620                5625
Gly Gly Cys Gly Ala Gly Gly Gly Cys Gly Ala Thr Gly Cys Cys
    5630            5635                5640
Ala Cys Cys Thr Ala Cys Gly Gly Cys Ala Ala Gly Cys Thr Gly
    5645            5650                5655
Ala Cys Cys Cys Thr Gly Ala Ala Gly Thr Thr Cys Ala Thr Cys
    5660            5665                5670
Thr Gly Cys Ala Cys Cys Ala Cys Cys Gly Gly Cys Ala Ala Gly
    5675            5680                5685
Cys Thr Gly Cys Cys Cys Gly Thr Gly Cys Cys Cys Thr Gly Gly
    5690            5695                5700
Cys Cys Cys Ala Cys Cys Cys Thr Cys Gly Thr Gly Ala Cys Cys
    5705            5710                5715
Ala Cys Cys Cys Thr Gly Ala Cys Cys Thr Ala Cys Gly Gly Cys
    5720            5725                5730
Gly Thr Gly Cys Ala Gly Thr Gly Cys Thr Thr Cys Ala Gly Cys
    5735            5740                5745
Cys Gly Cys Thr Ala Cys Cys Cys Cys Gly Ala Cys Cys Ala Cys
    5750            5755                5760
```

-continued

```
Ala Thr  Gly Ala Ala Gly Cys  Ala Gly Cys Ala Cys  Gly Ala Cys
    5765                 5770                 5775

Thr Thr  Cys Thr Thr Cys Ala  Ala Gly Thr Cys Cys  Gly Cys Cys
    5780                 5785                 5790

Ala Thr  Gly Cys Cys Cys Gly  Ala Ala Gly Gly Cys  Thr Ala Cys
    5795                 5800                 5805

Gly Thr  Cys Cys Ala Gly Gly  Ala Gly Cys Gly Cys  Ala Cys Cys
    5810                 5815                 5820

Ala Thr  Cys Thr Thr Cys Thr  Thr Cys Ala Ala Gly  Gly Ala Cys
    5825                 5830                 5835

Gly Ala  Cys Gly Gly Cys Ala  Ala Cys Thr Ala Cys  Ala Ala Gly
    5840                 5845                 5850

Ala Cys  Cys Cys Gly Cys Gly  Cys Cys Gly Ala Gly  Gly Thr Gly
    5855                 5860                 5865

Ala Ala  Gly Thr Thr Cys Gly  Ala Gly Gly Gly Cys  Gly Ala Cys
    5870                 5875                 5880

Ala Cys  Cys Cys Thr Gly Gly  Thr Gly Ala Ala Cys  Cys Gly Cys
    5885                 5890                 5895

Ala Thr  Cys Gly Ala Gly Cys  Thr Gly Ala Ala Gly  Gly Gly Cys
    5900                 5905                 5910

Ala Thr  Cys Gly Ala Cys Thr  Thr Cys Ala Ala Gly  Gly Ala Gly
    5915                 5920                 5925

Gly Ala  Cys Gly Gly Cys Ala  Ala Cys Ala Thr Cys  Cys Thr Gly
    5930                 5935                 5940

Gly Gly  Gly Cys Ala Cys Ala  Ala Gly Cys Thr Gly  Gly Ala Gly
    5945                 5950                 5955

Thr Ala  Cys Ala Ala Cys Thr  Ala Cys Ala Ala Cys  Ala Gly Cys
    5960                 5965                 5970

Cys Ala  Cys Ala Ala Cys Gly  Thr Cys Thr Ala Thr  Ala Thr Cys
    5975                 5980                 5985

Ala Thr  Gly Gly Cys Cys Gly  Ala Cys Ala Ala Gly  Cys Ala Gly
    5990                 5995                 6000

Ala Ala  Gly Ala Ala Cys Gly  Gly Cys Ala Thr Cys  Ala Ala Gly
    6005                 6010                 6015

Gly Thr  Gly Ala Ala Cys Thr  Thr Cys Ala Ala Gly  Ala Thr Cys
    6020                 6025                 6030

Cys Gly  Cys Cys Ala Cys Ala  Ala Cys Ala Thr Cys  Gly Ala Gly
    6035                 6040                 6045

Gly Ala  Cys Gly Gly Cys Ala  Gly Cys Gly Thr Gly  Cys Ala Gly
    6050                 6055                 6060

Cys Thr  Cys Gly Cys Cys Gly  Ala Cys Cys Ala Cys  Thr Ala Cys
    6065                 6070                 6075

Cys Ala  Gly Cys Ala Gly Ala  Ala Cys Ala Cys Cys  Cys Cys Cys
    6080                 6085                 6090

Ala Thr  Cys Gly Gly Cys Gly  Ala Cys Gly Gly Cys  Cys Cys Cys
    6095                 6100                 6105

Gly Thr  Gly Cys Thr Gly Cys  Thr Gly Cys Cys Cys  Gly Ala Cys
    6110                 6115                 6120

Ala Ala  Cys Cys Ala Cys Thr  Ala Cys Cys Thr Gly  Ala Gly Cys
    6125                 6130                 6135

Ala Cys  Cys Cys Ala Gly Thr  Cys Cys Gly Cys Cys  Cys Thr Gly
    6140                 6145                 6150

Ala Gly  Cys Ala Ala Ala Gly  Ala Cys Cys Cys Cys  Ala Ala Cys
```

```
                        6155                6160                  6165

Gly Ala  Gly Ala Ala Gly  Cys Gly Cys Gly  Ala Thr  Cys Ala Cys
         6170                 6175                  6180

Ala Thr  Gly Gly Thr Cys  Cys Thr Gly Cys  Thr Gly  Gly Ala Gly
         6185                 6190                  6195

Thr Thr  Cys Gly Thr Gly  Ala Cys Cys Gly  Cys Cys  Gly Cys Cys
         6200                 6205                  6210

Gly Gly  Gly Ala Thr Cys  Ala Cys Thr Cys  Thr Cys  Gly Gly Cys
         6215                 6220                  6225

Ala Thr  Gly Gly Ala Cys  Gly Ala Gly Cys  Thr Gly  Thr Ala Cys
         6230                 6235                  6240

Ala Ala  Gly Thr Cys Cys  Gly Gly Ala Gly  Gly Cys  Ala Gly Cys
         6245                 6250                  6255

Gly Gly  Ala Gly Ala Gly  Gly Cys Ala Gly  Ala  Gly Gly Ala
         6260                 6265                  6270

Ala Gly  Thr Cys Thr Thr  Cys Thr Ala Ala  Cys Ala  Thr Gly Cys
         6275                 6280                  6285

Gly Gly  Thr Gly Ala Cys  Gly Thr Gly Gly  Ala Gly  Gly Ala Gly
         6290                 6295                  6300

Ala Ala  Thr Cys Cys Cys  Gly Gly Cys Cys  Cys Ala  Gly Gly Thr
         6305                 6310                  6315

Ala Cys  Ala Ala Cys Thr  Gly Cys Ala Gly  Cys Ala  Gly Thr Cys
         6320                 6325                  6330

Thr Gly  Gly Gly Cys Cys  Thr Gly Ala Gly  Cys Thr  Gly Gly Ala
         6335                 6340                  6345

Gly Ala  Ala Gly Cys Cys  Thr Gly Gly Cys  Gly Cys  Thr Thr Cys
         6350                 6355                  6360

Ala Gly  Thr Gly Ala Ala  Gly Ala Thr Ala  Thr Cys  Cys Thr Gly
         6365                 6370                  6375

Cys Ala  Ala Gly Gly Cys  Thr Cys Thr Gly  Gly  Thr Thr Ala
         6380                 6385                  6390

Cys Thr  Cys Ala Thr Thr  Cys Ala Cys Thr  Gly Cys  Thr Ala
         6395                 6400                  6405

Cys Ala  Cys Cys Ala Thr  Gly Ala Ala Cys  Thr Gly  Gly Gly Thr
         6410                 6415                  6420

Gly Ala  Ala Gly Cys Ala  Gly Ala Gly Cys  Cys Ala  Thr Gly Gly
         6425                 6430                  6435

Ala Ala  Ala Gly Ala Gly  Cys Thr Thr Gly  Ala Gly  Thr Gly
         6440                 6445                  6450

Gly Ala  Thr Thr Gly Gly  Ala Cys Thr Ala  Thr Thr  Thr Ala Cys
         6455                 6460                  6465

Thr Cys  Cys Thr Thr Ala  Cys Ala Ala Thr  Gly Gly  Thr Gly Cys
         6470                 6475                  6480

Thr Thr  Cys Thr Ala Gly  Cys Thr Ala Cys  Ala Ala  Cys Cys Ala
         6485                 6490                  6495

Gly Ala  Ala Gly Thr Thr  Cys Ala Gly Gly  Gly Gly  Cys Ala Ala
         6500                 6505                  6510

Gly Gly  Cys Cys Ala Cys  Ala Thr Thr Ala  Ala Cys  Thr Gly Thr
         6515                 6520                  6525

Ala Gly  Ala Cys Ala Ala  Gly Thr Cys Ala  Thr Cys  Cys Ala Gly
         6530                 6535                  6540

Cys Ala  Cys Ala Gly Cys  Cys Thr Ala Cys  Ala Thr  Gly Gly Ala
         6545                 6550                  6555
```

-continued

```
Cys Cys Thr Cys Cys Thr Cys Ala Gly Thr Cys Thr Gly Ala Cys
6560                6565                6570

Ala Thr Cys Thr Gly Ala Ala Gly Ala Cys Thr Cys Thr Gly Cys
6575                6580                6585

Ala Gly Thr Cys Thr Ala Thr Thr Thr Cys Thr Gly Thr Gly Cys
6590                6595                6600

Ala Ala Gly Gly Gly Gly Gly Gly Thr Thr Ala Cys Gly Ala
6605                6610                6615

Cys Gly Gly Gly Ala Gly Gly Gly Thr Thr Thr Gly Ala
6620                6625                6630

Cys Thr Ala Cys Thr Gly Gly Gly Cys Cys Ala Ala Gly Gly
6635                6640                6645

Gly Ala Cys Cys Ala Cys Gly Gly Thr Cys Ala Cys Cys Gly Thr
6650                6655                6660

Cys Thr Cys Cys Thr Cys Ala Gly Gly Thr Gly Ala Gly Gly
6665                6670                6675

Cys Gly Gly Thr Thr Cys Ala Gly Gly Cys Gly Gly Cys Gly Gly
6680                6685                6690

Thr Gly Gly Cys Thr Cys Thr Gly Gly Cys Gly Gly Thr Gly Gly
6695                6700                6705

Cys Gly Gly Ala Thr Cys Gly Gly Ala Cys Ala Thr Cys Gly Ala
6710                6715                6720

Gly Cys Thr Cys Ala Cys Thr Cys Ala Gly Thr Cys Thr Cys Cys
6725                6730                6735

Ala Gly Cys Ala Ala Thr Cys Ala Thr Gly Thr Cys Thr Gly Cys
6740                6745                6750

Ala Thr Cys Thr Cys Cys Ala Gly Gly Gly Gly Ala Gly Ala Ala
6755                6760                6765

Gly Gly Thr Cys Ala Cys Cys Ala Thr Gly Ala Cys Cys Thr Gly
6770                6775                6780

Cys Ala Gly Thr Gly Cys Cys Ala Gly Cys Thr Cys Ala Ala Gly
6785                6790                6795

Thr Gly Thr Ala Ala Gly Thr Thr Ala Cys Ala Thr Gly Cys Ala
6800                6805                6810

Cys Thr Gly Gly Thr Ala Cys Cys Ala Gly Cys Ala Gly Ala Ala
6815                6820                6825

Gly Thr Cys Ala Gly Gly Cys Ala Cys Cys Thr Cys Cys Cys Cys
6830                6835                6840

Cys Ala Ala Ala Gly Ala Thr Gly Gly Ala Thr Thr Thr Ala
6845                6850                6855

Thr Gly Ala Cys Ala Cys Ala Thr Cys Cys Ala Ala Ala Cys Thr
6860                6865                6870

Gly Gly Cys Thr Thr Cys Thr Gly Gly Ala Gly Thr Cys Cys Cys
6875                6880                6885

Ala Gly Gly Thr Cys Gly Cys Thr Thr Cys Ala Gly Thr Gly Gly
6890                6895                6900

Cys Ala Gly Thr Gly Gly Gly Thr Cys Thr Gly Gly Ala Ala Ala
6905                6910                6915

Cys Thr Cys Thr Thr Ala Cys Thr Cys Thr Cys Thr Cys Ala Cys
6920                6925                6930

Ala Ala Thr Cys Ala Gly Cys Ala Gly Cys Gly Thr Gly Gly Ala
6935                6940                6945
```

-continued

```
Gly Gly  Cys Thr Gly Ala Ala  Gly Ala Thr Gly Ala  Thr Gly Cys
    6950                 6955                 6960

Ala Ala  Cys Thr Thr Ala Thr  Thr Ala Cys Thr Gly  Cys Cys Ala
    6965                 6970                 6975

Gly Cys  Ala Gly Thr Gly Gly  Ala Gly Thr Gly Gly  Thr Thr Ala
    6980                 6985                 6990

Cys Cys  Cys Thr Cys Thr Cys  Ala Cys Gly Thr Thr  Cys Gly Gly
    6995                 7000                 7005

Thr Gly  Cys Thr Gly Gly Gly  Ala Cys Ala Ala Ala  Gly Thr Thr
    7010                 7015                 7020

Gly Gly  Ala Ala Ala Thr Cys  Ala Ala Ala Cys Cys  Ala Cys Gly
    7025                 7030                 7035

Ala Cys  Gly Cys Cys Ala Gly  Cys Gly Cys Cys Gly  Cys Gly Ala
    7040                 7045                 7050

Cys Cys  Ala Cys Cys Ala Ala  Cys Ala Cys Cys Gly  Gly Cys Gly
    7055                 7060                 7065

Cys Cys  Cys Ala Cys Cys Ala  Thr Cys Gly Cys Gly  Thr Cys Gly
    7070                 7075                 7080

Cys Ala  Gly Cys Cys Cys Cys  Thr Gly Thr Cys Cys  Cys Thr Gly
    7085                 7090                 7095

Cys Gly  Cys Cys Cys Ala Gly  Ala Gly Gly Cys Gly  Thr Gly Cys
    7100                 7105                 7110

Cys Gly  Gly Cys Cys Ala Gly  Cys Gly Gly Cys Gly  Gly Gly Gly
    7115                 7120                 7125

Gly Gly  Cys Gly Cys Ala Gly  Thr Gly Cys Ala Cys  Ala Cys Gly
    7130                 7135                 7140

Ala Gly  Gly Gly Gly Gly Cys  Thr Gly Gly Ala Cys  Thr Thr Cys
    7145                 7150                 7155

Gly Cys  Cys Thr Gly Thr Gly  Ala Thr Ala Thr Cys  Thr Ala Cys
    7160                 7165                 7170

Ala Thr  Cys Thr Gly Gly Gly  Cys Gly Cys Cys Cys  Thr Thr Gly
    7175                 7180                 7185

Gly Cys  Cys Gly Gly Gly Ala  Cys Thr Thr Gly Thr  Gly Gly Gly
    7190                 7195                 7200

Gly Thr  Cys Cys Thr Thr Cys  Thr Cys Cys Thr Gly  Thr Cys Ala
    7205                 7210                 7215

Cys Thr  Gly Gly Thr Thr Ala  Thr Cys Ala Cys Cys  Cys Thr Thr
    7220                 7225                 7230

Thr Ala  Cys Thr Gly Cys Ala  Ala Ala Gly Cys Cys  Thr Thr Thr
    7235                 7240                 7245

Ala Thr  Thr Ala Thr Thr Thr  Thr Cys Thr Gly Gly  Gly Thr Gly
    7250                 7255                 7260

Ala Gly  Gly Ala Gly Thr Ala  Ala Gly Ala Gly Gly  Ala Gly Cys
    7265                 7270                 7275

Ala Gly  Gly Cys Thr Cys Cys  Thr Gly Cys Ala Cys  Ala Gly Thr
    7280                 7285                 7290

Gly Ala  Cys Thr Ala Cys Ala  Thr Gly Ala Ala Cys  Ala Thr Gly
    7295                 7300                 7305

Ala Cys  Thr Cys Cys Cys Cys  Gly Cys Cys Gly Cys  Cys Cys Cys
    7310                 7315                 7320

Gly Gly  Gly Cys Cys Cys Ala  Cys Cys Cys Gly Cys  Ala Ala Gly
    7325                 7330                 7335

Cys Ala  Thr Thr Ala Cys Cys  Ala Gly Cys Cys Cys  Thr Ala Thr
```

Gly Cys Cys Cys Cys Ala Cys Cys Ala Cys Gly Cys Gly Ala Cys
7340        7345                7350
                     7355                7360                7365

Thr Thr Cys Gly Cys Ala Gly Cys Cys Thr Ala Thr Cys Gly Cys
        7370            7375                7380

Thr Cys Cys Cys Thr Gly Ala Gly Ala Gly Thr Gly Ala Ala Gly
        7385            7390            7395

Thr Thr Cys Ala Gly Cys Ala Gly Gly Ala Gly Cys Gly Cys Ala
        7400            7405            7410

Gly Ala Cys Gly Cys Cys Cys Cys Gly Cys Gly Thr Ala Cys
        7415            7420            7425

Cys Ala Gly Cys Ala Gly Gly Gly Cys Cys Ala Gly Ala Ala Cys
        7430            7435            7440

Cys Ala Gly Cys Thr Cys Thr Ala Thr Ala Ala Cys Gly Ala Gly
        7445            7450            7455

Cys Thr Cys Ala Ala Thr Cys Thr Ala Gly Gly Ala Cys Gly Ala
        7460            7465            7470

Ala Gly Ala Gly Ala Gly Gly Ala Gly Thr Ala Cys Gly Ala Thr
        7475            7480            7485

Gly Thr Thr Thr Gly Gly Ala Cys Ala Ala Gly Ala Gly Ala
        7490            7495            7500

Cys Gly Thr Gly Gly Cys Cys Gly Gly Gly Ala Cys Cys Cys Thr
        7505            7510            7515

Gly Ala Gly Ala Thr Gly Gly Gly Gly Gly Ala Ala Ala Gly
        7520            7525            7530

Cys Cys Gly Ala Gly Ala Ala Gly Gly Ala Ala Gly Ala Ala Cys
        7535            7540            7545

Cys Cys Thr Cys Ala Gly Gly Ala Ala Gly Gly Cys Cys Thr Gly
        7550            7555            7560

Thr Ala Cys Ala Ala Thr Gly Ala Ala Cys Thr Gly Cys Ala Gly
        7565            7570            7575

Ala Ala Ala Gly Ala Thr Ala Ala Gly Ala Thr Gly Gly Cys Gly
        7580            7585            7590

Gly Ala Gly Gly Cys Cys Thr Ala Cys Ala Gly Thr Gly Ala Gly
        7595            7600            7605

Ala Thr Thr Gly Gly Gly Ala Thr Gly Ala Ala Ala Gly Gly Cys
        7610            7615            7620

Gly Ala Gly Cys Gly Cys Cys Gly Gly Ala Gly Gly Gly Cys
        7625            7630            7635

Ala Ala Gly Gly Gly Gly Cys Ala Cys Gly Ala Thr Gly Gly Cys
        7640            7645            7650

Cys Thr Thr Thr Ala Cys Cys Ala Gly Gly Gly Thr Cys Thr Cys
        7655            7660            7665

Ala Gly Thr Ala Cys Ala Gly Cys Cys Ala Cys Cys Ala Ala Gly
        7670            7675            7680

Gly Ala Cys Ala Cys Cys Thr Ala Cys Gly Ala Cys Gly Cys Cys
        7685            7690            7695

Cys Thr Thr Cys Ala Cys Ala Thr Gly Cys Ala Gly Gly Cys Cys
        7700            7705            7710

Cys Thr Gly Cys Cys Cys Cys Thr Cys Gly Cys Thr Cys Gly
        7715            7720            7725

Ala Cys Ala Ala Thr Cys Ala Ala Cys Cys Thr Cys Thr Gly Gly
        7730            7735            7740

Ala Thr Thr Ala Cys Ala Ala Ala Thr Thr Thr Gly Thr Gly
              7745            7750               7755

Ala Ala Ala Gly Ala Thr Thr Gly Ala Cys Thr Gly Thr Ala
    7760            7765              7770

Thr Thr Cys Thr Thr Ala Ala Cys Thr Ala Thr Gly Thr Thr Gly
    7775            7780              7785

Cys Thr Cys Cys Thr Thr Thr Ala Cys Gly Cys Thr Ala Thr
    7790            7795              7800

Gly Thr Gly Gly Ala Thr Ala Cys Gly Cys Thr Gly Cys Thr Thr
    7805            7810              7815

Thr Ala Ala Thr Gly Cys Cys Thr Thr Thr Gly Thr Ala Thr Cys
    7820            7825              7830

Ala Thr Gly Cys Thr Ala Thr Thr Gly Cys Thr Cys Cys Cys
    7835            7840              7845

Gly Thr Ala Thr Gly Gly Cys Thr Thr Thr Cys Ala Thr Thr Thr
7850 7855 7860

Thr Cys Thr Cys Cys Thr Cys Cys Thr Thr Gly Thr Ala Thr Ala
7865 7870 7875

Ala Ala Thr Cys Cys Thr Gly Gly Thr Thr Gly Cys Thr Gly Thr
7880 7885 7890

Cys Thr Cys Thr Thr Thr Ala Thr Gly Ala Gly Gly Ala Gly Thr
7895 7900 7905

Thr Gly Thr Gly Gly Cys Cys Cys Gly Thr Thr Gly Thr Cys Ala
7910 7915 7920

Gly Gly Cys Ala Ala Cys Gly Thr Gly Gly Cys Gly Thr Gly Gly
7925 7930 7935

Thr Gly Thr Gly Cys Ala Cys Thr Gly Thr Gly Thr Thr Thr Gly
7940 7945 7950

Cys Thr Gly Ala Cys Gly Cys Ala Ala Cys Cys Cys Cys Cys Ala
7955 7960 7965

Cys Thr Gly Gly Thr Thr Gly Gly Gly Gly Cys Ala Thr Thr Gly
7970 7975 7980

Cys Cys Ala Cys Cys Ala Cys Cys Thr Gly Thr Cys Ala Gly Cys
7985 7990 7995

Thr Cys Cys Thr Thr Thr Cys Cys Gly Gly Gly Ala Cys Thr Thr
8000 8005 8010

Thr Cys Gly Cys Thr Thr Thr Cys Cys Cys Cys Cys Thr Cys Cys
8015 8020 8025

Cys Thr Ala Thr Thr Gly Cys Cys Ala Cys Gly Gly Cys Gly Gly
8030 8035 8040

Ala Ala Cys Thr Cys Ala Thr Cys Gly Cys Cys Gly Cys Cys Thr
8045 8050 8055

Gly Cys Cys Thr Thr Gly Cys Cys Cys Gly Cys Thr Gly Cys Thr
8060 8065 8070

Gly Gly Ala Cys Ala Gly Gly Gly Gly Cys Thr Cys Gly Gly Cys
8075 8080 8085

Thr Gly Thr Thr Gly Gly Gly Cys Ala Cys Thr Gly Ala Cys Ala
8090 8095 8100

Ala Thr Thr Cys Cys Gly Thr Gly Gly Thr Gly Thr Thr Gly Thr
8105 8110 8115

Cys Gly Gly Gly Gly Ala Ala Gly Cys Thr Gly Ala Cys Gly Thr
8120 8125 8130

```
Cys Cys Thr Thr Thr Cys Cys Thr Thr Gly Gly Cys Thr Gly Cys
    8135            8140            8145

Thr Cys Gly Cys Cys Thr Gly Thr Gly Thr Thr Gly Cys Cys Ala
    8150            8155            8160

Cys Cys Thr Gly Gly Ala Thr Thr Cys Thr Gly Cys Gly Cys Gly
    8165            8170            8175

Gly Gly Ala Cys Gly Thr Cys Cys Thr Thr Cys Thr Gly Cys Thr
    8180            8185            8190

Ala Cys Gly Thr Cys Cys Cys Thr Thr Cys Gly Gly Cys Cys Cys
    8195            8200            8205

Thr Cys Ala Ala Thr Cys Cys Ala Gly Cys Gly Gly Ala Cys Cys
    8210            8215            8220

Thr Thr Cys Cys Thr Cys Cys Cys Gly Cys Gly Gly Cys Cys
    8225            8230            8235

Thr Gly Cys Thr Gly Cys Cys Gly Gly Cys Thr Cys Thr Gly Cys
    8240            8245            8250

Gly Gly Cys Cys Thr Cys Thr Thr Cys Cys Gly Cys Gly Thr Cys
    8255            8260            8265

Thr Thr Cys Gly Cys Cys Thr Thr Cys Gly Cys Cys Cys Thr Cys
    8270            8275            8280

Ala Gly Ala Cys Gly Ala Gly Thr Cys Gly Gly Ala Thr Cys Thr
    8285            8290            8295

Cys Cys Cys Thr Thr Thr Gly Gly Gly Cys Cys Gly Cys Cys Thr
    8300            8305            8310

Cys Cys Cys Cys Gly Cys Cys Thr Gly Gly Ala Ala Thr Thr Cys
    8315            8320            8325

Gly Ala Gly Cys Thr Cys Gly Gly Thr Ala Cys Cys Thr Thr Thr
    8330            8335            8340

Ala Ala Gly Ala Cys Cys Ala Ala Thr Gly Ala Cys Thr Thr Ala
    8345            8350            8355

Cys Ala Ala Gly Gly Cys Ala Gly Cys Thr Gly Thr Ala Gly Ala
    8360            8365            8370

Thr Cys Thr Thr Ala Gly Cys Cys Ala Cys Thr Thr Thr Thr Thr
    8375            8380            8385

Ala Ala Ala Ala Gly Ala Ala Ala Ala Gly Gly Gly Gly Gly Gly
    8390            8395            8400

Ala Cys Thr Gly Gly Ala Ala Gly Gly Gly Cys Thr Ala Ala Thr
    8405            8410            8415

Thr Cys Ala Cys Thr Cys Cys Cys Ala Ala Cys Gly Ala Ala Gly
    8420            8425            8430

Ala Cys Ala Ala Gly Ala Thr Cys Thr Gly Cys Thr Thr Thr Thr
    8435            8440            8445

Thr Gly Cys Thr Thr Gly Thr Ala Cys Thr Gly Gly Gly Thr Cys
    8450            8455            8460

Thr Cys Thr Cys Thr Gly Gly Thr Thr Ala Gly Ala Cys Cys Ala
    8465            8470            8475

Gly Ala Thr Cys Thr Gly Ala Gly Cys Cys Thr Gly Gly Gly Ala
    8480            8485            8490

Gly Cys Thr Cys Thr Cys Thr Gly Gly Cys Thr Ala Ala Cys Thr
    8495            8500            8505

Ala Gly Gly Gly Ala Ala Cys Cys Cys Ala Cys Thr Gly Cys Thr
    8510            8515            8520

Thr Ala Ala Gly Cys Cys Thr Cys Ala Ala Thr Ala Ala Ala Gly
```

```
                    8525                    8530                    8535
Cys Thr Thr Gly Cys Cys Thr Gly Ala Gly Thr Gly Cys Thr
    8540                    8545                    8550
Thr Cys Ala Ala Gly Thr Ala Gly Thr Gly Thr Gly Thr Gly Cys
    8555                    8560                    8565
Cys Cys Gly Thr Cys Thr Gly Thr Thr Gly Thr Gly Thr Gly Ala
    8570                    8575                    8580
Cys Thr Cys Thr Gly Gly Thr Ala Ala Cys Thr Ala Gly Ala Gly
    8585                    8590                    8595
Ala Thr Cys Cys Cys Thr Cys Ala Gly Ala Cys Cys Cys Thr Thr
    8600                    8605                    8610
Thr Thr Ala Gly Thr Cys Ala Gly Thr Gly Thr Gly Gly Ala Ala
    8615                    8620                    8625
Ala Ala Thr Cys Thr Cys Thr Ala Gly Cys Ala Gly Thr Ala Gly
    8630                    8635                    8640
Thr Ala Gly Thr Thr Cys Ala Thr Gly Thr Cys Ala Thr Cys Thr
    8645                    8650                    8655
Thr Ala Thr Thr Ala Thr Thr Cys Ala Gly Thr Ala Thr Thr Thr
    8660                    8665                    8670
Ala Thr Ala Ala Cys Thr Thr Gly Cys Ala Ala Ala Gly Ala Ala
    8675                    8680                    8685
Ala Thr Gly Ala Ala Thr Ala Thr Cys Ala Gly Ala Gly Ala Gly
    8690                    8695                    8700
Thr Gly Ala Gly Ala Gly Gly Ala Ala Cys Thr Thr Gly Thr Thr
    8705                    8710                    8715
Thr Ala Thr Thr Gly Cys Ala Gly Cys Thr Thr Ala Thr Ala Ala
    8720                    8725                    8730
Thr Gly Gly Thr Thr Ala Cys Ala Ala Ala Thr Ala Ala Ala Gly
    8735                    8740                    8745
Cys Ala Ala Thr Ala Gly Cys Ala Thr Cys Ala Cys Ala Ala Ala
    8750                    8755                    8760
Thr Thr Thr Cys Ala Cys Ala Ala Ala Thr Ala Ala Ala Gly Cys
    8765                    8770                    8775
Ala Thr Thr Thr Thr Thr Thr Thr Cys Ala Cys Thr Gly Cys Ala
    8780                    8785                    8790
Thr Thr Cys Thr Ala Gly Thr Thr Gly Thr Gly Gly Thr Thr Thr
    8795                    8800                    8805
Gly Thr Cys Cys Ala Ala Ala Cys Thr Cys Ala Thr Cys Ala Ala
    8810                    8815                    8820
Thr Gly Thr Ala Thr Cys Thr Thr Ala Thr Cys Ala Thr Gly Thr
    8825                    8830                    8835
Cys Thr Gly Gly Cys Thr Cys Thr Ala Gly Cys Thr Ala Thr Cys
    8840                    8845                    8850
Cys Cys Gly Cys Cys Cys Thr Ala Ala Cys Thr Cys Cys Gly
    8855                    8860                    8865
Cys Cys Cys Ala Gly Thr Thr Cys Cys Gly Cys Cys Cys Ala Thr
    8870                    8875                    8880
Thr Cys Thr Cys Cys Gly Cys Cys Cys Cys Ala Thr Gly Gly Cys
    8885                    8890                    8895
Thr Gly Ala Cys Thr Ala Ala Thr Thr Thr Thr Thr Thr Thr
    8900                    8905                    8910
Ala Thr Thr Thr Ala Thr Gly Cys Ala Gly Ala Gly Gly Cys Cys
    8915                    8920                    8925
```

```
Gly Ala Gly Gly Cys Cys Gly Cys Cys Thr Cys Gly Gly Cys Cys
    8930            8935                8940

Thr Cys Thr Gly Ala Gly Cys Thr Ala Thr Thr Cys Cys Ala Gly
    8945            8950                8955

Ala Ala Gly Thr Ala Gly Thr Gly Ala Gly Gly Ala Gly Gly Cys
    8960            8965                8970

Thr Thr Thr Thr Thr Thr Gly Gly Ala Gly Gly Cys Cys Thr Ala
    8975            8980                8985

Gly Cys Thr Ala Gly Gly Gly Ala Cys Gly Thr Ala Cys Cys Cys
    8990            8995                9000

Ala Ala Thr Thr Cys Gly Cys Cys Cys Thr Ala Thr Ala Gly Thr
    9005            9010                9015

Gly Ala Gly Thr Cys Gly Thr Ala Thr Thr Ala Cys Gly Cys Gly
    9020            9025                9030

Cys Gly Cys Thr Cys Ala Cys Thr Gly Gly Cys Cys Gly Thr Cys
    9035            9040                9045

Gly Thr Thr Thr Thr Ala Cys Ala Ala Cys Gly Thr Cys Gly Thr
    9050            9055                9060

Gly Ala Cys Thr Gly Gly Gly Ala Ala Ala Ala Cys Cys Cys Thr
    9065            9070                9075

Gly Gly Cys Gly Thr Thr Ala Cys Cys Cys Ala Ala Cys Thr Thr
    9080            9085                9090

Ala Ala Thr Cys Gly Cys Cys Thr Thr Gly Cys Ala Gly Cys Ala
    9095            9100                9105

Cys Ala Thr Cys Cys Cys Cys Cys Thr Thr Thr Cys Gly Cys Cys
    9110            9115                9120

Ala Gly Cys Thr Gly Gly Cys Gly Thr Ala Ala Thr Ala Gly Cys
    9125            9130                9135

Gly Ala Ala Gly Ala Gly Gly Cys Cys Cys Gly Cys Ala Cys Cys
    9140            9145                9150

Gly Ala Thr Cys Gly Cys Cys Cys Thr Thr Cys Cys Cys Ala Ala
    9155            9160                9165

Cys Ala Gly Thr Thr Gly Cys Gly Cys Ala Gly Cys Cys Thr Gly
    9170            9175                9180

Ala Ala Thr Gly Gly Cys Gly Ala Ala Thr Gly Gly Gly Ala Cys
    9185            9190                9195

Gly Cys Gly Cys Cys Cys Thr Gly Thr Ala Gly Cys Gly Gly Cys
    9200            9205                9210

Gly Cys Ala Thr Thr Ala Ala Gly Cys Gly Cys Gly Gly Cys Gly
    9215            9220                9225

Gly Gly Thr Gly Thr Gly Gly Thr Gly Gly Thr Thr Ala Cys Gly
    9230            9235                9240

Cys Gly Cys Ala Gly Cys Gly Thr Gly Ala Cys Cys Gly Cys Thr
    9245            9250                9255

Ala Cys Ala Cys Thr Thr Gly Cys Cys Ala Gly Cys Gly Cys Cys
    9260            9265                9270

Cys Thr Ala Gly Cys Gly Cys Cys Cys Gly Cys Thr Cys Cys Thr
    9275            9280                9285

Thr Thr Cys Gly Cys Thr Thr Thr Cys Thr Thr Cys Cys Cys Thr
    9290            9295                9300

Thr Cys Cys Thr Thr Thr Cys Thr Cys Gly Cys Cys Ala Cys Gly
    9305            9310                9315
```

-continued

```
Thr Thr  Cys Gly Cys Cys Gly  Gly Cys Thr Thr Thr  Cys Cys Cys
    9320                 9325                 9330

Cys Gly  Thr Cys Ala Ala Gly  Cys Thr Cys Thr Ala  Ala Ala Thr
    9335                 9340                 9345

Cys Gly  Gly Gly Gly Gly Cys  Thr Cys Cys Cys Thr  Thr Thr Ala
    9350                 9355                 9360

Gly Gly  Gly Thr Thr Cys Cys  Gly Ala Thr Thr Thr  Ala Gly Thr
    9365                 9370                 9375

Gly Cys  Thr Thr Thr Ala Cys  Gly Gly Cys Ala Cys  Cys Thr Cys
    9380                 9385                 9390

Gly Ala  Cys Cys Cys Cys Ala  Ala Ala Ala Ala Ala  Cys Thr Thr
    9395                 9400                 9405

Gly Ala  Thr Thr Ala Gly Gly  Gly Thr Gly Ala Thr  Gly Gly Thr
    9410                 9415                 9420

Thr Cys  Ala Cys Gly Thr Ala  Gly Thr Gly Gly Gly  Cys Cys Ala
    9425                 9430                 9435

Thr Cys  Gly Cys Cys Cys Thr  Gly Ala Thr Ala Gly  Ala Cys Gly
    9440                 9445                 9450

Gly Thr  Thr Thr Thr Thr Cys  Gly Cys Cys Cys Thr  Thr Thr Gly
    9455                 9460                 9465

Ala Cys  Gly Thr Thr Gly Gly  Ala Gly Thr Cys Cys  Ala Cys Gly
    9470                 9475                 9480

Thr Thr  Cys Thr Thr Thr Ala  Ala Thr Ala Gly Thr  Gly Gly Ala
    9485                 9490                 9495

Cys Thr  Cys Thr Thr Gly Thr  Thr Cys Cys Ala Ala  Ala Cys Thr
    9500                 9505                 9510

Gly Gly  Ala Ala Cys Ala Ala  Cys Ala Cys Thr Cys  Ala Ala Cys
    9515                 9520                 9525

Cys Cys  Thr Ala Thr Cys Thr  Cys Gly Gly Thr Cys  Thr Ala Thr
    9530                 9535                 9540

Thr Cys  Thr Thr Thr Thr Gly  Ala Thr Thr Thr Ala  Thr Ala Ala
    9545                 9550                 9555

Gly Gly  Gly Ala Thr Thr Thr  Thr Gly Cys Cys Gly  Ala Thr Thr
    9560                 9565                 9570

Thr Cys  Gly Gly Cys Cys Thr  Ala Thr Thr Gly Gly  Thr Thr Ala
    9575                 9580                 9585

Ala Ala  Ala Ala Ala Thr Gly  Ala Gly Cys Thr Gly  Ala Thr Thr
    9590                 9595                 9600

Thr Ala  Ala Cys Ala Ala Ala  Ala Ala Thr Thr Thr  Ala Ala Cys
    9605                 9610                 9615

Gly Cys  Gly Ala Ala Thr Thr  Thr Thr Ala Ala Cys  Ala Ala Ala
    9620                 9625                 9630

Ala Thr  Ala Thr Thr Ala Ala  Cys Gly Cys Thr Thr  Ala Cys Ala
    9635                 9640                 9645

Ala Thr  Thr Thr Ala Gly Gly  Thr Gly Gly Cys Ala  Cys Thr Thr
    9650                 9655                 9660

Thr Thr  Cys Gly Gly Gly Gly  Ala Ala Ala Thr Gly  Thr Gly Cys
    9665                 9670                 9675

Gly Cys  Gly Gly Ala Ala Cys  Cys Cys Cys Thr Ala  Thr Thr Thr
    9680                 9685                 9690

Gly Thr  Thr Thr Ala Thr Thr  Thr Thr Thr Cys Thr  Ala Ala Ala
    9695                 9700                 9705

Thr Ala  Cys Ala Thr Thr Cys  Ala Ala Ala Thr Ala  Thr Gly Thr
```

```
                    9710                9715                9720
Ala Thr  Cys Cys Gly Cys Thr  Cys Ala Thr Gly Ala  Gly Ala Cys
        9725                9730                9735
Ala Ala  Thr Ala Ala Cys Cys  Cys Thr Gly Ala Thr  Ala Ala Ala
        9740                9745                9750
Thr Gly  Cys Thr Thr Cys Ala  Ala Thr Ala Ala Thr  Ala Thr Thr
        9755                9760                9765
Gly Ala  Ala Ala Ala Ala Gly  Gly Ala Ala Gly Ala  Gly Thr Ala
        9770                9775                9780
Thr Gly  Ala Gly Thr Ala Thr  Thr Cys Ala Ala Cys  Ala Thr Thr
        9785                9790                9795
Thr Cys  Cys Gly Thr Gly Thr  Cys Gly Cys Cys Cys  Thr Thr Ala
        9800                9805                9810
Thr Thr  Cys Cys Cys Thr Thr  Thr Thr Thr Thr Gly  Cys Gly Gly
        9815                9820                9825
Cys Ala  Thr Thr Thr Thr Gly  Cys Cys Thr Thr Cys  Cys Thr Gly
        9830                9835                9840
Thr Thr  Thr Thr Thr Gly Cys  Thr Cys Ala Cys Cys  Cys Ala Gly
        9845                9850                9855
Ala Ala  Ala Cys Gly Cys Thr  Gly Gly Thr Gly Ala  Ala Ala Gly
        9860                9865                9870
Thr Ala  Ala Ala Ala Gly Ala  Thr Gly Cys Thr Gly  Ala Ala Gly
        9875                9880                9885
Ala Thr  Cys Ala Gly Thr Thr  Gly Gly
        9890                9895

<210> SEQ ID NO 2
<211> LENGTH: 11758
<212> TYPE: PRT
<213> ORGANISM: Artificial Sequence
<220> FEATURE:
<223> OTHER INFORMATION: pTRPE_GPaspg_CAR

<400> SEQUENCE: 2

Gly Thr Gly Cys Ala Cys Gly Ala Gly Thr Gly Gly Gly Thr Thr Ala
1               5                   10                  15

Cys Ala Thr Cys Gly Ala Ala Cys Thr Gly Gly Ala Thr Cys Thr Cys
                20                  25                  30

Ala Ala Cys Ala Gly Cys Gly Gly Thr Ala Ala Gly Ala Thr Cys Cys
        35                  40                  45

Thr Thr Gly Ala Gly Ala Gly Thr Thr Thr Thr Cys Gly Cys Cys Cys
50                  55                  60

Cys Gly Ala Ala Gly Ala Ala Cys Gly Thr Thr Thr Thr Cys Cys Ala
65                  70                  75                  80

Ala Thr Gly Ala Thr Gly Ala Gly Cys Ala Cys Thr Thr Thr Thr Ala
                85                  90                  95

Ala Ala Gly Thr Thr Cys Thr Gly Cys Thr Ala Thr Gly Thr Gly Gly
            100                 105                 110

Cys Gly Cys Gly Gly Thr Ala Thr Thr Ala Thr Cys Cys Cys Gly Thr
        115                 120                 125

Ala Thr Thr Gly Ala Cys Gly Cys Cys Gly Gly Gly Cys Ala Ala Gly
        130                 135                 140

Ala Gly Cys Ala Ala Cys Thr Cys Gly Gly Thr Cys Gly Cys Cys Gly
145                 150                 155                 160

Cys Ala Thr Ala Cys Ala Cys Thr Ala Thr Thr Cys Thr Cys Ala Gly
```

-continued

```
                165                 170                 175
Ala Ala Thr Gly Ala Cys Thr Thr Gly Gly Thr Thr Gly Ala Gly Thr
            180                 185                 190

Ala Cys Thr Cys Ala Cys Cys Ala Gly Thr Cys Ala Cys Ala Gly Ala
        195                 200                 205

Ala Ala Ala Gly Cys Ala Thr Cys Thr Thr Ala Cys Gly Gly Ala Thr
    210                 215                 220

Gly Gly Cys Ala Thr Gly Ala Cys Ala Gly Thr Ala Ala Gly Ala Gly
225                 230                 235                 240
Ala Ala Thr Thr Ala Thr Gly Cys Ala Gly Thr Gly Cys Thr Gly Cys
                245                 250                 255
Cys Ala Thr Ala Ala Cys Cys Ala Thr Gly Ala Gly Thr Gly Ala Thr
            260                 265                 270

Ala Ala Cys Ala Cys Thr Gly Cys Gly Gly Cys Cys Ala Ala Cys Thr
        275                 280                 285

Thr Ala Cys Thr Thr Cys Thr Gly Ala Cys Ala Ala Cys Gly Ala Thr
    290                 295                 300

Cys Gly Gly Ala Gly Gly Ala Cys Cys Gly Ala Ala Gly Gly Ala Gly
305                 310                 315                 320
Cys Thr Ala Ala Cys Cys Gly Cys Thr Thr Thr Thr Thr Thr Gly Cys
                325                 330                 335
Ala Cys Ala Ala Cys Ala Thr Gly Gly Gly Gly Gly Ala Thr Cys Ala
            340                 345                 350

Thr Gly Thr Ala Ala Cys Thr Cys Gly Cys Cys Thr Thr Gly Ala Thr
        355                 360                 365

Cys Gly Thr Thr Gly Gly Gly Ala Ala Cys Cys Gly Gly Ala Gly Cys
    370                 375                 380

Thr Gly Ala Ala Thr Gly Ala Ala Gly Cys Cys Ala Thr Ala Cys Cys
385                 390                 395                 400

Ala Ala Ala Cys Gly Ala Cys Gly Ala Gly Cys Gly Thr Gly Ala Cys
                405                 410                 415

Ala Cys Cys Ala Cys Gly Ala Thr Gly Cys Cys Thr Gly Thr Ala Gly
            420                 425                 430

Cys Ala Ala Thr Gly Gly Cys Ala Ala Cys Ala Ala Cys Gly Thr Thr
        435                 440                 445

Gly Cys Gly Cys Ala Ala Ala Cys Thr Ala Thr Thr Ala Ala Cys Thr
    450                 455                 460

Gly Gly Cys Gly Ala Ala Cys Thr Ala Cys Thr Thr Ala Cys Thr Cys
465                 470                 475                 480

Thr Ala Gly Cys Thr Thr Cys Cys Cys Gly Gly Cys Ala Ala Cys Ala
                485                 490                 495

Ala Thr Thr Ala Ala Thr Ala Gly Ala Cys Thr Gly Gly Ala Thr Gly
            500                 505                 510

Gly Ala Gly Gly Cys Gly Gly Ala Thr Ala Ala Ala Gly Thr Thr Gly
        515                 520                 525

Cys Ala Gly Gly Ala Cys Cys Ala Cys Thr Thr Cys Thr Gly Cys Gly
    530                 535                 540

Cys Thr Cys Gly Gly Cys Cys Cys Thr Thr Cys Cys Gly Gly Cys Thr
545                 550                 555                 560

Gly Gly Cys Thr Gly Gly Thr Thr Thr Ala Thr Thr Gly Cys Thr Gly
                565                 570                 575

Ala Thr Ala Ala Ala Thr Cys Thr Gly Gly Ala Gly Cys Cys Gly Gly
            580                 585                 590
```

```
Thr Gly Ala Gly Cys Gly Thr Gly Gly Thr Cys Thr Gly Cys
        595                 600                 605
Gly Gly Thr Ala Thr Cys Ala Thr Thr Gly Cys Ala Gly Cys Ala Cys
610                 615                 620
Thr Gly Gly Gly Cys Cys Ala Gly Ala Thr Gly Gly Thr Ala Ala
625                 630                 635                 640
Gly Cys Cys Thr Cys Cys Gly Thr Ala Thr Cys Gly Thr Ala
                645                 650                 655
Gly Thr Thr Ala Thr Cys Thr Ala Cys Ala Cys Gly Ala Cys Gly Gly
            660                 665                 670
Gly Gly Ala Gly Thr Cys Ala Gly Gly Cys Ala Ala Cys Thr Ala Thr
                675                 680                 685
Gly Gly Ala Thr Gly Ala Ala Cys Gly Ala Ala Thr Ala Gly Ala
            690                 695                 700
Cys Ala Gly Ala Thr Cys Gly Cys Thr Gly Ala Gly Ala Thr Ala Gly
705                 710                 715                 720
Gly Thr Gly Cys Cys Thr Cys Ala Cys Thr Gly Ala Thr Thr Ala Ala
                725                 730                 735
Gly Cys Ala Thr Thr Gly Gly Thr Ala Ala Cys Thr Gly Thr Cys Ala
            740                 745                 750
Gly Ala Cys Cys Ala Ala Gly Thr Thr Thr Ala Cys Thr Cys Ala Thr
            755                 760                 765
Ala Thr Ala Thr Ala Cys Thr Thr Thr Ala Gly Ala Thr Thr Gly Ala
        770                 775                 780
Thr Thr Thr Ala Ala Ala Ala Cys Thr Thr Cys Ala Thr Thr Thr Thr
785                 790                 795                 800
Thr Ala Ala Thr Thr Thr Ala Ala Ala Ala Gly Gly Ala Thr Cys Thr
                805                 810                 815
Ala Gly Gly Thr Gly Ala Ala Gly Ala Thr Cys Cys Thr Thr Thr Thr
                820                 825                 830
Thr Gly Ala Thr Ala Ala Thr Cys Thr Cys Ala Thr Gly Ala Cys Cys
        835                 840                 845
Ala Ala Ala Ala Thr Cys Cys Cys Thr Thr Ala Ala Cys Gly Thr Gly
850                 855                 860
Ala Gly Thr Thr Thr Thr Cys Gly Thr Thr Cys Cys Ala Cys Thr Gly
865                 870                 875                 880
Ala Gly Cys Gly Thr Cys Ala Gly Ala Cys Cys Cys Cys Gly Thr Ala
                885                 890                 895
Gly Ala Ala Ala Ala Gly Ala Thr Cys Ala Ala Ala Gly Gly Ala Thr
                900                 905                 910
Cys Thr Thr Cys Thr Thr Gly Ala Gly Ala Thr Cys Cys Thr Thr Thr
            915                 920                 925
Thr Thr Thr Thr Cys Thr Gly Cys Gly Cys Gly Thr Ala Ala Thr Cys
        930                 935                 940
Thr Gly Cys Thr Gly Cys Thr Thr Gly Cys Ala Ala Ala Cys Ala Ala
945                 950                 955                 960
Ala Ala Ala Ala Ala Cys Cys Ala Cys Cys Gly Cys Thr Ala Cys Cys
            965                 970                 975
Ala Gly Cys Gly Gly Thr Gly Gly Thr Thr Thr Gly Thr Thr Thr Gly
            980                 985                 990
Cys Cys Gly Gly Ala Thr Cys Ala  Ala Gly Ala Gly Cys  Thr Ala Cys
            995                 1000                 1005
```

-continued

```
Cys Ala Ala Cys Thr Cys Thr Thr Thr Thr Cys Cys Gly Ala
    1010            1015               1020

Ala Gly Gly Thr Ala Ala Cys Thr Gly Gly Cys Thr Thr Cys Ala
    1025            1030               1035

Gly Cys Ala Gly Ala Gly Cys Gly Cys Ala Gly Ala Thr Ala Cys
    1040            1045               1050

Cys Ala Ala Ala Thr Ala Cys Thr Gly Thr Thr Cys Thr Thr Cys
    1055            1060               1065

Thr Ala Gly Thr Gly Thr Ala Gly Cys Cys Gly Thr Ala Gly Thr
    1070            1075               1080

Thr Ala Gly Gly Cys Cys Ala Cys Cys Ala Cys Thr Thr Cys Ala
    1085            1090               1095

Ala Gly Ala Ala Cys Thr Cys Thr Gly Thr Ala Gly Cys Ala Cys
    1100            1105               1110

Cys Gly Cys Cys Thr Ala Cys Ala Thr Ala Cys Cys Thr Cys Gly
    1115            1120               1125

Cys Thr Cys Thr Gly Cys Thr Ala Ala Thr Cys Cys Thr Gly Thr
    1130            1135               1140

Thr Ala Cys Cys Ala Gly Thr Gly Gly Cys Thr Gly Cys Thr Gly
    1145            1150               1155

Cys Cys Ala Gly Thr Gly Gly Cys Gly Ala Thr Ala Ala Gly Thr
    1160            1165               1170

Cys Gly Thr Gly Thr Cys Thr Thr Ala Cys Cys Gly Gly Gly Thr
    1175            1180               1185

Thr Gly Gly Ala Cys Thr Cys Ala Ala Gly Ala Cys Gly Ala Thr
    1190            1195               1200

Ala Gly Thr Thr Ala Cys Cys Gly Gly Ala Thr Ala Ala Gly Gly
    1205            1210               1215

Cys Gly Cys Ala Gly Cys Gly Gly Thr Cys Gly Gly Gly Cys Thr
    1220            1225               1230

Gly Ala Ala Cys Gly Gly Gly Gly Gly Thr Thr Cys Gly Thr
    1235            1240               1245

Gly Cys Ala Cys Ala Cys Ala Gly Cys Cys Cys Ala Gly Cys Thr
    1250            1255               1260

Thr Gly Gly Ala Gly Cys Gly Ala Ala Cys Gly Ala Cys Cys Thr
    1265            1270               1275

Ala Cys Ala Cys Cys Gly Ala Ala Cys Thr Gly Ala Gly Ala Thr
    1280            1285               1290

Ala Cys Cys Thr Ala Cys Ala Gly Cys Gly Thr Gly Ala Gly Cys
    1295            1300               1305

Thr Ala Thr Gly Ala Gly Ala Ala Ala Gly Cys Gly Cys Cys Ala
    1310            1315               1320

Cys Gly Cys Thr Thr Cys Cys Gly Ala Ala Gly Gly Gly Ala
    1325            1330               1335

Gly Ala Ala Ala Gly Gly Cys Gly Gly Ala Cys Ala Gly Gly Thr
    1340            1345               1350

Ala Thr Cys Cys Gly Gly Thr Ala Ala Gly Cys Gly Gly Cys Ala
    1355            1360               1365

Gly Gly Gly Thr Cys Gly Gly Ala Ala Cys Ala Gly Gly Ala Gly
    1370            1375               1380

Ala Gly Cys Gly Cys Ala Cys Gly Ala Gly Gly Gly Ala Gly Cys
    1385            1390               1395

Thr Thr Cys Cys Ala Gly Gly Gly Gly Gly Ala Ala Ala Cys Gly
```

-continued

```
    1400                1405                1410

Cys Cys  Thr Gly Gly Thr Ala  Thr Cys Thr Thr Thr  Ala Thr Ala
    1415                1420                1425

Gly Thr  Cys Cys Thr Gly Thr  Cys Gly Gly Gly Thr  Thr Thr Cys
    1430                1435                1440

Gly Cys  Cys Ala Cys Cys Thr  Cys Thr Gly Ala Cys  Thr Thr Gly
    1445                1450                1455

Ala Gly  Cys Gly Thr Cys Gly  Ala Thr Thr Thr Thr  Thr Gly Thr
    1460                1465                1470

Gly Ala  Thr Gly Cys Thr Cys  Gly Thr Cys Ala Gly  Gly Gly Gly
    1475                1480                1485

Gly Gly  Cys Gly Gly Ala Gly  Cys Cys Thr Ala Thr  Gly Gly Ala
    1490                1495                1500

Ala Ala  Ala Ala Cys Gly Cys  Cys Ala Gly Cys Ala  Ala Cys Gly
    1505                1510                1515

Cys Gly  Gly Cys Cys Thr Thr  Thr Thr Thr Ala Cys  Gly Gly Thr
    1520                1525                1530

Thr Cys  Cys Thr Gly Gly Cys  Cys Thr Thr Thr Thr  Gly Cys Thr
    1535                1540                1545

Gly Gly  Cys Cys Thr Thr Thr  Thr Gly Cys Thr Cys  Ala Cys Ala
    1550                1555                1560

Thr Gly  Thr Thr Cys Thr Thr  Thr Cys Cys Thr Gly  Cys Gly Thr
    1565                1570                1575

Thr Ala  Thr Cys Cys Cys Cys  Thr Gly Ala Thr Thr  Cys Thr Gly
    1580                1585                1590

Thr Gly  Gly Ala Thr Ala Ala  Cys Cys Gly Thr Ala  Thr Thr Ala
    1595                1600                1605

Cys Cys  Gly Cys Cys Thr Thr  Thr Gly Ala Gly Thr  Gly Ala Gly
    1610                1615                1620

Cys Thr  Gly Ala Thr Ala Cys  Cys Gly Cys Thr Cys  Gly Cys Cys
    1625                1630                1635

Gly Cys  Ala Gly Cys Cys Gly  Ala Ala Cys Gly Ala  Cys Cys Gly
    1640                1645                1650

Ala Gly  Cys Gly Cys Ala Gly  Cys Gly Ala Gly Thr  Cys Ala Gly
    1655                1660                1665

Thr Gly  Ala Gly Cys Gly Ala  Gly Gly Ala Ala Gly  Cys Gly Gly
    1670                1675                1680

Ala Ala  Gly Ala Gly Cys Gly  Cys Cys Cys Ala Ala  Thr Ala Cys
    1685                1690                1695

Gly Cys  Ala Ala Ala Cys Cys  Gly Cys Cys Thr Cys  Thr Cys Cys
    1700                1705                1710

Cys Cys  Gly Cys Gly Cys Gly  Thr Thr Gly Gly Cys  Cys Gly Ala
    1715                1720                1725

Thr Thr  Cys Ala Thr Thr Ala  Ala Thr Gly Cys Ala  Gly Cys Thr
    1730                1735                1740

Gly Gly  Cys Ala Cys Gly Ala  Cys Ala Gly Gly Thr  Thr Thr Cys
    1745                1750                1755

Cys Cys  Gly Ala Cys Thr Gly  Gly Ala Ala Ala Gly  Cys Gly Gly
    1760                1765                1770

Gly Cys  Ala Gly Thr Gly Ala  Gly Cys Gly Cys Ala  Ala Cys Gly
    1775                1780                1785

Cys Ala  Ala Thr Thr Ala Ala  Thr Gly Thr Gly Ala  Gly Thr Thr
    1790                1795                1800
```

-continued

```
Ala Gly Cys Thr Cys Ala Cys Thr Cys Ala Thr Thr Ala Gly Gly
    1805                1810                1815
Cys Ala Cys Cys Cys Cys Ala Gly Gly Cys Thr Thr Thr Ala Cys
    1820                1825                1830
Ala Cys Thr Thr Thr Ala Thr Gly Cys Thr Thr Cys Cys Gly Gly
    1835                1840                1845
Cys Thr Cys Gly Thr Ala Thr Gly Thr Thr Gly Thr Gly Thr Gly
    1850                1855                1860
Gly Ala Ala Thr Thr Gly Thr Gly Ala Gly Cys Gly Gly Ala Thr
    1865                1870                1875
Ala Ala Cys Ala Ala Thr Thr Thr Cys Ala Cys Ala Cys Ala Gly
    1880                1885                1890
Gly Ala Ala Ala Cys Ala Gly Cys Thr Ala Thr Gly Ala Cys Cys
    1895                1900                1905
Ala Thr Gly Ala Thr Thr Ala Cys Gly Cys Cys Ala Ala Gly Cys
    1910                1915                1920
Gly Cys Gly Cys Ala Ala Thr Thr Ala Ala Cys Cys Cys Thr Cys
    1925                1930                1935
Ala Cys Thr Ala Ala Ala Gly Gly Gly Ala Ala Cys Ala Ala Ala
    1940                1945                1950
Ala Gly Cys Thr Gly Gly Ala Gly Cys Thr Gly Cys Ala Ala Gly
    1955                1960                1965
Cys Thr Thr Ala Ala Thr Gly Thr Ala Gly Thr Cys Thr Thr Ala
    1970                1975                1980
Thr Gly Cys Ala Ala Thr Ala Cys Thr Cys Thr Thr Gly Thr Ala
    1985                1990                1995
Gly Thr Cys Thr Thr Gly Cys Ala Ala Cys Ala Thr Gly Gly Thr
    2000                2005                2010
Ala Ala Cys Gly Ala Thr Gly Ala Gly Thr Thr Ala Gly Cys Ala
    2015                2020                2025
Ala Cys Ala Thr Gly Cys Cys Thr Thr Ala Cys Ala Ala Gly Gly
    2030                2035                2040
Ala Gly Ala Gly Ala Ala Ala Ala Ala Gly Cys Ala Cys Cys Gly
    2045                2050                2055
Thr Gly Cys Ala Thr Gly Cys Cys Gly Ala Thr Thr Gly Gly Thr
    2060                2065                2070
Gly Gly Ala Ala Gly Thr Ala Ala Gly Gly Thr Gly Gly Thr Ala
    2075                2080                2085
Cys Gly Ala Thr Cys Gly Thr Gly Cys Cys Thr Thr Ala Thr Thr
    2090                2095                2100
Ala Gly Gly Ala Ala Gly Gly Cys Ala Ala Cys Ala Gly Ala Cys
    2105                2110                2115
Gly Gly Gly Thr Cys Thr Gly Ala Cys Ala Thr Gly Gly Ala Thr
    2120                2125                2130
Thr Gly Gly Ala Cys Gly Ala Ala Cys Cys Ala Cys Thr Gly Ala
    2135                2140                2145
Ala Thr Thr Gly Cys Cys Gly Cys Ala Thr Thr Gly Cys Ala Gly
    2150                2155                2160
Ala Gly Ala Thr Ala Thr Thr Gly Thr Ala Thr Thr Thr Ala Ala
    2165                2170                2175
Gly Thr Gly Cys Cys Thr Ala Gly Cys Thr Cys Gly Ala Thr Ala
    2180                2185                2190
```

-continued

```
Cys Ala  Thr Ala Ala Ala  Cys Gly Gly Thr  Cys Thr Cys Thr
    2195              2200              2205

Cys Thr  Gly Gly Thr Thr  Ala Gly Ala Cys  Cys Ala Gly Ala Thr
    2210              2215              2220

Cys Thr  Gly Ala Gly Cys  Thr Gly Gly Ala  Gly Cys Thr
    2225              2230              2235

Cys Thr  Cys Thr Gly Gly  Cys Thr Ala Ala  Cys Thr Ala Gly Gly
    2240              2245              2250

Gly Ala  Ala Cys Cys Ala  Cys Thr Gly Cys  Thr Thr Ala Ala
    2255              2260              2265

Gly Cys  Cys Thr Cys Ala  Ala Thr Ala Ala  Ala Gly Cys Thr Thr
    2270              2275              2280

Gly Cys  Cys Thr Thr Gly  Ala Gly Thr Gly  Cys Thr Thr Cys Ala
    2285              2290              2295

Ala Gly  Thr Ala Gly Thr  Gly Thr Gly Thr  Gly Cys Cys Gly
    2300              2305              2310

Thr Cys  Thr Gly Thr Thr  Gly Thr Gly Thr  Gly Ala Cys Thr Cys
    2315              2320              2325

Thr Gly  Gly Thr Ala Ala  Cys Thr Ala Gly  Ala Gly Ala Thr Cys
    2330              2335              2340

Cys Cys  Thr Cys Ala Gly  Ala Cys Cys Cys  Thr Thr Thr Thr Ala
    2345              2350              2355

Gly Thr  Cys Ala Gly Thr  Gly Thr Gly Gly  Ala Ala Ala Ala Thr
    2360              2365              2370

Cys Thr  Cys Thr Ala Gly  Cys Ala Gly Thr  Gly Gly Cys Gly Cys
    2375              2380              2385

Cys Cys  Gly Ala Ala Cys  Ala Gly Gly Gly  Ala Cys Thr Thr Gly
    2390              2395              2400

Ala Ala  Ala Gly Cys Gly  Ala Ala Ala Gly  Gly Gly Ala Ala Ala
    2405              2410              2415

Cys Cys  Ala Gly Ala Gly  Gly Ala Gly Cys  Thr Cys Thr Cys Thr
    2420              2425              2430

Cys Gly  Ala Cys Gly Cys  Ala Gly Gly Ala  Cys Thr Cys Gly Gly
    2435              2440              2445

Cys Thr  Thr Gly Cys Thr  Gly Ala Ala Gly  Cys Gly Cys Gly Cys
    2450              2455              2460

Ala Cys  Gly Gly Cys Ala  Ala Gly Ala Gly  Gly Cys Gly Ala Gly
    2465              2470              2475

Gly Gly  Gly Cys Gly Gly  Cys Gly Ala Cys  Thr Gly Gly Thr Gly
    2480              2485              2490

Ala Gly  Thr Ala Cys Gly  Cys Cys Ala Ala  Ala Ala Thr Thr
    2495              2500              2505

Thr Thr  Gly Ala Cys Thr  Ala Gly Cys Gly  Gly Ala Gly Gly Cys
    2510              2515              2520

Thr Ala  Gly Ala Ala Gly  Gly Ala Gly Ala  Gly Ala Gly Ala Thr
    2525              2530              2535

Gly Gly  Gly Thr Gly Cys  Gly Ala Gly Ala  Gly Cys Gly Thr Cys
    2540              2545              2550

Ala Gly  Thr Ala Thr Thr  Ala Ala Gly Cys  Gly Gly Gly Gly Gly
    2555              2560              2565

Ala Gly  Ala Ala Thr Thr  Ala Gly Ala Thr  Cys Gly Cys Gly Ala
    2570              2575              2580

Thr Gly  Gly Gly Ala Ala  Ala Ala Ala Ala  Thr Thr Cys Gly Gly
```

|  | 2585 |  |  | 2590 |  |  | 2595 |  |  |  |  |

| Thr | Thr | Ala | Ala | Gly | Gly | Cys | Cys | Ala | Gly | Gly | Gly | Gly | Ala |
|---|---|---|---|---|---|---|---|---|---|---|---|---|---|
|  | 2600 |  |  |  | 2605 |  |  |  |  | 2610 |  |  |  |

| Ala | Ala | Gly | Ala | Ala | Ala | Ala | Ala | Ala | Thr | Ala | Thr | Ala | Ala | Ala |
|---|---|---|---|---|---|---|---|---|---|---|---|---|---|---|
|  | 2615 |  |  |  | 2620 |  |  |  |  | 2625 |  |  |  |  |

| Thr | Thr | Ala | Ala | Ala | Ala | Cys | Ala | Thr | Ala | Thr | Ala | Gly | Thr | Ala |
|---|---|---|---|---|---|---|---|---|---|---|---|---|---|---|
|  | 2630 |  |  |  | 2635 |  |  |  |  | 2640 |  |  |  |  |

| Thr | Gly | Gly | Gly | Cys | Ala | Ala | Gly | Cys | Ala | Gly | Gly | Ala | Gly |
|---|---|---|---|---|---|---|---|---|---|---|---|---|---|
|  | 2645 |  |  |  | 2650 |  |  |  |  | 2655 |  |  |  |

| Cys | Thr | Ala | Gly | Ala | Ala | Cys | Gly | Ala | Thr | Thr | Cys | Gly | Cys | Ala |
|---|---|---|---|---|---|---|---|---|---|---|---|---|---|---|
|  | 2660 |  |  |  | 2665 |  |  |  |  | 2670 |  |  |  |  |

| Gly | Thr | Thr | Ala | Ala | Thr | Cys | Cys | Thr | Gly | Gly | Cys | Cys | Thr | Gly |
|---|---|---|---|---|---|---|---|---|---|---|---|---|---|---|
|  | 2675 |  |  |  | 2680 |  |  |  |  | 2685 |  |  |  |  |

| Thr | Thr | Ala | Gly | Ala | Ala | Ala | Cys | Ala | Thr | Cys | Ala | Gly | Ala | Ala |
|---|---|---|---|---|---|---|---|---|---|---|---|---|---|---|
|  | 2690 |  |  |  | 2695 |  |  |  |  | 2700 |  |  |  |  |

| Gly | Gly | Cys | Thr | Gly | Thr | Ala | Gly | Ala | Cys | Ala | Ala | Thr | Ala |
|---|---|---|---|---|---|---|---|---|---|---|---|---|---|
|  | 2705 |  |  |  | 2710 |  |  |  |  | 2715 |  |  |  |

| Cys | Thr | Gly | Gly | Gly | Ala | Cys | Ala | Gly | Cys | Thr | Ala | Cys | Ala | Ala |
|---|---|---|---|---|---|---|---|---|---|---|---|---|---|---|
|  | 2720 |  |  |  | 2725 |  |  |  |  | 2730 |  |  |  |  |

| Cys | Cys | Ala | Thr | Cys | Cys | Cys | Thr | Thr | Cys | Ala | Gly | Ala | Cys | Ala |
|---|---|---|---|---|---|---|---|---|---|---|---|---|---|---|
|  | 2735 |  |  |  | 2740 |  |  |  |  | 2745 |  |  |  |  |

| Gly | Gly | Ala | Thr | Cys | Ala | Gly | Ala | Ala | Gly | Ala | Ala | Cys | Thr | Thr |
|---|---|---|---|---|---|---|---|---|---|---|---|---|---|---|
|  | 2750 |  |  |  | 2755 |  |  |  |  | 2760 |  |  |  |  |

| Ala | Gly | Ala | Thr | Cys | Ala | Thr | Thr | Ala | Thr | Ala | Thr | Ala | Ala | Thr |
|---|---|---|---|---|---|---|---|---|---|---|---|---|---|---|
|  | 2765 |  |  |  | 2770 |  |  |  |  | 2775 |  |  |  |  |

| Ala | Cys | Ala | Gly | Thr | Ala | Gly | Cys | Ala | Ala | Cys | Cys | Cys | Thr | Cys |
|---|---|---|---|---|---|---|---|---|---|---|---|---|---|---|
|  | 2780 |  |  |  | 2785 |  |  |  |  | 2790 |  |  |  |  |

| Thr | Ala | Thr | Thr | Gly | Thr | Gly | Thr | Gly | Cys | Ala | Thr | Cys | Ala | Ala |
|---|---|---|---|---|---|---|---|---|---|---|---|---|---|---|
|  | 2795 |  |  |  | 2800 |  |  |  |  | 2805 |  |  |  |  |

| Ala | Gly | Gly | Ala | Thr | Ala | Gly | Ala | Gly | Ala | Thr | Ala | Ala | Ala | Ala |
|---|---|---|---|---|---|---|---|---|---|---|---|---|---|---|
|  | 2810 |  |  |  | 2815 |  |  |  |  | 2820 |  |  |  |  |

| Gly | Ala | Cys | Ala | Cys | Cys | Ala | Ala | Gly | Gly | Ala | Ala | Gly | Cys | Thr |
|---|---|---|---|---|---|---|---|---|---|---|---|---|---|---|
|  | 2825 |  |  |  | 2830 |  |  |  |  | 2835 |  |  |  |  |

| Thr | Thr | Ala | Gly | Ala | Cys | Ala | Ala | Gly | Ala | Thr | Ala | Gly | Ala | Gly |
|---|---|---|---|---|---|---|---|---|---|---|---|---|---|---|
|  | 2840 |  |  |  | 2845 |  |  |  |  | 2850 |  |  |  |  |

| Gly | Ala | Ala | Gly | Ala | Gly | Cys | Ala | Ala | Ala | Cys | Ala | Ala | Ala |
|---|---|---|---|---|---|---|---|---|---|---|---|---|---|
|  | 2855 |  |  |  | 2860 |  |  |  |  | 2865 |  |  |  |

| Ala | Gly | Thr | Ala | Ala | Gly | Ala | Cys | Cys | Ala | Cys | Cys | Gly | Cys | Ala |
|---|---|---|---|---|---|---|---|---|---|---|---|---|---|---|
|  | 2870 |  |  |  | 2875 |  |  |  |  | 2880 |  |  |  |  |

| Cys | Ala | Gly | Cys | Ala | Ala | Gly | Cys | Gly | Gly | Cys | Cys | Gly | Cys | Thr |
|---|---|---|---|---|---|---|---|---|---|---|---|---|---|---|
|  | 2885 |  |  |  | 2890 |  |  |  |  | 2895 |  |  |  |  |

| Gly | Ala | Thr | Cys | Thr | Thr | Cys | Ala | Gly | Ala | Cys | Cys | Thr | Gly | Gly |
|---|---|---|---|---|---|---|---|---|---|---|---|---|---|---|
|  | 2900 |  |  |  | 2905 |  |  |  |  | 2910 |  |  |  |  |

| Ala | Gly | Gly | Ala | Gly | Gly | Ala | Gly | Ala | Thr | Ala | Thr | Gly | Ala | Gly |
|---|---|---|---|---|---|---|---|---|---|---|---|---|---|---|
|  | 2915 |  |  |  | 2920 |  |  |  |  | 2925 |  |  |  |  |

| Gly | Gly | Ala | Cys | Ala | Ala | Thr | Thr | Gly | Gly | Ala | Gly | Ala | Ala | Gly |
|---|---|---|---|---|---|---|---|---|---|---|---|---|---|---|
|  | 2930 |  |  |  | 2935 |  |  |  |  | 2940 |  |  |  |  |

| Thr | Gly | Ala | Ala | Thr | Thr | Ala | Thr | Ala | Thr | Ala | Ala | Thr | Ala |
|---|---|---|---|---|---|---|---|---|---|---|---|---|---|
|  | 2945 |  |  |  | 2950 |  |  |  |  | 2955 |  |  |  |

| Thr | Ala | Ala | Ala | Gly | Thr | Ala | Gly | Thr | Ala | Ala | Ala | Ala | Thr |
|---|---|---|---|---|---|---|---|---|---|---|---|---|---|
|  | 2960 |  |  |  | 2965 |  |  |  |  | 2970 |  |  |  |

| Thr | Gly | Ala | Ala | Cys | Cys | Ala | Thr | Thr | Ala | Gly | Gly | Ala | Gly | Thr |
|---|---|---|---|---|---|---|---|---|---|---|---|---|---|---|
|  | 2975 |  |  |  | 2980 |  |  |  |  | 2985 |  |  |  |  |

```
Ala Gly Cys Ala Cys Cys Cys Ala Cys Ala Gly Gly Cys
2990                2995                3000

Ala Ala Ala Gly Ala Gly Ala Ala Gly Ala Gly Thr Gly Gly Thr
3005                3010                3015

Gly Cys Ala Gly Ala Gly Ala Gly Ala Ala Ala Ala Ala Gly
3020                3025                3030

Ala Gly Cys Ala Gly Thr Gly Gly Gly Ala Ala Thr Ala Gly Gly
3035                3040                3045

Ala Gly Cys Thr Thr Thr Gly Thr Thr Cys Cys Thr Thr Gly Gly
3050                3055                3060

Gly Thr Thr Cys Thr Thr Gly Gly Gly Ala Gly Cys Ala Gly Cys
3065                3070                3075

Ala Gly Gly Ala Ala Gly Cys Ala Cys Thr Ala Thr Gly Gly Gly
3080                3085                3090

Cys Gly Cys Ala Gly Cys Gly Thr Cys Ala Ala Thr Gly Ala Cys
3095                3100                3105

Gly Cys Thr Gly Ala Cys Gly Gly Thr Ala Cys Ala Gly Gly Cys
3110                3115                3120

Cys Ala Gly Ala Cys Ala Ala Thr Thr Ala Thr Thr Gly Thr Cys
3125                3130                3135

Thr Gly Gly Thr Ala Thr Ala Gly Thr Gly Cys Ala Gly Cys Ala
3140                3145                3150

Gly Cys Ala Gly Ala Ala Cys Ala Ala Thr Thr Thr Gly Cys Thr
3155                3160                3165

Gly Ala Gly Gly Gly Cys Thr Ala Thr Thr Gly Ala Gly Gly Cys
3170                3175                3180

Gly Cys Ala Ala Cys Ala Gly Cys Ala Thr Cys Thr Gly Thr Thr
3185                3190                3195

Gly Cys Ala Ala Cys Thr Cys Ala Cys Ala Gly Thr Cys Thr Gly
3200                3205                3210

Gly Gly Gly Cys Ala Thr Cys Ala Ala Gly Cys Ala Gly Cys Thr
3215                3220                3225

Cys Cys Ala Gly Gly Cys Ala Ala Gly Ala Ala Thr Cys Cys Thr
3230                3235                3240

Gly Gly Cys Thr Gly Thr Gly Gly Ala Ala Ala Gly Ala Thr Ala
3245                3250                3255

Cys Cys Thr Ala Ala Ala Gly Gly Ala Thr Cys Ala Ala Cys Ala
3260                3265                3270

Gly Cys Thr Cys Cys Thr Gly Gly Gly Ala Thr Thr Thr Thr Gly
3275                3280                3285

Gly Gly Gly Thr Thr Gly Cys Thr Cys Thr Gly Gly Ala Ala Ala
3290                3295                3300

Ala Cys Thr Cys Ala Thr Thr Thr Gly Cys Ala Cys Cys Ala Cys
3305                3310                3315

Thr Gly Cys Thr Gly Thr Gly Cys Cys Thr Thr Gly Gly Ala Ala
3320                3325                3330

Thr Gly Cys Thr Ala Gly Thr Gly Gly Ala Gly Thr Ala Ala
3335                3340                3345

Thr Ala Ala Ala Thr Cys Thr Cys Thr Gly Gly Ala Ala Cys Ala
3350                3355                3360

Gly Ala Thr Thr Thr Gly Gly Ala Ala Thr Cys Ala Cys Ala Cys
3365                3370                3375
```

|     |     |     |     |     |     |     |     |     |     |     |     |     |
|-----|-----|-----|-----|-----|-----|-----|-----|-----|-----|-----|-----|-----|
| Gly | Ala | Cys | Cys | Thr | Gly | Gly | Ala | Thr | Gly | Ala | Gly | Thr |
|     | 3380 |     |     |     | 3385 |     |     |     | 3390 |     |     |     |
| Gly | Gly | Ala | Cys | Ala | Gly | Ala | Gly | Ala | Ala | Ala | Thr | Thr | Ala | Ala |
|     | 3395 |     |     |     | 3400 |     |     |     | 3405 |     |     |     |
| Cys | Ala | Ala | Thr | Thr | Ala | Cys | Ala | Cys | Ala | Ala | Gly | Cys | Thr | Thr |
|     | 3410 |     |     |     | 3415 |     |     |     | 3420 |     |     |     |
| Ala | Ala | Thr | Ala | Cys | Ala | Cys | Thr | Cys | Cys | Thr | Thr | Ala | Ala | Thr |
|     | 3425 |     |     |     | 3430 |     |     |     | 3435 |     |     |     |
| Thr | Gly | Ala | Ala | Gly | Ala | Ala | Thr | Cys | Gly | Cys | Ala | Ala | Ala | Ala |
|     | 3440 |     |     |     | 3445 |     |     |     | 3450 |     |     |     |
| Cys | Cys | Ala | Gly | Cys | Ala | Ala | Gly | Ala | Ala | Ala | Gly | Ala | Ala |
|     | 3455 |     |     |     | 3460 |     |     |     | 3465 |     |     |     |
| Thr | Gly | Ala | Ala | Cys | Ala | Ala | Gly | Ala | Ala | Thr | Thr | Ala | Thr | Thr |
|     | 3470 |     |     |     | 3475 |     |     |     | 3480 |     |     |     |
| Gly | Gly | Ala | Ala | Thr | Thr | Ala | Gly | Ala | Thr | Ala | Ala | Ala | Thr | Gly |
|     | 3485 |     |     |     | 3490 |     |     |     | 3495 |     |     |     |
| Gly | Gly | Cys | Ala | Ala | Gly | Thr | Thr | Thr | Gly | Thr | Gly | Gly | Ala | Ala |
|     | 3500 |     |     |     | 3505 |     |     |     | 3510 |     |     |     |
| Thr | Thr | Gly | Gly | Thr | Thr | Thr | Ala | Ala | Cys | Ala | Thr | Ala | Ala | Cys |
|     | 3515 |     |     |     | 3520 |     |     |     | 3525 |     |     |     |
| Ala | Ala | Ala | Thr | Thr | Gly | Gly | Cys | Thr | Gly | Thr | Gly | Gly | Thr | Ala |
|     | 3530 |     |     |     | 3535 |     |     |     | 3540 |     |     |     |
| Thr | Ala | Thr | Ala | Ala | Ala | Ala | Thr | Thr | Ala | Thr | Thr | Cys | Ala | Thr |
|     | 3545 |     |     |     | 3550 |     |     |     | 3555 |     |     |     |
| Ala | Ala | Thr | Gly | Ala | Thr | Ala | Gly | Thr | Ala | Gly | Gly | Ala | Gly | Gly |
|     | 3560 |     |     |     | 3565 |     |     |     | 3570 |     |     |     |
| Cys | Thr | Thr | Gly | Gly | Thr | Ala | Gly | Gly | Thr | Thr | Ala | Ala | Gly |
|     | 3575 |     |     |     | 3580 |     |     |     | 3585 |     |     |     |
| Ala | Ala | Thr | Ala | Gly | Thr | Thr | Thr | Thr | Thr | Gly | Cys | Thr | Gly | Thr |
|     | 3590 |     |     |     | 3595 |     |     |     | 3600 |     |     |     |
| Ala | Cys | Thr | Thr | Thr | Cys | Thr | Ala | Thr | Ala | Gly | Thr | Gly | Ala | Ala |
|     | 3605 |     |     |     | 3610 |     |     |     | 3615 |     |     |     |
| Thr | Ala | Gly | Ala | Gly | Thr | Thr | Ala | Gly | Gly | Cys | Ala | Gly | Gly | Gly |
|     | 3620 |     |     |     | 3625 |     |     |     | 3630 |     |     |     |
| Ala | Thr | Ala | Thr | Thr | Cys | Ala | Cys | Cys | Ala | Thr | Ala | Thr | Cys |
|     | 3635 |     |     |     | 3640 |     |     |     | 3645 |     |     |     |
| Gly | Thr | Thr | Thr | Cys | Ala | Gly | Ala | Cys | Cys | Cys | Ala | Cys | Cys | Thr |
|     | 3650 |     |     |     | 3655 |     |     |     | 3660 |     |     |     |
| Cys | Cys | Cys | Ala | Ala | Cys | Cys | Cys | Cys | Gly | Ala | Gly | Gly | Gly | Gly |
|     | 3665 |     |     |     | 3670 |     |     |     | 3675 |     |     |     |
| Ala | Cys | Cys | Cys | Gly | Ala | Cys | Ala | Gly | Gly | Cys | Cys | Cys | Gly | Ala |
|     | 3680 |     |     |     | 3685 |     |     |     | 3690 |     |     |     |
| Ala | Gly | Gly | Ala | Ala | Thr | Ala | Gly | Ala | Ala | Gly | Ala | Ala | Gly | Ala |
|     | 3695 |     |     |     | 3700 |     |     |     | 3705 |     |     |     |
| Ala | Gly | Gly | Thr | Gly | Gly | Ala | Gly | Ala | Gly | Ala | Gly | Ala | Gly | Ala |
|     | 3710 |     |     |     | 3715 |     |     |     | 3720 |     |     |     |
| Cys | Ala | Gly | Ala | Gly | Ala | Cys | Ala | Gly | Ala | Thr | Cys | Cys | Ala | Thr |
|     | 3725 |     |     |     | 3730 |     |     |     | 3735 |     |     |     |
| Thr | Cys | Gly | Ala | Thr | Thr | Ala | Gly | Thr | Gly | Ala | Ala | Cys | Gly | Gly |
|     | 3740 |     |     |     | 3745 |     |     |     | 3750 |     |     |     |
| Ala | Thr | Cys | Thr | Cys | Gly | Ala | Cys | Gly | Gly | Thr | Ala | Thr | Cys | Gly |
|     | 3755 |     |     |     | 3760 |     |     |     | 3765 |     |     |     |
| Ala | Thr | Thr | Ala | Gly | Ala | Cys | Thr | Gly | Thr | Ala | Gly | Cys | Cys | Cys |

```
                3770                3775                3780

Ala Gly Gly Ala Ala Thr Ala Thr Gly Gly Cys Ala  Gly Cys Thr
    3785                3790                3795

Ala Gly Ala Thr Thr Gly Thr Ala Cys Ala Cys Ala  Thr Thr Thr
    3800                3805                3810

Ala Gly Ala Ala Gly Gly Ala Ala Ala Gly Thr  Thr Ala Thr
    3815                3820                3825

Cys Thr Thr Gly Gly Thr Ala Gly Cys Ala Gly Thr  Thr Cys Ala
    3830                3835                3840

Thr Gly Thr Ala Gly Cys Cys Ala Gly Thr Gly  Ala Thr Ala
    3845                3850                3855

Thr Ala Thr Ala Gly Ala Ala Gly Cys Ala Gly Ala  Ala Gly Thr
    3860                3865                3870

Ala Ala Thr Thr Cys Cys Ala Gly Cys Ala Gly Ala  Gly Ala Cys
    3875                3880                3885

Ala Gly Gly Gly Cys Ala Ala Gly Ala Ala Ala Cys  Ala Gly Cys
    3890                3895                3900

Ala Thr Ala Cys Thr Thr Cys Cys Thr Cys Thr Thr  Ala Ala Ala
    3905                3910                3915

Ala Thr Thr Ala Gly Cys Ala Gly Gly Ala Ala Gly  Ala Thr Gly
    3920                3925                3930

Gly Cys Cys Ala Gly Thr Ala Ala Ala Ala Cys  Ala Gly Thr
    3935                3940                3945

Ala Cys Ala Thr Ala Cys Ala Gly Ala Cys Ala Ala  Thr Gly Gly
    3950                3955                3960

Cys Ala Gly Cys Ala Ala Thr Thr Thr Cys Ala Cys  Cys Ala Gly
    3965                3970                3975

Thr Ala Cys Thr Ala Cys Ala Gly Thr Thr Ala Ala  Gly Gly Cys
    3980                3985                3990

Cys Gly Cys Cys Thr Gly Thr Gly Gly Thr Gly  Gly Gly Cys
    3995                4000                4005

Gly Gly Gly Gly Ala Thr Cys Ala Ala Gly Cys Ala  Gly Gly Ala
    4010                4015                4020

Ala Thr Thr Thr Gly Gly Cys Ala Thr Thr Cys Cys  Cys Thr Ala
    4025                4030                4035

Cys Ala Ala Thr Cys Cys Cys Ala Ala Ala Gly  Thr Cys Ala
    4040                4045                4050

Ala Gly Gly Ala Gly Thr Ala Ala Thr Ala Gly Ala  Ala Thr Cys
    4055                4060                4065

Thr Ala Thr Gly Ala Ala Thr Ala Ala Gly Ala  Ala Thr Thr
    4070                4075                4080

Ala Ala Ala Gly Ala Ala Ala Ala Thr Thr Ala Thr  Ala Gly Gly
    4085                4090                4095

Ala Cys Ala Gly Gly Thr Ala Ala Gly Ala Gly Ala  Thr Cys Ala
    4100                4105                4110

Gly Gly Cys Thr Gly Ala Ala Cys Ala Thr Cys Thr  Thr Ala Ala
    4115                4120                4125

Gly Ala Cys Ala Gly Cys Ala Gly Thr Ala Cys Ala  Ala Ala Thr
    4130                4135                4140

Gly Gly Cys Ala Gly Thr Ala Thr Thr Cys Ala Thr  Cys Cys Ala
    4145                4150                4155

Cys Ala Ala Thr Thr Thr Ala Ala Ala Ala Gly  Ala Ala Ala
    4160                4165                4170
```

-continued

Ala Gly Gly Gly Gly Gly Ala Thr Thr Gly Gly Gly Gly
4175                4180                4185

Gly Thr Ala Cys Ala Gly Thr Gly Cys Ala Gly Gly Gly Ala
4190                4195                4200

Ala Ala Gly Ala Ala Thr Ala Gly Thr Ala Gly Ala Cys Ala Thr
4205                4210                4215

Ala Ala Thr Ala Gly Cys Ala Ala Cys Ala Gly Ala Cys Ala Thr
4220                4225                4230

Ala Cys Ala Ala Ala Cys Thr Ala Ala Gly Ala Ala Thr Thr
4235                4240                4245

Ala Cys Ala Ala Ala Ala Ala Cys Ala Ala Ala Thr Thr Ala Cys
4250                4255                4260

Ala Ala Ala Ala Ala Thr Thr Cys Ala Ala Ala Ala Thr Thr Thr
4265                4270                4275

Thr Cys Gly Gly Gly Thr Thr Ala Thr Thr Ala Cys Ala Gly
4280                4285                4290

Gly Gly Ala Cys Ala Gly Cys Ala Gly Ala Gly Ala Thr Cys Cys
4295                4300                4305

Ala Gly Thr Thr Thr Gly Gly Cys Thr Gly Cys Ala Thr Ala Cys
4310                4315                4320

Gly Cys Gly Thr Cys Gly Thr Gly Ala Gly Gly Cys Thr Cys Cys
4325                4330                4335

Gly Gly Thr Gly Cys Cys Cys Gly Thr Cys Ala Gly Thr Gly Gly
4340                4345                4350

Gly Cys Ala Gly Ala Gly Cys Gly Cys Ala Cys Ala Thr Cys Gly
4355                4360                4365

Cys Cys Cys Ala Cys Ala Gly Thr Cys Cys Cys Gly Ala Gly
4370                4375                4380

Ala Ala Gly Thr Thr Gly Gly Gly Gly Gly Ala Gly Gly Gly
4385                4390                4395

Gly Thr Cys Gly Gly Cys Ala Ala Thr Gly Ala Ala Cys Cys
4400                4405                4410

Gly Gly Thr Gly Cys Cys Thr Ala Gly Ala Gly Ala Ala Gly Gly
4415                4420                4425

Thr Gly Gly Cys Gly Cys Gly Gly Gly Thr Ala Ala Ala Cys
4430                4435                4440

Thr Gly Gly Gly Ala Ala Ala Gly Thr Gly Ala Thr Gly Thr Cys
4445                4450                4455

Gly Thr Gly Thr Ala Cys Thr Gly Gly Cys Thr Cys Cys Gly Cys
4460                4465                4470

Cys Thr Thr Thr Thr Thr Cys Cys Cys Gly Ala Gly Gly Gly Thr
4475                4480                4485

Gly Gly Gly Gly Gly Ala Gly Ala Ala Cys Cys Gly Thr Ala Thr
4490                4495                4500

Ala Thr Ala Ala Gly Thr Gly Cys Ala Gly Thr Ala Gly Thr Cys
4505                4510                4515

Gly Cys Cys Gly Thr Gly Ala Ala Cys Gly Thr Thr Cys Thr Thr
4520                4525                4530

Thr Thr Thr Cys Gly Cys Ala Ala Cys Gly Gly Gly Thr Thr Thr
4535                4540                4545

Gly Cys Cys Gly Cys Cys Ala Gly Ala Ala Cys Ala Cys Ala Gly
4550                4555                4560

```
Gly Thr  Ala Ala Gly Thr  Gly Cys Cys Gly  Thr Gly Thr
    4565              4570              4575

Gly Gly  Thr Thr Cys Cys  Gly Cys Gly Gly  Gly Cys Cys Thr
    4580              4585              4590

Gly Gly  Cys Cys Thr Cys  Thr Thr Ala Cys  Gly Gly Gly Thr
    4595              4600              4605

Thr Ala  Thr Gly Gly Cys  Cys Thr Thr Gly  Cys Gly Thr Gly
    4610              4615              4620

Cys Cys  Thr Thr Gly Ala  Ala Thr Thr Ala  Cys Thr Cys Cys
    4625              4630              4635

Ala Cys  Cys Thr Gly Gly  Cys Thr Gly Cys  Ala Gly Thr Ala Cys
    4640              4645              4650

Gly Thr  Gly Ala Thr Thr  Cys Thr Thr Gly  Ala Thr Cys Cys Cys
    4655              4660              4665

Gly Ala  Gly Cys Thr Thr  Cys Gly Gly Gly  Thr Thr Gly Gly Ala
    4670              4675              4680

Ala Gly  Thr Gly Gly Gly  Thr Gly Gly Gly  Ala Gly Ala Gly Thr
    4685              4690              4695

Thr Cys  Gly Ala Gly Gly  Cys Thr Thr Gly  Cys Gly Cys Thr
    4700              4705              4710

Thr Ala  Ala Gly Gly Ala  Gly Cys Cys Cys  Cys Thr Thr Cys Gly
    4715              4720              4725

Cys Cys  Thr Cys Gly Thr  Gly Cys Thr Thr  Gly Ala Gly Thr Thr
    4730              4735              4740

Gly Ala  Gly Gly Cys Cys  Thr Gly Gly Cys  Cys Thr Gly Gly Gly
    4745              4750              4755

Cys Gly  Cys Thr Gly Gly  Gly Gly Cys Gly  Gly Cys Cys Gly Cys
    4760              4765              4770

Gly Thr  Gly Cys Gly Ala  Ala Thr Cys Thr  Gly Thr Gly Gly
    4775              4780              4785

Cys Ala  Cys Cys Thr Thr  Cys Gly Cys Gly  Gly Cys Thr Gly Thr
    4790              4795              4800

Cys Thr  Cys Gly Cys Thr  Gly Cys Thr Thr  Thr Cys Gly Ala Thr
    4805              4810              4815

Ala Ala  Gly Thr Cys Thr  Cys Thr Ala Gly  Cys Cys Ala Thr Thr
    4820              4825              4830

Thr Ala  Ala Ala Ala Thr  Thr Thr Thr Gly  Ala Thr Gly Ala
    4835              4840              4845

Cys Cys  Thr Gly Cys Thr  Gly Cys Gly Ala  Cys Gly Cys Thr Thr
    4850              4855              4860

Thr Thr  Thr Thr Thr Cys  Thr Gly Gly Cys  Ala Ala Gly Ala Thr
    4865              4870              4875

Ala Gly  Thr Cys Thr Thr  Gly Thr Ala Ala  Ala Thr Gly Cys Gly
    4880              4885              4890

Gly Gly  Cys Cys Ala Ala  Gly Ala Thr Cys  Thr Gly Cys Ala Cys
    4895              4900              4905

Ala Cys  Thr Gly Gly Thr  Ala Thr Thr Cys  Gly Gly Thr Thr
    4910              4915              4920

Thr Thr  Thr Gly Gly Gly  Gly Cys Cys Gly  Cys Gly Gly Gly Cys
    4925              4930              4935

Gly Gly  Cys Gly Ala Cys  Gly Gly Gly Cys  Cys Cys Gly Thr
    4940              4945              4950

Gly Cys  Gly Thr Cys Cys  Cys Ala Gly Cys  Gly Cys Ala Cys Ala
```

```
                4955                4960                4965
Thr Gly Thr Thr Cys Gly Gly Cys Gly Ala Gly Gly Cys Gly Gly
        4970            4975            4980
Gly Gly Cys Cys Thr Gly Cys Gly Ala Gly Cys Gly Cys Gly Gly
        4985            4990            4995
Cys Cys Ala Cys Cys Gly Ala Gly Ala Ala Thr Cys Gly Gly Ala
        5000            5005            5010
Cys Gly Gly Gly Gly Thr Ala Gly Thr Cys Thr Cys Ala Ala
        5015            5020            5025
Gly Cys Thr Gly Gly Cys Cys Gly Gly Cys Cys Thr Gly Cys Thr
        5030            5035            5040
Cys Thr Gly Gly Thr Gly Cys Cys Thr Gly Gly Cys Cys Thr Cys
        5045            5050            5055
Gly Cys Gly Cys Cys Gly Cys Cys Gly Thr Gly Thr Ala Thr Cys
        5060            5065            5070
Gly Cys Cys Cys Cys Gly Cys Cys Cys Thr Gly Gly Gly Cys Gly
        5075            5080            5085
Gly Cys Ala Ala Gly Gly Cys Thr Gly Gly Cys Cys Cys Gly Gly
        5090            5095            5100
Thr Cys Gly Gly Cys Ala Cys Cys Ala Gly Thr Thr Gly Cys Gly
        5105            5110            5115
Thr Gly Ala Gly Cys Gly Gly Ala Ala Ala Gly Ala Thr Gly Gly
        5120            5125            5130
Cys Cys Gly Cys Thr Thr Cys Cys Gly Gly Cys Cys Cys Thr
        5135            5140            5145
Gly Cys Thr Gly Cys Ala Gly Gly Ala Gly Cys Thr Cys Ala
        5150            5155            5160
Ala Ala Ala Thr Gly Gly Ala Gly Gly Ala Cys Gly Cys Gly Gly
        5165            5170            5175
Cys Gly Cys Thr Cys Gly Gly Gly Ala Gly Ala Gly Cys Gly Gly
        5180            5185            5190
Gly Cys Gly Gly Gly Thr Gly Ala Gly Thr Cys Ala Cys Cys Cys
        5195            5200            5205
Ala Cys Ala Cys Ala Ala Ala Gly Gly Ala Ala Ala Ala Gly Gly
        5210            5215            5220
Gly Cys Cys Thr Thr Thr Cys Cys Gly Thr Cys Cys Thr Cys Ala
        5225            5230            5235
Gly Cys Cys Gly Thr Cys Gly Cys Thr Thr Cys Ala Thr Gly Thr
        5240            5245            5250
Gly Ala Cys Thr Cys Cys Ala Cys Thr Gly Ala Gly Thr Ala Cys
        5255            5260            5265
Cys Gly Gly Gly Cys Gly Cys Cys Gly Thr Cys Cys Ala Gly Gly
        5270            5275            5280
Cys Ala Cys Cys Thr Cys Gly Ala Thr Thr Ala Gly Thr Thr Cys
        5285            5290            5295
Thr Cys Gly Thr Gly Cys Thr Thr Thr Gly Gly Ala Gly Thr
        5300            5305            5310
Ala Cys Gly Thr Cys Gly Thr Cys Thr Thr Thr Ala Gly Gly Thr
        5315            5320            5325
Thr Gly Gly Gly Gly Gly Ala Gly Gly Gly Thr Thr Thr
        5330            5335            5340
Thr Ala Thr Gly Cys Gly Ala Thr Gly Gly Ala Gly Thr Thr Thr
        5345            5350            5355
```

```
Cys Cys Cys Cys Ala Cys Ala Cys Thr Gly Ala Gly  Thr Gly Gly
    5360             5365             5370

Gly Thr Gly Gly Ala Gly Ala Cys Thr Gly Ala Ala  Gly Thr Thr
    5375             5380             5385

Ala Gly Gly Cys Cys Ala Gly Cys Thr Thr Gly Gly  Cys Ala Cys
    5390             5395             5400

Thr Thr Gly Ala Thr Gly Thr Ala Ala Thr Thr Cys  Thr Cys Cys
    5405             5410             5415

Thr Thr Gly Gly Ala Ala Thr Thr Thr Gly Cys Cys  Cys Thr Thr
    5420             5425             5430

Thr Thr Thr Gly Ala Gly Thr Thr Thr Gly Gly Ala  Thr Cys Thr
    5435             5440             5445

Thr Gly Gly Thr Thr Cys Ala Thr Thr Cys Thr Cys  Ala Ala Gly
    5450             5455             5460

Cys Cys Thr Cys Ala Gly Ala Cys Ala Gly Thr Gly  Gly Thr Thr
    5465             5470             5475

Cys Ala Ala Ala Gly Thr Thr Thr Thr Thr Thr Thr  Cys Thr Thr
    5480             5485             5490

Cys Cys Ala Thr Thr Thr Cys Ala Gly Gly Thr Gly  Thr Cys Gly
    5495             5500             5505

Thr Gly Ala Gly Cys Thr Ala Gly Cys Thr Cys Thr  Ala Gly Ala
    5510             5515             5520

Gly Cys Cys Ala Cys Ala Thr Gly Gly Cys Gly  Cys Gly Cys
    5525             5530             5535

Gly Cys Ala Thr Cys Ala Gly Gly Cys Thr Cys Cys  Gly Ala Gly
    5540             5545             5550

Ala Gly Gly Cys Ala Cys Cys Thr Gly Cys Thr Gly  Cys Thr Cys
    5555             5560             5565

Ala Thr Cys Thr Ala Cys Ala Cys Thr Gly Gly Cys  Gly Gly Cys
    5570             5575             5580

Ala Cys Thr Thr Thr Gly Gly Gly Cys Ala Thr Gly  Cys Ala Gly
    5585             5590             5595

Ala Gly Cys Ala Ala Gly Gly Gly Cys Gly Gly Gly  Gly Thr Gly
    5600             5605             5610

Cys Thr Cys Gly Thr Cys Cys Cys Gly Gly Cys  Cys Cys Ala
    5615             5620             5625

Gly Gly Cys Cys Thr Gly Gly Thr Cys Ala Cys Thr  Cys Thr Gly
    5630             5635             5640

Cys Thr Gly Cys Gly Gly Ala Cys Cys Cys Thr Gly  Cys Cys Cys
    5645             5650             5655

Ala Thr Gly Thr Thr Cys Cys Ala Thr Gly Ala Cys  Ala Ala Gly
    5660             5665             5670

Gly Ala Gly Thr Thr Cys Gly Cys Cys Cys Ala Gly  Gly Cys Cys
    5675             5680             5685

Cys Ala Gly Gly Gly Cys Cys Thr Cys Cys Thr Gly  Gly Ala Cys
    5690             5695             5700

Cys Ala Thr Gly Cys Thr Cys Thr Gly Gly Cys Gly  Cys Thr Gly
    5705             5710             5715

Cys Cys Cys Cys Cys Thr Gly Cys Cys Ala Gly Cys  Cys Ala Cys
    5720             5725             5730

Gly Gly Cys Cys Cys Cys Ala Gly Gly Gly Thr Cys  Cys Thr Cys
    5735             5740             5745
```

-continued

```
Thr Ala Cys Ala Cys Gly Gly Thr Gly Cys Thr Gly Gly Ala Gly
            5750            5755            5760

Thr Gly Cys Cys Ala Gly Cys Cys Cys Thr Cys Thr Thr Gly
            5765            5770            5775

Gly Ala Thr Thr Cys Cys Ala Gly Cys Gly Ala Cys Ala Thr Gly
            5780            5785            5790

Ala Cys Cys Ala Thr Cys Gly Ala Thr Gly Ala Thr Thr Gly Gly
            5795            5800            5805

Ala Thr Thr Cys Gly Cys Ala Thr Ala Gly Cys Cys Ala Ala Gly
            5810            5815            5820

Ala Thr Cys Ala Thr Ala Gly Ala Gly Ala Gly Gly Cys Ala Cys
            5825            5830            5835

Thr Ala Thr Gly Ala Gly Cys Ala Gly Thr Ala Cys Cys Ala Ala
            5840            5845            5850

Gly Gly Cys Thr Thr Thr Gly Thr Gly Thr Thr Ala Thr Cys
            5855            5860            5865

Cys Ala Cys Gly Gly Cys Ala Cys Cys Gly Ala Cys Ala Cys Cys
            5870            5875            5880

Ala Thr Gly Gly Cys Cys Thr Cys Thr Gly Gly Gly Cys Cys
            5885            5890            5895

Thr Cys Cys Ala Thr Gly Cys Thr Gly Thr Cys Cys Thr Thr Cys
            5900            5905            5910

Ala Thr Gly Cys Thr Gly Gly Ala Ala Ala Cys Cys Thr Gly
            5915            5920            5925

Cys Ala Cys Ala Ala Ala Cys Cys Ala Gly Thr Cys Ala Thr Cys
            5930            5935            5940

Cys Thr Cys Ala Cys Thr Gly Gly Cys Gly Cys Cys Cys Ala Gly
            5945            5950            5955

Gly Thr Gly Cys Cys Ala Ala Thr Cys Cys Gly Thr Gly Thr Gly
            5960            5965            5970

Cys Thr Gly Thr Gly Gly Ala Ala Thr Gly Ala Cys Gly Cys Cys
            5975            5980            5985

Cys Gly Gly Gly Ala Ala Ala Cys Cys Thr Gly Cys Thr Gly
            5990            5995            6000

Gly Gly Gly Gly Cys Gly Thr Thr Gly Cys Thr Thr Gly Thr Gly
            6005            6010            6015

Gly Cys Cys Gly Gly Cys Cys Ala Ala Thr Ala Cys Ala Thr Cys
            6020            6025            6030

Ala Thr Cys Cys Cys Thr Gly Ala Gly Gly Thr Cys Thr Gly Cys
            6035            6040            6045

Cys Thr Gly Thr Thr Thr Ala Thr Gly Ala Ala Cys Ala Gly Thr
            6050            6055            6060

Cys Ala Gly Cys Thr Gly Thr Thr Thr Cys Gly Gly Gly Gly Ala
            6065            6070            6075

Ala Ala Cys Cys Gly Gly Gly Thr Ala Ala Cys Cys Ala Ala Gly
            6080            6085            6090

Gly Thr Gly Gly Ala Cys Thr Cys Cys Cys Ala Gly Ala Ala Gly
            6095            6100            6105

Thr Thr Thr Gly Ala Gly Gly Cys Cys Thr Thr Cys Thr Gly Cys
            6110            6115            6120

Thr Cys Cys Cys Cys Ala Ala Thr Cys Thr Gly Thr Cys Cys
            6125            6130            6135

Cys Cys Ala Cys Thr Ala Gly Cys Cys Ala Cys Thr Gly Thr Gly
```

```
                    6140            6145            6150
Gly Gly Cys Gly Cys Gly Gly Ala Thr Gly Thr Cys Ala Cys Ala
            6155            6160            6165
Ala Thr Thr Gly Cys Cys Thr Gly Gly Ala Cys Cys Thr Gly
        6170            6175            6180
Gly Thr Gly Cys Gly Cys Ala Ala Gly Gly Thr Cys Ala Ala Gly
            6185            6190            6195
Thr Gly Gly Ala Ala Gly Gly Ala Cys Cys Cys Gly Cys Thr Gly
        6200            6205            6210
Gly Thr Gly Gly Thr Gly Cys Ala Cys Ala Gly Cys Ala Ala Cys
            6215            6220            6225
Ala Thr Gly Gly Ala Gly Cys Ala Cys Gly Ala Cys Gly Thr Gly
        6230            6235            6240
Gly Cys Ala Cys Thr Gly Cys Thr Gly Cys Gly Cys Cys Thr Cys
            6245            6250            6255
Thr Ala Cys Cys Cys Thr Gly Gly Cys Ala Thr Cys Cys Gly
        6260            6265            6270
Gly Cys Cys Thr Cys Cys Cys Thr Gly Gly Thr Cys Cys Gly Gly
            6275            6280            6285
Gly Cys Ala Thr Thr Cys Cys Thr Gly Cys Ala Gly Cys Cys Cys
        6290            6295            6300
Cys Cys Gly Cys Thr Cys Ala Ala Gly Gly Gly Cys Gly Thr Gly
            6305            6310            6315
Gly Thr Cys Cys Thr Gly Gly Ala Gly Ala Cys Cys Thr Thr Cys
        6320            6325            6330
Gly Gly Cys Thr Cys Thr Gly Gly Cys Ala Ala Cys Gly Gly Gly
            6335            6340            6345
Cys Cys Gly Ala Gly Cys Ala Ala Gly Cys Cys Cys Gly Ala Cys
        6350            6355            6360
Cys Thr Gly Cys Thr Gly Cys Ala Gly Gly Ala Gly Thr Thr Gly
            6365            6370            6375
Cys Gly Gly Gly Cys Cys Gly Cys Gly Gly Cys Cys Cys Ala Gly
        6380            6385            6390
Cys Gly Cys Gly Gly Cys Cys Thr Cys Ala Thr Cys Ala Thr Gly
            6395            6400            6405
Gly Thr Cys Ala Ala Cys Thr Gly Cys Ala Gly Cys Cys Ala Gly
        6410            6415            6420
Thr Gly Cys Cys Thr Gly Cys Gly Gly Gly Gly Thr Cys Thr
            6425            6430            6435
Gly Thr Gly Ala Cys Cys Cys Cys Gly Gly Gly Cys Thr Ala Thr
        6440            6445            6450
Gly Cys Cys Ala Cys Gly Ala Gly Cys Thr Thr Gly Gly Cys Gly
            6455            6460            6465
Gly Gly Cys Gly Cys Ala Ala Cys Ala Thr Cys Gly Thr Gly
        6470            6475            6480
Thr Cys Cys Gly Gly Cys Thr Thr Ala Gly Ala Cys Ala Thr Gly
            6485            6490            6495
Ala Cys Cys Thr Cys Ala Gly Ala Gly Gly Cys Cys Gly Cys Gly
        6500            6505            6510
Cys Thr Gly Gly Cys Thr Ala Ala Gly Cys Thr Gly Thr Cys Cys
            6515            6520            6525
Thr Ala Cys Gly Thr Gly Thr Gly Gly Gly Cys Cys Thr Gly
        6530            6535            6540
```

```
Cys Cys Gly Gly Ala Gly Cys Thr Gly Ala Gly Cys Cys Thr Gly
6545                6550                6555
Gly Ala Gly Cys Gly Cys Ala Gly Gly Cys Ala Gly Gly Ala Gly
6560                6565                6570
Cys Thr Gly Cys Thr Gly Gly Cys Cys Ala Ala Gly Gly Ala Thr
6575                6580                6585
Cys Thr Thr Cys Gly Cys Gly Gly Gly Gly Ala Ala Ala Thr Gly
6590                6595                6600
Ala Cys Ala Cys Thr Gly Cys Cys Cys Ala Cys Gly Gly Cys Ala
6605                6610                6615
Gly Ala Cys Cys Thr Gly Cys Ala Cys Cys Ala Gly Thr Cys Cys
6620                6625                6630
Thr Cys Thr Cys Cys Gly Cys Cys Gly Gly Gly Cys Ala Gly Cys
6635                6640                6645
Ala Cys Ala Cys Thr Gly Gly Gly Gly Cys Ala Ala Gly Gly Thr
6650                6655                6660
Gly Thr Cys Gly Cys Cys Cys Gly Gly Cys Thr Cys Thr Thr Thr
6665                6670                6675
Ala Gly Thr Cys Thr Gly Thr Thr Cys Gly Gly Thr Thr Gly Cys
6680                6685                6690
Cys Ala Gly Gly Ala Gly Gly Ala Ala Gly Ala Thr Thr Cys Gly
6695                6700                6705
Gly Thr Gly Cys Ala Gly Gly Ala Cys Gly Cys Cys Gly Thr Gly
6710                6715                6720
Ala Thr Gly Cys Cys Cys Ala Gly Cys Cys Thr Gly Gly Cys Cys
6725                6730                6735
Cys Thr Gly Gly Cys Cys Thr Gly Cys Cys Cys Ala Thr
6740                6745                6750
Gly Cys Thr Gly Gly Thr Gly Ala Ala Cys Thr Cys Gly Ala Gly
6755                6760                6765
Gly Cys Thr Cys Thr Gly Cys Ala Gly Gly Cys Ala Cys Thr Thr
6770                6775                6780
Ala Thr Gly Gly Ala Gly Cys Thr Gly Gly Gly Cys Ala Gly Thr
6785                6790                6795
Gly Ala Cys Cys Thr Gly Cys Gly Cys Thr Ala Ala Ala Gly Gly
6800                6805                6810
Gly Ala Cys Thr Cys Thr Ala Ala Thr Gly Gly Cys Cys Ala Ala
6815                6820                6825
Ala Cys Cys Cys Thr Gly Thr Gly Cys Ala Thr Gly Thr Gly
6830                6835                6840
Gly Cys Thr Gly Cys Thr Cys Gly Gly Ala Ala Thr Gly Gly Gly
6845                6850                6855
Cys Gly Thr Gly Ala Thr Gly Cys Gly Thr Gly Gly Thr Cys
6860                6865                6870
Ala Cys Cys Ala Thr Gly Cys Thr Gly Cys Thr Gly Cys Ala Cys
6875                6880                6885
Ala Gly Ala Gly Gly Cys Ala Thr Gly Gly Ala Thr Gly Thr Cys
6890                6895                6900
Ala Ala Thr Gly Cys Cys Cys Gly Ala Gly Ala Cys Cys Gly Ala
6905                6910                6915
Gly Ala Cys Gly Gly Cys Cys Thr Cys Ala Gly Cys Cys Cys Ala
6920                6925                6930
```

```
Cys Thr Gly Cys Thr Gly Thr Thr Gly Gly Cys Thr Gly Thr Ala
    6935            6940                6945

Cys Ala Gly Gly Gly Cys Ala Gly Gly Cys Ala Thr Cys Gly Gly
    6950            6955                6960

Gly Ala Ala Thr Gly Cys Ala Thr Cys Ala Gly Gly Cys Thr Gly
    6965            6970                6975

Cys Thr Gly Cys Gly Gly Ala Ala Gly Gly Cys Thr Gly Gly Gly
    6980            6985                6990

Gly Cys Thr Thr Gly Cys Cys Thr Gly Thr Gly Cys Cys Cys Cys
    6995            7000                7005

Cys Ala Gly Gly Ala Cys Cys Thr Gly Ala Ala Gly Gly Ala Thr
    7010            7015                7020

Gly Cys Ala Gly Gly Ala Cys Cys Gly Ala Gly Cys Thr Gly
    7025            7030                7035

Thr Gly Cys Ala Gly Gly Cys Thr Gly Gly Cys Ala Thr Cys Cys
    7040            7045                7050

Ala Gly Gly Gly Cys Thr Gly Ala Cys Ala Thr Gly Gly Ala Ala
    7055            7060                7065

Gly Gly Cys Cys Thr Gly Cys Ala Gly Gly Cys Ala Thr Gly Gly
    7070            7075                7080

Gly Gly Gly Cys Ala Gly Gly Cys Thr Gly Gly Gly Cys Cys
    7085            7090                7095

Gly Ala Cys Cys Thr Gly Cys Ala Gly Cys Ala Gly Cys Cys Gly
    7100            7105                7110

Gly Gly Cys Thr Ala Thr Gly Ala Thr Gly Gly Gly Cys Gly Cys
    7115            7120                7125

Ala Gly Cys Gly Cys Thr Cys Thr Gly Thr Gly Thr Gly Thr Cys
    7130            7135                7140

Gly Cys Ala Gly Ala Ala Gly Cys Ala Gly Cys Cys Gly Gly Gly
    7145            7150                7155

Ala Ala Cys Cys Ala Gly Gly Ala Gly Gly Thr Gly Cys Thr Gly
    7160            7165                7170

Gly Cys Cys Cys Thr Thr Cys Thr Gly Cys Gly Gly Ala Ala Cys
    7175            7180                7185

Cys Thr Gly Gly Cys Ala Cys Thr Thr Gly Thr Ala Gly Gly Cys
    7190            7195                7200

Cys Cys Gly Gly Ala Ala Gly Thr Gly Cys Cys Gly Cys Cys Thr
    7205            7210                7215

Gly Cys Cys Ala Thr Cys Gly Ala Thr Thr Ala Cys Ala Ala Gly
    7220            7225                7230

Gly Ala Thr Gly Ala Cys Gly Ala Thr Gly Ala Cys Ala Ala Gly
    7235            7240                7245

Thr Cys Cys Gly Gly Ala Gly Gly Cys Ala Gly Cys Gly Gly Ala
    7250            7255                7260

Gly Ala Gly Gly Gly Cys Ala Gly Ala Gly Gly Ala Ala Gly Thr
    7265            7270                7275

Cys Thr Thr Cys Thr Ala Ala Cys Ala Thr Gly Cys Gly Gly Thr
    7280            7285                7290

Gly Ala Cys Gly Thr Gly Gly Ala Gly Gly Ala Gly Ala Ala Thr
    7295            7300                7305

Cys Cys Cys Gly Gly Cys Cys Thr Ala Gly Ala Gly Cys Cys
    7310            7315                7320

Ala Cys Cys Ala Thr Gly Gly Cys Cys Thr Thr Ala Cys Cys Ala
```

-continued

```
    7325                7330                7335

Gly Thr  Gly Ala Cys Cys Gly  Cys Cys Thr Thr Gly  Cys Thr Cys
    7340                7345                7350

Cys Thr  Gly Cys Cys Gly Cys  Thr Gly Gly Cys Cys  Thr Thr Gly
    7355                7360                7365

Cys Thr  Gly Cys Thr Cys Cys  Ala Cys Gly Cys Cys  Gly Cys Cys
    7370                7375                7380

Ala Gly  Gly Cys Cys Gly Gly  Gly Ala Thr Cys Cys  Cys Ala Gly
    7385                7390                7395

Gly Thr  Ala Cys Ala Ala Cys  Thr Gly Cys Ala Gly  Cys Ala Gly
    7400                7405                7410

Thr Cys  Thr Gly Gly Gly Cys  Cys Thr Gly Ala Gly  Cys Thr Gly
    7415                7420                7425

Gly Ala  Gly Ala Ala Gly Cys  Cys Thr Gly Gly Cys  Gly Cys Thr
    7430                7435                7440

Thr Cys  Ala Gly Thr Gly Ala  Ala Gly Ala Thr Ala  Thr Cys Cys
    7445                7450                7455

Thr Gly  Cys Ala Ala Gly Gly  Cys Thr Thr Cys Thr  Gly Gly Thr
    7460                7465                7470

Thr Ala  Cys Thr Cys Ala Thr  Thr Cys Ala Cys Thr  Gly Gly Cys
    7475                7480                7485

Thr Ala  Cys Ala Cys Cys Ala  Thr Gly Ala Ala Cys  Thr Gly Gly
    7490                7495                7500

Gly Thr  Gly Ala Ala Gly Cys  Ala Gly Ala Gly Cys  Cys Ala Thr
    7505                7510                7515

Gly Gly  Ala Ala Ala Gly Ala  Gly Cys Cys Thr Thr  Gly Ala Gly
    7520                7525                7530

Thr Gly  Gly Ala Thr Thr Gly  Gly Ala Cys Thr Thr  Ala Thr Thr
    7535                7540                7545

Ala Cys  Thr Cys Cys Thr Thr  Ala Cys Ala Ala Thr  Gly Gly Thr
    7550                7555                7560

Gly Cys  Thr Thr Cys Thr Ala  Gly Cys Thr Ala Cys  Ala Ala Cys
    7565                7570                7575

Cys Ala  Gly Ala Ala Gly Thr  Thr Cys Ala Gly Gly  Gly Gly Cys
    7580                7585                7590

Ala Ala  Gly Gly Cys Cys Ala  Cys Ala Thr Thr Ala  Ala Cys Thr
    7595                7600                7605

Gly Thr  Ala Gly Ala Cys Ala  Ala Gly Thr Cys Ala  Thr Cys Cys
    7610                7615                7620

Ala Gly  Cys Ala Cys Ala Gly  Cys Cys Thr Ala Cys  Ala Thr Gly
    7625                7630                7635

Gly Ala  Cys Cys Thr Cys Cys  Thr Cys Ala Gly Thr  Cys Thr Gly
    7640                7645                7650

Ala Cys  Ala Thr Cys Thr Gly  Ala Ala Gly Ala Cys  Thr Cys Thr
    7655                7660                7665

Gly Cys  Ala Gly Thr Cys Thr  Ala Thr Thr Thr Cys  Thr Gly Thr
    7670                7675                7680

Gly Cys  Ala Ala Gly Gly Gly  Gly Gly Gly Gly Thr  Thr Ala Cys
    7685                7690                7695

Gly Ala  Cys Gly Gly Gly Ala  Gly Gly Gly Gly Thr  Thr Thr Thr
    7700                7705                7710

Gly Ala  Cys Thr Ala Cys Thr  Gly Gly Gly Gly Cys  Cys Ala Ala
    7715                7720                7725
```

-continued

```
Gly Gly Gly Ala Cys Cys Ala Cys Gly Thr Cys Ala Cys Cys
    7730            7735                7740
Gly Thr Cys Thr Cys Cys Thr Cys Ala Gly Gly Thr Gly Gly Ala
    7745            7750                7755
Gly Gly Cys Gly Gly Thr Thr Cys Ala Gly Gly Cys Gly Gly Cys
    7760            7765                7770
Gly Gly Thr Gly Gly Cys Thr Cys Thr Gly Gly Cys Gly Gly Thr
    7775            7780                7785
Gly Gly Cys Gly Gly Ala Thr Cys Gly Gly Ala Cys Ala Thr Cys
    7790            7795                7800
Gly Ala Gly Cys Thr Cys Ala Cys Thr Cys Ala Gly Thr Cys Thr
    7805            7810                7815
Cys Cys Ala Gly Cys Ala Ala Thr Cys Ala Thr Gly Thr Cys Thr
    7820            7825                7830
Gly Cys Ala Thr Cys Thr Cys Cys Ala Gly Gly Gly Ala Gly Gly
    7835            7840                7845
Ala Ala Gly Gly Thr Cys Ala Cys Cys Ala Thr Gly Ala Cys Cys
    7850            7855                7860
Thr Gly Cys Ala Gly Thr Gly Cys Cys Ala Gly Cys Thr Cys Ala
    7865            7870                7875
Ala Gly Thr Gly Thr Ala Ala Gly Thr Thr Ala Cys Ala Thr Gly
    7880            7885                7890
Cys Ala Cys Thr Gly Gly Thr Ala Cys Cys Ala Gly Cys Ala Gly
    7895            7900                7905
Ala Ala Gly Thr Cys Ala Gly Gly Cys Ala Cys Cys Thr Cys Cys
    7910            7915                7920
Cys Cys Cys Ala Ala Ala Ala Gly Ala Thr Gly Gly Ala Thr Thr
    7925            7930                7935
Thr Ala Thr Gly Ala Cys Ala Cys Ala Thr Cys Cys Ala Ala Ala
    7940            7945                7950
Cys Thr Gly Gly Cys Thr Thr Cys Thr Gly Gly Ala Gly Thr Cys
    7955            7960                7965
Cys Cys Ala Gly Gly Thr Cys Gly Cys Thr Thr Cys Ala Gly Thr
    7970            7975                7980
Gly Gly Cys Ala Gly Thr Gly Gly Gly Thr Cys Thr Gly Gly Ala
    7985            7990                7995
Ala Ala Cys Thr Cys Thr Thr Ala Cys Thr Cys Thr Cys Thr Cys
    8000            8005                8010
Ala Cys Ala Ala Thr Cys Ala Gly Cys Ala Gly Cys Gly Thr Gly
    8015            8020                8025
Gly Ala Gly Gly Cys Thr Gly Ala Ala Gly Ala Thr Gly Ala Thr
    8030            8035                8040
Gly Cys Ala Ala Cys Thr Thr Ala Thr Thr Ala Cys Thr Gly Cys
    8045            8050                8055
Cys Ala Gly Cys Ala Gly Thr Gly Gly Ala Gly Thr Gly Gly Thr
    8060            8065                8070
Thr Ala Cys Cys Cys Thr Cys Thr Cys Ala Cys Gly Thr Thr Cys
    8075            8080                8085
Gly Gly Thr Gly Cys Thr Gly Gly Gly Ala Cys Ala Ala Ala Gly
    8090            8095                8100
Thr Thr Gly Gly Ala Ala Ala Thr Cys Ala Ala Ala Gly Cys Thr
    8105            8110                8115
```

-continued

Ala Gly Cys Gly Ala Thr Thr Ala Thr Ala Ala Ala Gly Ala Thr
8120 8125 8130

Gly Ala Thr Gly Ala Thr Gly Ala Thr Ala Ala Ala Thr Cys Thr
8135 8140 8145

Ala Gly Cys Ala Cys Cys Ala Cys Gly Ala Cys Gly Cys Cys Ala
8150 8155 8160

Gly Cys Gly Cys Cys Gly Cys Gly Ala Cys Cys Ala Cys Cys Ala
8165 8170 8175

Ala Cys Ala Cys Cys Gly Gly Cys Gly Cys Cys Cys Ala Cys Cys
8180 8185 8190

Ala Thr Cys Gly Cys Gly Thr Cys Gly Cys Ala Gly Cys Cys Cys
8195 8200 8205

Cys Thr Gly Thr Cys Cys Cys Thr Gly Cys Gly Cys Cys Cys Ala
8210 8215 8220

Gly Ala Gly Gly Cys Gly Thr Gly Cys Cys Gly Gly Cys Cys Ala
8225 8230 8235

Gly Cys Gly Gly Cys Gly Gly Gly Gly Gly Gly Cys Gly Cys Ala
8240 8245 8250

Gly Thr Gly Cys Ala Cys Ala Cys Gly Ala Gly Gly Gly Gly Gly
8255 8260 8265

Cys Thr Gly Gly Ala Cys Thr Thr Cys Gly Cys Cys Thr Gly Thr
8270 8275 8280

Gly Ala Thr Ala Thr Cys Thr Ala Cys Ala Thr Cys Thr Gly Gly
8285 8290 8295

Gly Cys Gly Cys Cys Cys Thr Thr Gly Gly Cys Cys Gly Gly Gly
8300 8305 8310

Ala Cys Thr Thr Gly Thr Gly Gly Gly Gly Thr Cys Cys Thr Thr
8315 8320 8325

Cys Thr Cys Cys Thr Gly Thr Cys Ala Cys Thr Gly Gly Thr Thr
8330 8335 8340

Ala Thr Cys Ala Cys Cys Cys Thr Thr Thr Ala Cys Thr Gly Cys
8345 8350 8355

Gly Cys Cys Thr Thr Thr Ala Thr Thr Ala Thr Thr Thr Thr Cys
8360 8365 8370

Thr Gly Gly Gly Thr Gly Ala Gly Gly Ala Gly Thr Ala Ala Gly
8375 8380 8385

Ala Gly Gly Ala Gly Cys Ala Gly Gly Cys Thr Cys Cys Thr Gly
8390 8395 8400

Cys Ala Cys Ala Gly Thr Gly Ala Cys Thr Ala Cys Ala Thr Gly
8405 8410 8415

Ala Ala Cys Ala Thr Gly Ala Cys Thr Cys Cys Cys Cys Gly Cys
8420 8425 8430

Cys Gly Cys Cys Cys Cys Gly Gly Gly Cys Cys Cys Ala Cys Cys
8435 8440 8445

Cys Gly Cys Ala Ala Gly Cys Ala Thr Thr Ala Cys Cys Ala Gly
8450 8455 8460

Cys Cys Cys Thr Ala Thr Gly Cys Cys Cys Cys Ala Cys Cys Ala
8465 8470 8475

Cys Gly Cys Gly Ala Cys Thr Thr Cys Gly Cys Ala Gly Cys Cys
8480 8485 8490

Thr Ala Thr Cys Gly Cys Thr Cys Cys Ala Gly Ala Gly Thr Gly
8495 8500 8505

Ala Ala Gly Thr Thr Cys Ala Gly Cys Ala Gly Gly Ala Gly Cys

|   |   |   |   |   |   |   |   |   |   |   |   |
|---|---|---|---|---|---|---|---|---|---|---|---|
|   |   | 8510 |   |   |   | 8515 |   |   |   | 8520 |   |
| Gly | Cys | Ala | Gly | Ala | Cys | Gly | Cys | Cys | Cys | Cys | Gly | Cys | Gly |
|   |   | 8525 |   |   |   | 8530 |   |   |   | 8535 |   |
| Thr | Ala | Cys | Cys | Ala | Gly | Cys | Ala | Gly | Gly | Cys | Cys | Ala | Gly |
|   |   | 8540 |   |   |   | 8545 |   |   |   | 8550 |   |
| Ala | Ala | Cys | Cys | Ala | Gly | Cys | Thr | Cys | Thr | Ala | Thr | Ala | Ala | Cys |
|   |   | 8555 |   |   |   | 8560 |   |   |   | 8565 |   |
| Gly | Ala | Gly | Cys | Thr | Cys | Ala | Ala | Thr | Cys | Thr | Ala | Gly | Gly | Ala |
|   |   | 8570 |   |   |   | 8575 |   |   |   | 8580 |   |
| Cys | Gly | Ala | Ala | Gly | Ala | Gly | Ala | Gly | Gly | Ala | Gly | Thr | Ala | Cys |
|   |   | 8585 |   |   |   | 8590 |   |   |   | 8595 |   |
| Gly | Ala | Thr | Gly | Thr | Thr | Thr | Thr | Gly | Gly | Ala | Cys | Ala | Ala | Gly |
|   |   | 8600 |   |   |   | 8605 |   |   |   | 8610 |   |
| Ala | Gly | Ala | Cys | Gly | Thr | Gly | Gly | Cys | Cys | Gly | Gly | Ala | Cys |
|   |   | 8615 |   |   |   | 8620 |   |   |   | 8625 |   |
| Cys | Cys | Thr | Gly | Ala | Gly | Ala | Thr | Gly | Gly | Gly | Gly | Gly | Ala |
|   |   | 8630 |   |   |   | 8635 |   |   |   | 8640 |   |
| Ala | Ala | Gly | Cys | Cys | Gly | Ala | Gly | Ala | Ala | Gly | Ala | Ala | Gly |
|   |   | 8645 |   |   |   | 8650 |   |   |   | 8655 |   |
| Ala | Ala | Cys | Cys | Cys | Thr | Cys | Ala | Gly | Gly | Ala | Ala | Gly | Gly | Cys |
|   |   | 8660 |   |   |   | 8665 |   |   |   | 8670 |   |
| Cys | Thr | Gly | Thr | Ala | Cys | Ala | Ala | Thr | Gly | Ala | Ala | Cys | Thr | Gly |
|   |   | 8675 |   |   |   | 8680 |   |   |   | 8685 |   |
| Cys | Ala | Gly | Ala | Ala | Ala | Gly | Ala | Thr | Ala | Ala | Gly | Ala | Thr | Gly |
|   |   | 8690 |   |   |   | 8695 |   |   |   | 8700 |   |
| Gly | Cys | Gly | Gly | Ala | Gly | Gly | Cys | Cys | Thr | Ala | Cys | Ala | Gly | Thr |
|   |   | 8705 |   |   |   | 8710 |   |   |   | 8715 |   |
| Gly | Ala | Gly | Ala | Thr | Thr | Gly | Gly | Gly | Ala | Thr | Gly | Ala | Ala | Ala |
|   |   | 8720 |   |   |   | 8725 |   |   |   | 8730 |   |
| Gly | Gly | Cys | Gly | Ala | Gly | Cys | Gly | Cys | Cys | Gly | Gly | Ala | Gly | Gly |
|   |   | 8735 |   |   |   | 8740 |   |   |   | 8745 |   |
| Gly | Gly | Cys | Ala | Ala | Gly | Gly | Gly | Gly | Cys | Ala | Cys | Gly | Ala | Thr |
|   |   | 8750 |   |   |   | 8755 |   |   |   | 8760 |   |
| Gly | Gly | Cys | Cys | Thr | Thr | Thr | Ala | Cys | Cys | Ala | Gly | Gly | Gly | Thr |
|   |   | 8765 |   |   |   | 8770 |   |   |   | 8775 |   |
| Cys | Thr | Cys | Ala | Gly | Thr | Ala | Cys | Ala | Gly | Cys | Cys | Ala | Cys | Cys |
|   |   | 8780 |   |   |   | 8785 |   |   |   | 8790 |   |
| Ala | Ala | Gly | Gly | Ala | Cys | Ala | Cys | Cys | Thr | Ala | Cys | Gly | Ala | Cys |
|   |   | 8795 |   |   |   | 8800 |   |   |   | 8805 |   |
| Gly | Cys | Cys | Cys | Thr | Thr | Cys | Ala | Cys | Ala | Thr | Gly | Cys | Ala | Gly |
|   |   | 8810 |   |   |   | 8815 |   |   |   | 8820 |   |
| Gly | Cys | Cys | Cys | Thr | Gly | Cys | Cys | Cys | Cys | Thr | Cys | Gly | Cys |
|   |   | 8825 |   |   |   | 8830 |   |   |   | 8835 |   |
| Gly | Gly | Thr | Gly | Gly | Cys | Gly | Gly | Ala | Gly | Gly | Thr | Thr | Cys | Thr |
|   |   | 8840 |   |   |   | 8845 |   |   |   | 8850 |   |
| Gly | Gly | Ala | Gly | Gly | Thr | Gly | Gly | Gly | Gly | Thr | Thr | Cys | Cys |
|   |   | 8855 |   |   |   | 8860 |   |   |   | 8865 |   |
| Ala | Cys | Gly | Cys | Gly | Thr | Ala | Thr | Gly | Gly | Thr | Gly | Ala | Gly | Cys |
|   |   | 8870 |   |   |   | 8875 |   |   |   | 8880 |   |
| Ala | Ala | Gly | Gly | Gly | Cys | Gly | Ala | Gly | Gly | Ala | Gly | Gly | Ala | Thr |
|   |   | 8885 |   |   |   | 8890 |   |   |   | 8895 |   |
| Ala | Ala | Cys | Ala | Thr | Gly | Gly | Cys | Cys | Ala | Thr | Cys | Ala | Thr | Cys |
|   |   | 8900 |   |   |   | 8905 |   |   |   | 8910 |   |

```
Ala Ala Gly Gly Ala Gly Thr  Thr Cys Ala Thr Gly  Cys Gly Cys
8915             8920              8925

Thr Thr Cys Ala Ala Gly Gly  Thr Gly Cys Ala Cys  Ala Thr Gly
8930             8935              8940

Gly Ala Gly Gly Gly Cys Thr  Cys Cys Gly Thr Gly  Ala Ala Cys
8945             8950              8955

Gly Gly Cys Cys Ala Cys Gly  Ala Gly Thr Thr Cys  Gly Ala Gly
8960             8965              8970

Ala Thr Cys Gly Ala Gly Gly  Gly Cys Gly Ala Gly  Gly Gly Cys
8975             8980              8985

Gly Ala Gly Gly Gly Cys Cys  Gly Cys Cys Cys Cys  Thr Ala Cys
8990             8995              9000

Gly Ala Gly Gly Gly Cys Ala  Cys Cys Cys Ala Gly  Ala Cys Cys
9005             9010              9015

Gly Cys Cys Ala Ala Gly Cys  Thr Gly Ala Ala Gly  Gly Thr Gly
9020             9025              9030

Ala Cys Cys Ala Ala Gly Gly  Gly Thr Gly Gly Cys  Cys Cys Cys
9035             9040              9045

Cys Thr Gly Cys Cys Cys Thr  Thr Cys Gly Cys Cys  Thr Gly Gly
9050             9055              9060

Gly Ala Cys Ala Thr Cys Cys  Thr Gly Thr Cys Cys  Cys Cys Thr
9065             9070              9075

Cys Ala Gly Thr Thr Cys Ala  Thr Gly Thr Ala Cys  Gly Gly Cys
9080             9085              9090

Thr Cys Cys Ala Ala Gly Gly  Cys Cys Thr Ala Cys  Gly Thr Gly
9095             9100              9105

Ala Ala Gly Cys Ala Cys Cys  Cys Cys Gly Cys Cys  Gly Ala Cys
9110             9115              9120

Ala Thr Cys Cys Cys Cys Gly  Ala Cys Thr Ala Cys  Thr Thr Gly
9125             9130              9135

Ala Ala Gly Cys Thr Gly Thr  Cys Cys Thr Thr Cys  Cys Cys Cys
9140             9145              9150

Gly Ala Gly Gly Gly Cys Thr  Thr Cys Ala Ala Gly  Thr Gly Gly
9155             9160              9165

Gly Ala Gly Cys Gly Cys Gly  Thr Gly Ala Thr Gly  Ala Ala Cys
9170             9175              9180

Thr Thr Cys Gly Ala Gly Gly  Ala Cys Gly Gly Cys  Gly Gly Cys
9185             9190              9195

Gly Thr Gly Gly Thr Gly Ala  Cys Cys Gly Thr Gly  Ala Cys Cys
9200             9205              9210

Cys Ala Gly Gly Ala Cys Thr  Cys Cys Thr Cys Cys  Cys Thr Gly
9215             9220              9225

Cys Ala Gly Gly Ala Cys Gly  Gly Cys Gly Ala Gly  Thr Thr Cys
9230             9235              9240

Ala Thr Cys Thr Ala Cys Ala  Ala Gly Gly Thr Gly  Ala Ala Gly
9245             9250              9255

Cys Thr Gly Cys Gly Cys Gly  Gly Cys Ala Cys Cys  Ala Ala Cys
9260             9265              9270

Thr Thr Cys Cys Cys Cys Thr  Cys Cys Gly Ala Cys  Gly Gly Cys
9275             9280              9285

Cys Cys Cys Gly Thr Ala Ala  Thr Gly Cys Ala Gly  Ala Ala Gly
9290             9295              9300
```

```
Ala Ala Gly Ala Cys Cys Ala Thr Gly Gly Cys Thr Gly Gly
    9305                9310                9315

Gly Ala Gly Gly Cys Cys Thr Cys Cys Thr Cys Cys Gly Ala Gly
    9320                9325                9330

Cys Gly Gly Ala Thr Gly Thr Ala Cys Cys Cys Gly Ala Gly
    9335                9340                9345

Gly Ala Cys Gly Gly Cys Gly Cys Cys Cys Thr Gly Ala Ala Gly
    9350                9355                9360

Gly Gly Cys Gly Ala Gly Ala Thr Cys Ala Ala Gly Cys Ala Gly
    9365                9370                9375

Ala Gly Gly Cys Thr Gly Ala Ala Gly Cys Thr Gly Ala Ala Gly
    9380                9385                9390

Gly Ala Cys Gly Gly Cys Gly Gly Cys Cys Ala Cys Thr Ala Cys
    9395                9400                9405

Gly Ala Cys Gly Cys Thr Gly Ala Gly Gly Thr Cys Ala Ala Gly
    9410                9415                9420

Ala Cys Cys Ala Cys Cys Thr Ala Cys Ala Ala Gly Gly Cys Cys
    9425                9430                9435

Ala Ala Gly Ala Ala Gly Cys Cys Cys Gly Thr Gly Cys Ala Gly
    9440                9445                9450

Cys Thr Gly Cys Cys Cys Gly Gly Cys Gly Cys Cys Thr Ala Cys
    9455                9460                9465

Ala Ala Cys Gly Thr Cys Ala Ala Cys Ala Thr Cys Ala Ala Gly
    9470                9475                9480

Thr Thr Gly Gly Ala Cys Ala Thr Cys Ala Cys Cys Thr Cys Cys
    9485                9490                9495

Cys Ala Cys Ala Ala Cys Gly Ala Gly Gly Ala Cys Thr Ala Cys
    9500                9505                9510

Ala Cys Cys Ala Thr Cys Gly Thr Gly Gly Ala Ala Cys Ala Gly
    9515                9520                9525

Thr Ala Cys Gly Ala Ala Cys Gly Cys Gly Cys Cys Gly Ala Gly
    9530                9535                9540

Gly Gly Cys Cys Gly Cys Cys Ala Cys Thr Cys Cys Ala Cys Cys
    9545                9550                9555

Gly Gly Cys Gly Gly Cys Ala Thr Gly Gly Ala Cys Gly Ala Gly
    9560                9565                9570

Cys Thr Gly Thr Ala Cys Ala Ala Gly Thr Ala Gly Gly Thr Cys
    9575                9580                9585

Gly Ala Cys Ala Ala Thr Cys Ala Ala Cys Cys Thr Cys Thr Gly
    9590                9595                9600

Gly Ala Thr Thr Ala Cys Ala Ala Ala Thr Thr Thr Gly Thr
    9605                9610                9615

Gly Ala Ala Ala Gly Ala Thr Thr Gly Ala Cys Thr Gly Gly Thr
    9620                9625                9630

Ala Thr Thr Cys Thr Thr Ala Ala Cys Thr Ala Thr Gly Thr Thr
    9635                9640                9645

Gly Cys Thr Cys Cys Thr Thr Thr Thr Ala Cys Gly Cys Thr Ala
    9650                9655                9660

Thr Gly Thr Gly Gly Ala Thr Ala Cys Gly Cys Thr Gly Cys Thr
    9665                9670                9675

Thr Thr Ala Ala Thr Gly Cys Cys Thr Thr Thr Gly Thr Ala Thr
    9680                9685                9690

Cys Ala Thr Gly Cys Thr Ala Thr Thr Gly Cys Thr Thr Cys Cys
```

-continued

```
                    9695                9700                9705
Cys Gly Thr Ala Thr Gly Gly Cys Thr Thr Thr Cys Ala Thr Thr
    9710                9715                9720
Thr Thr Cys Thr Cys Cys Thr Cys Cys Thr Thr Gly Thr Ala Thr
    9725                9730                9735
Ala Ala Ala Thr Cys Cys Thr Gly Gly Thr Thr Gly Cys Thr Gly
    9740                9745                9750
Thr Cys Thr Cys Thr Thr Thr Ala Thr Gly Ala Gly Gly Ala Gly
    9755                9760                9765
Thr Thr Gly Thr Gly Gly Cys Cys Cys Gly Thr Gly Thr Cys
    9770                9775                9780
Ala Gly Gly Cys Ala Ala Cys Gly Thr Gly Gly Cys Gly Thr Gly
    9785                9790                9795
Gly Thr Gly Thr Gly Cys Ala Cys Thr Gly Thr Gly Thr Thr Thr
    9800                9805                9810
Gly Cys Thr Gly Ala Cys Gly Cys Ala Ala Cys Cys Cys Cys
    9815                9820                9825
Ala Cys Thr Gly Gly Thr Thr Gly Gly Gly Gly Cys Ala Thr Thr
    9830                9835                9840
Gly Cys Cys Ala Cys Cys Ala Cys Cys Thr Gly Thr Cys Ala Gly
    9845                9850                9855
Cys Thr Cys Cys Thr Thr Thr Cys Cys Gly Gly Gly Ala Cys Thr
    9860                9865                9870
Thr Thr Cys Gly Cys Thr Thr Thr Cys Cys Cys Cys Thr Cys
    9875                9880                9885
Cys Cys Thr Ala Thr Gly Cys Cys Ala Cys Gly Gly Cys Gly
    9890                9895                9900
Gly Ala Ala Cys Thr Cys Ala Thr Cys Gly Cys Cys Gly Cys Cys
    9905                9910                9915
Thr Gly Cys Cys Thr Gly Cys Cys Cys Gly Cys Thr Gly Cys
    9920                9925                9930
Thr Gly Gly Ala Cys Ala Gly Gly Gly Cys Thr Cys Gly Gly
    9935                9940                9945
Cys Thr Gly Thr Thr Gly Gly Gly Cys Ala Cys Thr Gly Ala Cys
    9950                9955                9960
Ala Ala Thr Thr Cys Cys Gly Thr Gly Gly Thr Gly Thr Thr Gly
    9965                9970                9975
Thr Cys Gly Gly Gly Gly Ala Ala Gly Cys Thr Gly Ala Cys Gly
    9980                9985                9990
Thr Cys Cys Thr Thr Thr Cys Cys Thr Thr Gly Gly Cys Thr Gly
    9995                10000               10005
Cys Thr Cys Gly Cys Cys Thr Gly Thr Gly Thr Thr Gly Cys Cys
    10010               10015               10020
Ala Cys Cys Thr Gly Gly Ala Thr Thr Cys Thr Gly Cys Gly Cys
    10025               10030               10035
Gly Gly Gly Ala Cys Gly Thr Cys Cys Thr Thr Cys Thr Gly Cys
    10040               10045               10050
Thr Ala Cys Gly Thr Cys Cys Cys Thr Thr Cys Gly Cys Cys
    10055               10060               10065
Cys Thr Cys Ala Ala Thr Cys Cys Ala Gly Cys Gly Gly Ala Cys
    10070               10075               10080
Cys Thr Thr Cys Cys Thr Thr Cys Cys Cys Gly Cys Gly Gly Cys
    10085               10090               10095
```

-continued

```
Cys Thr Gly Cys Thr Gly Cys  Cys Gly Gly Cys  Thr Cys Thr Gly
        10100            10105              10110
Cys Gly Gly Cys Cys Thr Cys  Thr Thr Cys Cys Gly  Cys Gly Thr
        10115            10120               10125
Cys Thr Thr Cys Gly Cys Cys  Thr Thr Cys Gly Cys  Cys Cys Thr
        10130            10135              10140
Cys Ala Gly Ala Cys Gly Ala  Gly Thr Cys Gly Gly  Ala Thr Cys
        10145            10150              10155
Thr Cys Cys Cys Thr Thr Thr  Gly Gly Gly Cys Cys  Gly Cys Cys
        10160            10165              10170
Thr Cys Cys Cys Cys Gly Cys  Cys Thr Gly Gly Ala  Ala Thr Thr
        10175            10180              10185
Cys Gly Ala Gly Cys Thr Cys  Gly Gly Thr Ala Cys  Cys Thr Thr
        10190            10195              10200
Thr Ala Ala Gly Ala Cys Cys  Ala Ala Thr Gly Ala  Cys Thr Thr
        10205            10210              10215
Ala Cys Ala Ala Gly Gly Cys  Ala Gly Cys Thr Gly  Thr Ala Gly
        10220            10225              10230
Ala Thr Cys Thr Thr Ala Gly  Cys Cys Ala Cys Thr  Thr Thr Thr
        10235            10240              10245
Thr Ala Ala Ala Ala Gly Ala  Ala Ala Ala Gly Gly  Gly Gly Gly
        10250            10255              10260
Gly Ala Cys Thr Gly Gly Ala  Ala Gly Gly Gly Cys  Thr Ala Ala
        10265            10270              10275
Thr Thr Cys Ala Cys Thr Cys  Cys Cys Ala Ala Cys  Gly Ala Ala
        10280            10285              10290
Gly Ala Cys Ala Ala Gly Ala  Thr Cys Thr Gly Cys  Thr Thr Thr
        10295            10300              10305
Thr Thr Gly Cys Thr Thr Gly  Thr Ala Cys Thr Gly  Gly Gly Thr
        10310            10315              10320
Cys Thr Cys Thr Cys Thr Gly  Gly Thr Thr Ala Gly  Ala Cys Cys
        10325            10330              10335
Ala Gly Ala Thr Cys Thr Gly  Ala Gly Cys Cys Thr  Gly Gly Gly
        10340            10345              10350
Ala Gly Cys Thr Cys Thr Cys  Thr Gly Gly Cys Thr  Ala Ala Cys
        10355            10360              10365
Thr Ala Gly Gly Gly Ala Ala  Cys Cys Cys Ala Cys  Thr Gly Cys
        10370            10375              10380
Thr Thr Ala Ala Gly Cys Cys  Thr Cys Ala Ala Thr  Ala Ala Ala
        10385            10390              10395
Gly Cys Thr Thr Gly Cys Cys  Thr Thr Gly Ala Gly  Thr Gly Cys
        10400            10405              10410
Thr Thr Cys Ala Ala Gly Thr  Ala Gly Thr Gly Thr  Gly Thr Gly
        10415            10420              10425
Cys Cys Cys Gly Thr Cys Thr  Gly Thr Thr Gly Thr  Gly Thr Gly
        10430            10435              10440
Ala Cys Thr Cys Thr Gly Gly  Thr Ala Ala Cys Thr  Ala Gly Ala
        10445            10450              10455
Gly Ala Thr Cys Cys Cys Thr  Cys Ala Gly Ala Cys  Cys Cys Thr
        10460            10465              10470
Thr Thr Thr Ala Gly Thr Cys  Ala Gly Thr Gly Thr  Gly Gly Ala
        10475            10480              10485
```

```
Ala Ala   Ala Thr Cys Thr Cys   Thr Ala Gly Cys Ala   Gly Thr Ala
   10490              10495               10500

Gly Thr   Ala Gly Thr Thr Cys   Ala Thr Gly Thr Cys   Ala Thr Cys
   10505              10510               10515

Thr Thr   Ala Thr Thr Ala Thr   Thr Cys Ala Gly Thr   Ala Thr Thr
   10520              10525               10530

Thr Ala   Thr Ala Ala Cys Thr   Thr Gly Cys Ala Ala   Ala Gly Ala
   10535              10540               10545

Ala Ala   Thr Gly Ala Ala Thr   Ala Thr Cys Ala Gly   Ala Gly Ala
   10550              10555               10560

Gly Thr   Gly Ala Gly Ala Gly   Gly Ala Ala Cys Thr   Thr Gly Thr
   10565              10570               10575

Thr Thr   Ala Thr Thr Gly Cys   Ala Gly Cys Thr Thr   Ala Thr Ala
   10580              10585               10590

Ala Thr   Gly Gly Thr Thr Ala   Cys Ala Ala Ala Thr   Ala Ala Ala
   10595              10600               10605

Gly Cys   Ala Ala Thr Ala Gly   Cys Ala Thr Cys Ala   Cys Ala Ala
   10610              10615               10620

Ala Thr   Thr Thr Cys Ala Cys   Ala Ala Ala Thr Ala   Ala Ala Gly
   10625              10630               10635

Cys Ala   Thr Thr Thr Thr Thr   Thr Thr Cys Ala Cys   Thr Gly Cys
   10640              10645               10650

Ala Thr   Thr Cys Thr Ala Gly   Thr Thr Gly Thr Gly   Gly Thr Thr
   10655              10660               10665

Thr Gly   Thr Cys Cys Ala Ala   Ala Cys Thr Cys Ala   Thr Cys Ala
   10670              10675               10680

Ala Thr   Gly Thr Ala Thr Cys   Thr Thr Ala Thr Cys   Ala Thr Gly
   10685              10690               10695

Thr Cys   Thr Gly Gly Cys Thr   Cys Thr Ala Gly Cys   Thr Ala Thr
   10700              10705               10710

Cys Cys   Cys Gly Cys Cys Cys   Cys Thr Ala Ala Cys   Thr Cys Cys
   10715              10720               10725

Gly Cys   Cys Cys Ala Gly Thr   Thr Cys Cys Gly Cys   Cys Cys Ala
   10730              10735               10740

Thr Thr   Cys Thr Cys Cys Gly   Cys Cys Cys Cys Ala   Thr Gly Gly
   10745              10750               10755

Cys Thr   Gly Ala Cys Thr Ala   Ala Thr Thr Thr Thr   Thr Thr Thr
   10760              10765               10770

Thr Ala   Thr Thr Thr Ala Thr   Gly Cys Ala Gly Ala   Gly Gly Cys
   10775              10780               10785

Cys Gly   Ala Gly Gly Cys Cys   Gly Cys Cys Thr Cys   Gly Gly Cys
   10790              10795               10800

Cys Thr   Cys Thr Gly Ala Gly   Cys Thr Ala Thr Thr   Cys Cys Ala
   10805              10810               10815

Gly Ala   Ala Gly Thr Ala Gly   Thr Gly Ala Gly Gly   Ala Gly Gly
   10820              10825               10830

Cys Thr   Thr Thr Thr Thr Thr   Gly Gly Ala Gly Gly   Cys Cys Thr
   10835              10840               10845

Ala Gly   Cys Thr Ala Gly Gly   Gly Ala Cys Gly Thr   Ala Cys Cys
   10850              10855               10860

Cys Ala   Ala Thr Thr Cys Gly   Cys Cys Cys Thr Ala   Thr Ala Gly
   10865              10870               10875

Thr Gly   Ala Gly Thr Cys Gly   Thr Ala Thr Thr Ala   Cys Gly Cys
```

-continued

```
                 10880              10885              10890
Gly Cys   Gly Cys Thr Cys Ala   Cys Thr Gly Gly Cys   Cys Gly Thr
     10895              10900              10905
Cys Gly   Thr Thr Thr Thr Ala   Cys Ala Ala Cys Gly   Thr Cys Gly
     10910              10915              10920
Thr Gly   Ala Cys Thr Gly Gly   Gly Ala Ala Ala Cys   Cys Cys Cys
     10925              10930              10935
Thr Gly   Gly Cys Gly Thr Thr   Ala Cys Cys Cys Ala   Ala Cys Thr
     10940              10945              10950
Thr Ala   Ala Thr Cys Gly Cys   Cys Thr Thr Gly Cys   Ala Gly Cys
     10955              10960              10965
Ala Cys   Ala Thr Cys Cys Cys   Cys Cys Thr Thr Thr   Cys Gly Cys
     10970              10975              10980
Cys Ala   Gly Cys Thr Gly Gly   Cys Gly Thr Ala Ala   Thr Ala Gly
     10985              10990              10995
Cys Gly   Ala Ala Gly Ala Gly   Gly Cys Cys Cys Gly   Cys Ala Cys
     11000              11005              11010
Cys Gly   Ala Thr Cys Gly Cys   Cys Cys Thr Thr Cys   Cys Cys Ala
     11015              11020              11025
Ala Cys   Ala Gly Thr Thr Gly   Cys Gly Cys Ala Gly   Cys Cys Thr
     11030              11035              11040
Gly Ala   Ala Thr Gly Gly Cys   Gly Ala Ala Thr Gly   Gly Gly Ala
     11045              11050              11055
Cys Gly   Cys Gly Cys Cys Cys   Thr Gly Thr Ala Gly   Cys Gly Gly
     11060              11065              11070
Cys Gly   Cys Ala Thr Thr Ala   Ala Gly Cys Gly Cys   Gly Gly Cys
     11075              11080              11085
Gly Gly   Gly Thr Gly Thr Gly   Gly Thr Gly Gly Thr   Thr Ala Cys
     11090              11095              11100
Gly Cys   Gly Cys Ala Gly Cys   Gly Thr Gly Ala Cys   Cys Gly Cys
     11105              11110              11115
Thr Ala   Cys Ala Cys Thr Thr   Gly Cys Cys Ala Gly   Cys Gly Cys
     11120              11125              11130
Cys Cys   Thr Ala Gly Cys Gly   Cys Cys Cys Gly Cys   Thr Cys Cys
     11135              11140              11145
Thr Thr   Thr Cys Gly Cys Thr   Thr Thr Cys Thr Thr   Cys Cys Cys
     11150              11155              11160
Thr Thr   Cys Cys Thr Thr Thr   Cys Thr Cys Gly Cys   Cys Ala Cys
     11165              11170              11175
Gly Thr   Thr Cys Gly Cys Cys   Gly Gly Cys Thr Thr   Thr Cys Cys
     11180              11185              11190
Cys Cys   Gly Thr Cys Ala Ala   Gly Cys Thr Cys Thr   Ala Ala Ala
     11195              11200              11205
Thr Cys   Gly Gly Gly Gly Gly   Cys Thr Cys Cys Cys   Thr Thr Thr
     11210              11215              11220
Ala Gly   Gly Gly Thr Thr Cys   Cys Gly Ala Thr Thr   Thr Ala Gly
     11225              11230              11235
Thr Gly   Cys Thr Thr Thr Ala   Cys Gly Gly Cys Ala   Cys Cys Thr
     11240              11245              11250
Cys Gly   Ala Cys Cys Cys Cys   Ala Ala Ala Ala Ala   Ala Cys Thr
     11255              11260              11265
Thr Gly   Ala Thr Thr Ala Gly   Gly Gly Thr Gly Ala   Thr Gly Gly
     11270              11275              11280
```

```
Thr Thr  Cys Ala Cys Gly Thr  Ala Gly Thr Gly  Gly Cys Cys
    11285            11290             11295

Ala Thr  Cys Gly Cys Cys Cys  Thr Gly Ala Thr  Gly Ala Cys
    11300            11305             11310

Gly Gly  Thr Thr Thr Thr Thr  Cys Gly Cys Cys  Thr Thr Thr
    11315            11320             11325

Gly Ala  Cys Gly Thr Thr Gly  Gly Ala Gly Thr  Cys Cys Ala Cys
    11330            11335             11340

Gly Thr  Thr Cys Thr Thr Thr  Ala Ala Thr Ala Gly  Thr Gly Gly
    11345            11350             11355

Ala Cys  Thr Cys Thr Thr Gly  Thr Thr Cys Cys Ala  Ala Ala Cys
    11360            11365             11370

Thr Gly  Gly Ala Ala Cys Ala  Ala Cys Ala Cys Thr  Cys Ala Ala
    11375            11380             11385

Cys Cys  Cys Thr Ala Thr Cys  Thr Cys Gly Gly Thr  Cys Thr Ala
    11390            11395             11400

Thr Thr  Cys Thr Thr Thr Thr  Gly Ala Thr Thr Thr  Ala Thr Ala
    11405            11410             11415

Ala Gly  Gly Gly Ala Thr Thr  Thr Thr Gly Cys Cys  Gly Ala Thr
    11420            11425             11430

Thr Thr  Cys Gly Gly Cys Cys  Thr Ala Thr Thr Gly  Gly Thr Thr
    11435            11440             11445

Ala Ala  Ala Ala Ala Ala Thr  Gly Ala Gly Cys Thr  Gly Ala Thr
    11450            11455             11460

Thr Thr  Ala Ala Cys Ala Ala  Ala Ala Ala Thr Thr  Thr Ala Ala
    11465            11470             11475

Cys Gly  Cys Gly Ala Ala Thr  Thr Thr Thr Ala Ala  Cys Ala Ala
    11480            11485             11490

Ala Ala  Thr Ala Thr Thr Ala  Ala Cys Gly Cys Thr  Thr Ala Cys
    11495            11500             11505

Ala Ala  Thr Thr Thr Ala Gly  Gly Thr Gly Gly Cys  Ala Cys Thr
    11510            11515             11520

Thr Thr  Thr Cys Gly Gly Gly  Gly Ala Ala Ala Thr  Gly Thr Gly
    11525            11530             11535

Cys Gly  Cys Gly Gly Ala Ala  Cys Cys Cys Cys Thr  Ala Thr Thr
    11540            11545             11550

Thr Gly  Thr Thr Thr Ala Thr  Thr Thr Thr Thr Cys  Thr Ala Ala
    11555            11560             11565

Ala Thr  Ala Cys Ala Thr Thr  Cys Ala Ala Ala Thr  Ala Thr Gly
    11570            11575             11580

Thr Ala  Thr Cys Cys Gly Cys  Thr Cys Ala Thr Gly  Ala Gly Ala
    11585            11590             11595

Cys Ala  Ala Thr Ala Ala Cys  Cys Cys Thr Gly Ala  Thr Ala Ala
    11600            11605             11610

Ala Thr  Gly Cys Thr Thr Cys  Ala Ala Thr Ala Ala  Thr Ala Thr
    11615            11620             11625

Thr Gly  Ala Ala Ala Ala Ala  Gly Gly Ala Ala Gly  Ala Gly Thr
    11630            11635             11640

Ala Thr  Gly Ala Gly Thr Ala  Thr Thr Cys Ala Ala  Cys Ala Thr
    11645            11650             11655

Thr Thr  Cys Cys Gly Thr Gly  Thr Cys Gly Cys Cys  Cys Thr Thr
    11660            11665             11670
```

-continued

| | | | | | | | | | | | | | |
|---|---|---|---|---|---|---|---|---|---|---|---|---|---|
| Ala | Thr 11675 | Thr | Cys | Cys | Cys | Thr 11680 | Thr | Thr | Thr | Thr | Thr 11685 | Gly | Cys | Gly |
| Gly | Cys 11690 | Ala | Thr | Thr | Thr | Thr 11695 | Gly | Cys | Cys | Thr | Thr 11700 | Cys | Cys | Thr |
| Gly | Thr 11705 | Thr | Thr | Thr | Thr | Gly 11710 | Cys | Thr | Cys | Ala | Cys 11715 | Cys | Cys | Ala |
| Gly | Ala 11720 | Ala | Ala | Cys | Gly | Cys 11725 | Thr | Gly | Gly | Thr | Gly 11730 | Ala | Ala | Ala |
| Gly | Thr 11735 | Ala | Ala | Ala | Ala | Gly 11740 | Ala | Thr | Gly | Cys | Thr 11745 | Gly | Ala | Ala |
| Gly | Ala 11750 | Thr | Cys | Ala | Gly | Thr 11755 | Thr | Gly | Gly | | | | | |

What is claimed is:

1. A composition comprising an ex vivo population of immune cells that express an enzyme that catalyzes the formation of aspartate from asparagine or the formation of alanine from pyruvate and glutamate.

2. The composition of claim 1, wherein the immune cells are T cells.

3. The composition of claim 2, wherein the immune cells are chimeric antigen receptor (CAR)-T cells.

4. The composition of claim 1, wherein the enzyme is asparaginase.

5. The composition of claim 4, wherein the asparaginase is a naturally-occurring asparaginase or a variant of a naturally-occurring asparaginase having at least about 80% amino acid sequence identity to a naturally-occurring asparaginase.

6. The composition of claim 4, wherein the asparaginase comprises, consists essentially of or consists of the sequence of SEQ ID NO:1.

7. A method of promoting an immune response in a subject in need thereof, comprising administering to the subject an effective amount of a population of immune cells that express an enzyme that catalyzes the formation of aspartate from asparagine or the formation of alanine from pyruvate and glutamate.

8. A method for treating a cancer in a subject in need thereof, comprising administering to the subject an effective amount of a population of anti-cancer immune cells that express an enzyme that catalyzes the formation of aspartate from asparagine or the formation of alanine from pyruvate and glutamate.

9. The method of claim 7, wherein the immune cells are T cells.

10. The method of claim 9, wherein the immune cells are CAR-T cells.

11. The method of claim 7, wherein the immune cells express asparaginase.

12. The method of claim 11, wherein the asparaginase is a naturally-occurring asparaginase or a variant of a naturally-occurring asparaginase having at least about 80% amino acid sequence identity to a naturally-occurring asparaginase.

13. The method of claim 11, wherein the asparaginase comprises, consists essentially of or consists of the sequence of SEQ ID NO:1.

14. The method of claim 7, further comprising administering one or more additional therapeutic agents to the subject.

15. The method of claim 14, wherein the one or more additional therapeutic agents comprises a checkpoint inhibitor.

16. The method of claim 15, wherein the checkpoint inhibitor is a PD-1, PD-L1 or CTLA-4 checkpoint inhibitor.

17. A method of enhancing an immunotherapy in a subject receiving the immunotherapy, comprising administering to the subject an effective amount of a population of immune cells that express an enzyme that catalyzes the formation of aspartate from asparagine or the formation of alanine from pyruvate and glutamate.

18. The method of claim 17, wherein the immunotherapy comprises a checkpoint inhibitor.

19. The method of claim 18, wherein the checkpoint inhibitor is a PD-1, PD-L1 or CTLA-4 checkpoint inhibitor.

20. The method of claim 17, wherein the immunotherapy is a CAR-T therapy.

* * * * *